(12) United States Patent
Polakis et al.

(10) Patent No.: US 10,017,577 B2
(45) Date of Patent: Jul. 10, 2018

(54) ANTIBODIES AND IMMUNOCONJUGATES

(71) Applicant: Genentech, Inc., South San Francisco, CA (US)

(72) Inventors: Paul Polakis, Mill Valley, CA (US); Peter Dragovich, San Diego, CA (US); Thomas Harden Pillow, San Francisco, CA (US); Shang-Fan Yu, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/181,618

(22) Filed: Jun. 14, 2016

(65) Prior Publication Data
US 2017/0002086 A1    Jan. 5, 2017

Related U.S. Application Data

(60) Provisional application No. 62/175,802, filed on Jun. 15, 2015.

(51) Int. Cl.
| | | |
|---|---|---|
| *A61K 39/395* | (2006.01) | |
| *C07K 16/30* | (2006.01) | |
| *C07K 16/28* | (2006.01) | |
| *C07K 16/32* | (2006.01) | |
| *C07K 16/40* | (2006.01) | |
| *A61K 47/68* | (2017.01) | |
| *A61K 39/00* | (2006.01) | |

(52) U.S. Cl.
CPC .......... *C07K 16/30* (2013.01); *A61K 47/6803* (2017.08); *A61K 47/6849* (2017.08); *A61K 47/6851* (2017.08); *A61K 47/6889* (2017.08); *C07K 16/28* (2013.01); *C07K 16/2803* (2013.01); *C07K 16/3015* (2013.01); *C07K 16/3023* (2013.01); *C07K 16/3092* (2013.01); *C07K 16/32* (2013.01); *C07K 16/40* (2013.01); *A61K 2039/505* (2013.01); *C07K 2317/515* (2013.01)

(58) Field of Classification Search
None
See application file for complete search history.

(56) References Cited

U.S. PATENT DOCUMENTS

| | | | |
|---|---|---|---|
| 5,677,171 A | 10/1997 | Hudziak et al. | |
| 6,054,297 A | 4/2000 | Carter et al. | |
| 6,165,464 A | 12/2000 | Hudziak et al. | |
| 6,214,345 B1 | 4/2001 | Firestone et al. | |
| 6,339,142 B1 | 1/2002 | Basey et al. | |
| 6,407,213 B1 | 6/2002 | Carter et al. | |
| 6,639,055 B1 | 10/2003 | Carter et al. | |
| 6,719,971 B1 | 4/2004 | Carter et al. | |
| 6,800,738 B1 | 10/2004 | Carter et al. | |
| 7,074,404 B2 | 7/2006 | Basey et al. | |
| 7,521,541 B2 * | 4/2009 | Eigenbrot | A61K 47/48538 424/133.1 |
| 7,855,275 B2 | 12/2010 | Eigenbrot et al. | |
| 7,989,595 B2 | 8/2011 | Dennis et al. | |
| 8,088,378 B2 | 1/2012 | Chen et al. | |
| 8,309,300 B2 | 11/2012 | Junutula et al. | |
| 8,362,213 B2 * | 1/2013 | Elkins | A61K 39/395 530/387.3 |
| 8,436,147 B2 | 5/2013 | Dennis et al. | |
| 9,000,130 B2 | 4/2015 | Bhakta et al. | |
| 9,290,578 B2 | 3/2016 | Asundi et al. | |
| 2004/0253232 A1 | 12/2004 | Jakobovits et al. | |
| 2007/0092940 A1 | 4/2007 | Eigenbrot et al. | |
| 2009/0175865 A1 | 9/2009 | Eigenbrot et al. | |
| 2010/0003766 A1 | 1/2010 | Eigenbrot et al. | |
| 2010/0111856 A1 | 5/2010 | Gill et al. | |
| 2011/0137017 A1 | 6/2011 | Eigenbrot et al. | |
| 2011/0142859 A1 | 6/2011 | Ebens, Jr. et al. | |
| 2011/0301334 A1 | 12/2011 | Bhakta et al. | |
| 2014/0288280 A1 | 9/2014 | Bhakta et al. | |
| 2014/0356375 A1 | 12/2014 | Brown et al. | |
| 2015/0017094 A1 | 1/2015 | Gill et al. | |
| 2015/0017188 A1 | 1/2015 | Eigenbrot et al. | |
| 2015/0032218 A1 | 1/2015 | Landon | |
| 2015/0165063 A1 | 6/2015 | Flygare et al. | |
| 2015/0366985 A1 | 12/2015 | Brown et al. | |
| 2016/0074529 A1 | 3/2016 | Brown et al. | |
| 2016/0096893 A1* | 4/2016 | Chen | A61K 47/48615 424/133.1 |
| 2016/0130358 A1 | 5/2016 | Bhakta et al. | |
| 2016/0199508 A1 | 7/2016 | Sakanaka et al. | |
| 2016/0279260 A1 | 9/2016 | Flygare et al. | |
| 2016/0310611 A1 | 10/2016 | Flygare et al. | |
| 2016/0354485 A1 | 12/2016 | Flygare et al. | |
| 2017/0002086 A1 | 1/2017 | Polakis et al. | |

FOREIGN PATENT DOCUMENTS

| | | | |
|---|---|---|---|
| DE | 102009051799 A1 | 5/2011 | |
| WO | 98/17797 A1 | 4/1998 | |
| WO | 1998/019705 A1 | 5/1998 | |
| WO | 2006/130669 A2 | 12/2006 | |

(Continued)

OTHER PUBLICATIONS

Strome et al., The Oncologist, 2007; 12:1084-95.*
Brand et al., Anticancer Res. 2006; 26:463-70.*
Cabezudo et al. et al., "Quantitative analysis of CD79b, CD5 and CD19 in mature B-cell lymphoproliferative disorders" Haematologica 84(5):413-418 (May 1999).
D'Arena et al. et al., "Quantitative flow cytometry for the differential diagnosis of leukemic B-cell chronic lymphoproliferative disorders" Am J Hematol 64(4):275-281 (Aug. 2000).
Invitation to Pay Additional Fees and, Where Applicable, Protest Fee for International Application No. PCT/US2016/037333, pp. 7 (dated Aug. 17, 2016).

(Continued)

*Primary Examiner* — Sheela J. Huff
(74) *Attorney, Agent, or Firm* — McNeill Baur PLLC

(57) ABSTRACT

The invention provides immunoconjugates and methods of using the same.

38 Claims, 8 Drawing Sheets

(56) References Cited

FOREIGN PATENT DOCUMENTS

| | | | |
|---|---|---|---|
| WO | 2009/141240 A1 | | 11/2009 |
| WO | 2009/148554 A1 | | 12/2009 |
| WO | 2011/156328 A1 | | 12/2011 |
| WO | 2013/041606 A1 | | 3/2013 |
| WO | 2013/065009 A1 | | 5/2013 |
| WO | 2013/177055 | * | 11/2013 |
| WO | 2013/177055 A2 | | 11/2013 |
| WO | 2014/039092 A1 | | 3/2014 |
| WO | 2014/193722 A1 | | 12/2014 |
| WO | 2014/194247 A1 | | 12/2014 |
| WO | 2015/023355 A1 | | 2/2015 |
| WO | 2015/061209 A1 | | 4/2015 |
| WO | 2015/095124 A1 | | 6/2015 |
| WO | 2015/095212 A1 | | 6/2015 |
| WO | 2015/095223 A2 | | 6/2015 |
| WO | 2015/095227 | * | 6/2015 |
| WO | 2016/040856 | * | 3/2016 |
| WO | 2016/040856 A2 | | 3/2016 |
| WO | 2016/090038 A1 | | 6/2016 |
| WO | 2016/090040 A1 | | 6/2016 |
| WO | 2016/090050 A1 | | 6/2016 |
| WO | 2016/205176 A1 | | 12/2016 |

OTHER PUBLICATIONS

Mao et al., "RIG-E, a human homolog of the murine Ly-6 family, is induced by retinoic acid during the differentiation of acute promyelocytic leukemia cell" Proc. Natl. Acad. Sci. USA 93:5910-5914 (1996).

Matsuuchi et al. et al., "New views of BCR structure and organization" Curr Opin Immunol 13(3):270-277 (Jun. 2001).

McLemore et al., "Introducing the MUC16 gene: implications for prevention and early detection in epithelial ovarian cancer" Biol. Res. Nurs. 6(4):262-267 ( 2005).

Olejniczak et al. et al., "A quantitative exploration of surface antigen expression in common B-cell malignancies using flow cytometry" Immunol Invest 35(1):93-114 ( 2006).

Press et al., "Her-2/neu Expression in Node-negative Breast Cancer: Direct Tissue Quantitation by Computerized Image Analysis and Association of Overexpression with Increased Risk of Recurrent Disease" Cancer Research 53:4960-4970 ( 1993).

Slamon et al., "Human breast cancer: correlation of relapse and survival with amplification of the HER-2/neu oncogene" Science 235(4785):177-182 ( 1987).

Wong et al., "Characterization of the Oligosaccharides Associated with the Human Ovarian Tumor Marker CA125" The Journal of Biological Chemistry 278(31):28619-28634 (2003).

Doronina et al., "Novel peptide linkers for highly potent antibody-auristatin conjugate" Bioconjug Chem. 19(10):1960-3 ( 2008).

Ducry et al., "Antibody—Drug Conjugates: Linking Cytotoxic Payloads to Monoclonal Antibodies" Bioconjugate Chem. 21:5-13 ( 2010).

Nolting, Methods in Molecular Biology "Chapter 5 Linker Technologies for AntibodyDrug Conjugates" ED Laurent Ducry, Humana Press edition, vol. 1045:71-100 ( Jan. 1, 2013).

O'Brien et al. et al., "The CA 125 gene: a newly discovered extension of the glycosylated N-terminal domain doubles the size of this extracellular superstructure" Tumour Biol 23(3):154-169 ( 2002).

O'Brien et al. et al., "The CA 125 gene: an extracellular superstructure dominated by repeat sequences" Tumour Biol 22(6):348-366 ( 2001).

PCT International Search Report and Written Opinion for PCT/US2014/070660, dated Oct. 1, 2015 (25 pages).

Pozzo et al., "Conjugates of a Novel 7-Substituted Camptothecin with RGD-Peptides as αvβ3 Integrin Ligands: An Approach to Tumor-Targeted Therapy" Bioconjugate Chem. 21(11):195667 (Nov. 17, 2010).

Tercel et al., "Unsymmetrical DNA cross-linking agents: Combination of the CBI and PBD Pharmacophores" J. Med. Chem. 46(11):2132-2151 (Jan. 2003).

* cited by examiner

SEQUENCE LISTING

<160> NUMBER OF SEQ ID NOS: 85

<210> SEQ ID NO 1
<211> LENGTH: 107
<212> TYPE: PRT
<213> ORGANISM: Artificial Sequence
<220> FEATURE:
<223> OTHER INFORMATION: Synthetic: anti-Ly6E antibody hu9B12 v12 light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

```
Leu Asn Trp Tyr Gln Gln Lys Pro Gly Lys Thr Val Lys Leu Leu Ile
         35                  40                  45

Tyr Tyr Thr Ser Asn Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Ser Glu Leu Pro Trp
                 85                  90                  95

Thr Phe Gly Gln Gly Thr Lys Val Glu Ile Lys
            100                 105

<210> SEQ ID NO 2
<211> LENGTH: 120
<212> TYPE: PRT
<213> ORGANISM: Artificial Sequence
<220> FEATURE:
<223> OTHER INFORMATION: Synthetic: anti-Ly6E antibody hu9B12 v12 heavy
      chain variable region

<400> SEQUENCE: 2

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
         35                  40                  45

Gly Met Ile Trp Gly Asp Gly Ser Thr Asp Tyr Asn Ser Ala Leu Lys
 50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                 85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser
        115                 120

<210> SEQ ID NO 3
<211> LENGTH: 11
<212> TYPE: PRT
<213> ORGANISM: Artificial Sequence
<220> FEATURE:
<223> OTHER INFORMATION: Synthetic: anti-Ly6E antibody hu9B12 v12 HVR-L1

<400> SEQUENCE: 3

Ser Ala Ser Gln Gly Ile Ser Asn Tyr Leu Asn
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic: anti-Ly6E antibody hu9B12 v12 HVR-L2

<400> SEQUENCE: 4

Tyr Thr Ser Asn Leu His Ser
1               5

<210> SEQ ID NO 5
<211> LENGTH: 9
```

```
<212> TYPE: PRT
<213> ORGANISM: Artificial Sequence
<220> FEATURE:
<223> OTHER INFORMATION: Synthetic: anti-Ly6E antibody hu9B12 v12 HVR-L3

<400> SEQUENCE: 5

Gln Gln Tyr Ser Glu Leu Pro Trp Thr
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic: anti-Ly6E antibody hu9B12 v12 HVR-H1

<400> SEQUENCE: 6

Gly Phe Ser Leu Thr Gly Tyr Ser Val Asn
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic: anti-Ly6E antibody hu9B12 v12 HVR-H2

<400> SEQUENCE: 7

Met Ile Trp Gly Asp Gly Ser Thr Asp Tyr Asn Ser Ala Leu Lys Ser
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Synthetic: anti-Ly6E antibody hu9B12 v12 HVR-H3

<400> SEQUENCE: 8

Asp Tyr Tyr Phe Asn Tyr Ala Ser Trp Phe Ala Tyr
1               5                   10

<210> SEQ ID NO 9
<211> LENGTH: 214
<212> TYPE: PRT
<213> ORGANISM: Artificial Sequence
<220> FEATURE:
<223> OTHER INFORMATION: Synthetic: anti-Ly6E antibody hu9B12 v12 K149C
      kappa light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys Arg Thr Val Ala Ala
```

```
                    100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 10
<211> LENGTH: 450
<212> TYPE: PRT
<213> ORGANISM: Artificial Sequence
<220> FEATURE:
<223> OTHER INFORMATION: Synthetic: anti-Ly6E antibody hu9B12 v12 IgG1
      heavy chain

<400> SEQUENCE: 10

```
Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 11
<211> LENGTH: 214
<212> TYPE: PRT
<213> ORGANISM: Artificial Sequence
<220> FEATURE:
<223> OTHER INFORMATION: Synthetic: Trastuzumab light chain

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 107
<212> TYPE: PRT
<213> ORGANISM: Artificial Sequence
<220> FEATURE:
<223> OTHER INFORMATION: Synthetic: Trastuzumab light chain variable
      region

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 13
<211> LENGTH: 451
<212> TYPE: PRT
<213> ORGANISM: Artificial Sequence
<220> FEATURE:
<223> OTHER INFORMATION: Synthetic: Trastuzumab heavy chain

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val

```
            115                 120                 125
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 14
<211> LENGTH: 120
<212> TYPE: PRT
<213> ORGANISM: Artificial Sequence
<220> FEATURE:
<223> OTHER INFORMATION: Synthetic: Trastuzumab heavy chain variable
      region

<400> SEQUENCE: 14

Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 15
<211> LENGTH: 11
<212> TYPE: PRT
<213> ORGANISM: Artificial Sequence
<220> FEATURE:
<223> OTHER INFORMATION: Synthetic: Anti-Muc16 antibody #1 HVR-L1

<400> SEQUENCE: 15

Lys Ala Ser Asp Leu Ile His Asn Trp Leu Ala
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic: Anti-Muc16 antibody #1 HVR-L2

<400> SEQUENCE: 16

Ser Gly Ala Thr Ser Leu Glu Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic: Anti-Muc16 antibody #1 HVR-L3

<400> SEQUENCE: 17

Gln Gln Tyr Trp Thr Thr Pro Phe Thr
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic: Anti-Muc16 antibody #1 HVR-H1

<400> SEQUENCE: 18

Gly Tyr Ser Ile Thr Asn Asp Tyr Ala Trp Asn
1               5                   10

<210> SEQ ID NO 19
<211> LENGTH: 15
<212> TYPE: PRT
<213> ORGANISM: Artificial Sequence
<220> FEATURE:

<223> OTHER INFORMATION: Synthetic: Anti-Muc16 antibody #1 HVR-H2

<400> SEQUENCE: 19

Gly Tyr Ile Asn Tyr Ser Gly Tyr Thr Thr Tyr Asn Pro Ser Leu
1               5                   10                  15

<210> SEQ ID NO 20
<211> LENGTH: 9
<212> TYPE: PRT
<213> ORGANISM: Artificial Sequence
<220> FEATURE:
<223> OTHER INFORMATION: Synthetic: Anti-Muc16 antibody #1 HVR-H3

<400> SEQUENCE: 20

Ala Arg Trp Asp Gly Gly Leu Thr Tyr
1               5

<210> SEQ ID NO 21
<211> LENGTH: 107
<212> TYPE: PRT
<213> ORGANISM: Artificial Sequence
<220> FEATURE:
<223> OTHER INFORMATION: Synthetic: Anti-Muc16 antibody #1 light chain
      variable region

<400> SEQUENCE: 21

Asp Ile Gln Met Thr Gln Ser Ser Phe Leu Ser Val Ser Leu Gly
1               5                   10                  15

Gly Arg Val Thr Ile Thr Cys Lys Ala Ser Asp Leu Ile His Asn Trp
                20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Asn Asp Tyr Thr Leu Ser Ile Ala Ser Leu Gln Thr
65                  70                  75                  80

Glu Asp Ala Ala Thr Tyr Tyr Cys Gln Gln Tyr Trp Thr Thr Pro Phe
                85                  90                  95

Thr Phe Gly Ser Gly Thr Lys Leu Glu Ile Lys
            100                 105

<210> SEQ ID NO 22
<211> LENGTH: 116
<212> TYPE: PRT
<213> ORGANISM: Artificial Sequence
<220> FEATURE:
<223> OTHER INFORMATION: Synthetic: Anti-Muc16 antibody #1  heavy chain
      variable region

<400> SEQUENCE: 22

Asp Val Gln Leu Gln Glu Ser Gly Pro Gly Leu Val Asn Pro Ser Gln
1               5                   10                  15

Ser Leu Ser Leu Thr Cys Thr Val Thr Gly Tyr Ser Ile Thr Asn Asp
                20                  25                  30

Tyr Ala Trp Asn Trp Ile Arg Gln Phe Pro Gly Asn Lys Leu Glu Trp
            35                  40                  45

Met Gly Tyr Ile Asn Tyr Ser Gly Tyr Thr Thr Tyr Asn Pro Ser Leu
        50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Glu Asp Thr Ala Thr Tyr Tyr Cys

```
                 85                  90                  95
Ala Arg Trp Asp Gly Gly Leu Thr Tyr Trp Gly Gln Gly Thr Leu Val
            100                 105                 110

Thr Val Ser Ala
        115

<210> SEQ ID NO 23
<211> LENGTH: 11
<212> TYPE: PRT
<213> ORGANISM: Artificial Sequence
<220> FEATURE:
<223> OTHER INFORMATION: Synthetic: Anti-Muc16 antibody #2 HVR-L1

<400> SEQUENCE: 23

Lys Ala Ser Asp Leu Ile His Asn Trp Leu Ala
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Synthetic: Anti-Muc16 antibody #2 HVR-L2

<400> SEQUENCE: 24

Tyr Gly Ala Thr Ser Leu Glu Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic: Anti-Muc16 antibody #2 HVR-L3

<400> SEQUENCE: 25

Gln Gln Tyr Trp Thr Thr Pro Phe Thr
1               5

<210> SEQ ID NO 26
<211> LENGTH: 11
<212> TYPE: PRT
<213> ORGANISM: Artificial Sequence
<220> FEATURE:
<223> OTHER INFORMATION: Synthetic: Anti-Muc16 antibody #2 HVR-H1

<400> SEQUENCE: 26

Gly Tyr Ser Ile Thr Asn Asp Tyr Ala Trp Asn
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Synthetic: Anti-Muc16 antibody #2 HVR-H2

<400> SEQUENCE: 27

Gly Tyr Ile Ser Tyr Ser Gly Tyr Thr Thr Tyr Asn Pro Ser Leu Lys
1               5                   10                  15

Ser

<210> SEQ ID NO 28
<211> LENGTH: 9
<212> TYPE: PRT
```

```
<213> ORGANISM: Artificial Sequence
<220> FEATURE:
<223> OTHER INFORMATION: Synthetic: Anti-Muc16 antibody #2 HVR-H3

<400> SEQUENCE: 28

Ala Arg Trp Thr Ser Gly Leu Asp Tyr
1               5

<210> SEQ ID NO 29
<211> LENGTH: 108
<212> TYPE: PRT
<213> ORGANISM: Artificial Sequence
<220> FEATURE:
<223> OTHER INFORMATION: Synthetic: Anti-Muc16 antibody #2 light chain
      variable region

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 30
<211> LENGTH: 116
<212> TYPE: PRT
<213> ORGANISM: Artificial Sequence
<220> FEATURE:
<223> OTHER INFORMATION: Synthetic: Anti-Muc16 antibody #2 heavy chain
      variable region

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Thr Ser Gly Leu Asp Tyr Trp Gly Gln Gly Thr Leu Val
            100                 105                 110

Thr Val Ser Ser
        115

<210> SEQ ID NO 31
<211> LENGTH: 11
```

```
<212> TYPE: PRT
<213> ORGANIZM: Artificial Sequence
<220> FEATURE:
<223> OTHER INFORMATION: Synthetic: Anti-Muc16 antibody #3 HVR-L1

<400> SEQUENCE: 31

Lys Ala Ser Asp Leu Ile His Asn Trp Leu Ala
1               5                   10

<210> SEQ ID NO 32
<211> LENGTH: 8
<212> TYPE: PRT
<213> ORGANISM: Artificial Sequence
<220> FEATURE:
<223> OTHER INFORMATION: Synthetic: Anti-Muc16 antibody #3 HVR-L2

<400> SEQUENCE: 32

Tyr Gly Ala Thr Ser Leu Glu Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic: Anti-Muc16 antibody #3 HVR-L3

<400> SEQUENCE: 33

Gln Gln Tyr Trp Thr Thr Pro Phe Thr
1               5

<210> SEQ ID NO 34
<211> LENGTH: 11
<212> TYPE: PRT
<213> ORGANISM: Artificial Sequence
<220> FEATURE:
<223> OTHER INFORMATION: Synthetic: Anti-Muc16 antibody #3 HVR-H1

<400> SEQUENCE: 34

Gly Tyr Ser Ile Thr Asn Asp Tyr Ala Trp Asn
1               5                   10

<210> SEQ ID NO 35
<211> LENGTH: 17
<212> TYPE: PRT
<213> ORGANISM: Artificial Sequence
<220> FEATURE:
<223> OTHER INFORMATION: Synthetic: Anti-Muc16 antibody #3 HVR-H2

<400> SEQUENCE: 35

Gly Tyr Ile Ser Tyr Ser Gly Tyr Thr Thr Tyr Asn Pro Ser Leu Lys
1               5                   10                  15

Ser

<210> SEQ ID NO 36
<211> LENGTH: 9
<212> TYPE: PRT
<213> ORGANISM: Artificial Sequence
<220> FEATURE:
<223> OTHER INFORMATION: Synthetic: Anti-Muc16 antibody #3 HVR-H3

<400> SEQUENCE: 36

Ala Arg Trp Ala Ser Gly Leu Asp Tyr
1               5

<210> SEQ ID NO 37
```

```
<211> LENGTH: 108
<212> TYPE: PRT
<213> ORGANISM: Artificial Sequence
<220> FEATURE:
<223> OTHER INFORMATION: Synthetic: Anti-Muc16 antibody #3 light chain
      variable region

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 38
<211> LENGTH: 116
<212> TYPE: PRT
<213> ORGANISM: Artificial Sequence
<220> FEATURE:
<223> OTHER INFORMATION: Synthetic: Anti-Muc16 antibody #3 heavy chain
      variable region

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115

<210> SEQ ID NO 39
<211> LENGTH: 11
<212> TYPE: PRT
<213> ORGANISM: Artificial Sequence
<220> FEATURE:
<223> OTHER INFORMATION: Synthetic: Anti-Muc16 antibody #4 HVR-L1

<400> SEQUENCE: 39

Lys Ala Ser Asp Leu Ile His Asn Trp Leu Ala
1               5                   10
```

<210> SEQ ID NO 40
<211> LENGTH: 8
<212> TYPE: PRT
<213> ORGANISM: Artificial Sequence
<220> FEATURE:
<223> OTHER INFORMATION: Synthetic: Anti-Muc16 antibody #4 HVR-L2

<400> SEQUENCE: 40

Tyr Gly Ala Thr Ser Leu Glu Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic: Anti-Muc16 antibody #4 HVR-L3

<400> SEQUENCE: 41

Gln Gln Tyr Trp Thr Thr Pro Phe Thr
1               5

<210> SEQ ID NO 42
<211> LENGTH: 11
<212> TYPE: PRT
<213> ORGANISM: Artificial Sequence
<220> FEATURE:
<223> OTHER INFORMATION: Synthetic: Anti-Muc16 antibody #4 HVR-H1

<400> SEQUENCE: 42

Gly Tyr Ser Ile Thr Asn Asp Tyr Ala Trp Asn
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Synthetic: Anti-Muc16 antibody #4 HVR-H2

<400> SEQUENCE: 43

Gly Tyr Ile Asn Tyr Ala Gly Tyr Thr Thr Tyr Asn Pro Ser Leu Lys
1               5                   10                  15

Ser

<210> SEQ ID NO 44
<211> LENGTH: 9
<212> TYPE: PRT
<213> ORGANISM: Artificial Sequence
<220> FEATURE:
<223> OTHER INFORMATION: Synthetic: Anti-Muc16 antibody #4 HVR-H3

<400> SEQUENCE: 44

Ala Arg Trp Ala Ser Gly Leu Asp Tyr
1               5

<210> SEQ ID NO 45
<211> LENGTH: 108
<212> TYPE: PRT
<213> ORGANISM: Artificial Sequence
<220> FEATURE:
<223> OTHER INFORMATION: Synthetic: Anti-Muc16 antibody #4 light chain
      variable region

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 46
<211> LENGTH: 116
<212> TYPE: PRT
<213> ORGANISM: Artificial Sequence
<220> FEATURE:
<223> OTHER INFORMATION: Synthetic: Anti-Muc16 antibody #4 heavy chain
      variable region

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Asn Tyr Ala Gly Tyr Thr Tyr Asn Pro Ser Leu
50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115

<210> SEQ ID NO 47
<211> LENGTH: 117
<212> TYPE: PRT
<213> ORGANISM: Artificial Sequence
<220> FEATURE:
<223> OTHER INFORMATION: Synthetic: huMA79bv28 heavy chain variable
      region

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Asp Thr Asn Tyr Asn Glu Ile Phe
50                  55                  60

Lys Gly Arg Ala Thr Phe Ser Ala Asp Thr Ser Lys Asn Thr Ala Tyr
65                  70                  75                  80

```
Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115

<210> SEQ ID NO 48
<211> LENGTH: 112
<212> TYPE: PRT
<213> ORGANISM: Artificial Sequence
<220> FEATURE:
<223> OTHER INFORMATION: Synthetic: huMA79bv28 light chain variable
      region

<400> SEQUENCE: 48

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

<210> SEQ ID NO 49
<211> LENGTH: 10
<212> TYPE: PRT
<213> ORGANISM: Artificial Sequence
<220> FEATURE:
<223> OTHER INFORMATION: Synthetic: huMA79bv28 HVR H1

<400> SEQUENCE: 49

Gly Tyr Thr Phe Ser Ser Tyr Trp Ile Glu
1               5                   10

<210> SEQ ID NO 50
<211> LENGTH: 18
<212> TYPE: PRT
<213> ORGANISM: Artificial Sequence
<220> FEATURE:
<223> OTHER INFORMATION: Synthetic: huMA79bv28 HVR H2

<400> SEQUENCE: 50

Gly Glu Ile Leu Pro Gly Gly Gly Asp Thr Asn Tyr Asn Glu Ile Phe
1               5                   10                  15

Lys Gly

<210> SEQ ID NO 51
<211> LENGTH: 10
<212> TYPE: PRT
<213> ORGANISM: Artificial Sequence
<220> FEATURE:
<223> OTHER INFORMATION: Synthetic: huMA79bv28 HVR H3

<400> SEQUENCE: 51
```

```
Thr Arg Arg Val Pro Ile Arg Leu Asp Tyr
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Synthetic: huMA79bv28 HVR L1

<400> SEQUENCE: 52

Lys Ala Ser Gln Ser Val Asp Tyr Glu Gly Asp Ser Phe Leu Asn
1               5                   10                  15

<210> SEQ ID NO 53
<211> LENGTH: 7
<212> TYPE: PRT
<213> ORGANISM: Artificial Sequence
<220> FEATURE:
<223> OTHER INFORMATION: Synthetic: huMA79bv28 HVR L2

<400> SEQUENCE: 53

Ala Ala Ser Asn Leu Glu Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic: huMA79bv28 HVR L3

<400> SEQUENCE: 54

Gln Gln Ser Asn Glu Asp Pro Leu Thr
1               5

<210> SEQ ID NO 55
<211> LENGTH: 11
<212> TYPE: PRT
<213> ORGANISM: Artificial Sequence
<220> FEATURE:
<223> OTHER INFORMATION: Synthetic: Anti-STEAP-1 HVR-H1

<400> SEQUENCE: 55

Gly Tyr Ser Ile Thr Ser Asp Tyr Ala Trp Asn
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Synthetic: Anti-STEAP-1 HVR-H2

<400> SEQUENCE: 56

Gly Tyr Ile Ser Asn Ser Gly Ser Thr Ser Tyr Asn Pro Ser Leu Lys
1               5                   10                  15

Ser

<210> SEQ ID NO 57
<211> LENGTH: 15
<212> TYPE: PRT
<213> ORGANISM: Artificial Sequence
<220> FEATURE:
<223> OTHER INFORMATION: Synthetic: Anti-STEAP-1 HVR-H3
```

```
<400> SEQUENCE: 57

Glu Arg Asn Tyr Asp Tyr Asp Asp Tyr Tyr Ala Met Asp Tyr
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: Synthetic: Anti-STEAP-1 HVR-L1

<400> SEQUENCE: 58

Lys Ser Ser Gln Ser Leu Leu Tyr Arg Ser Asn Gln Lys Asn Tyr Leu
1               5                   10                  15

Ala

<210> SEQ ID NO 59
<211> LENGTH: 7
<212> TYPE: PRT
<213> ORGANISM: Artificial Sequence
<220> FEATURE:
<223> OTHER INFORMATION: Synthetic: Anti-STEAP-1 HVR-L2

<400> SEQUENCE: 59

Trp Ala Ser Thr Arg Glu Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic: Anti-STEAP-1 HVR-L3

<400> SEQUENCE: 60

Gln Gln Tyr Tyr Asn Tyr Pro Arg Thr
1               5

<210> SEQ ID NO 61
<211> LENGTH: 124
<212> TYPE: PRT
<213> ORGANISM: Artificial Sequence
<220> FEATURE:
<223> OTHER INFORMATION: Synthetic: Anti-STEAP1 heavy chain variable
      region

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Asp Asp Tyr Tyr Ala Met Asp
            100                 105                 110

Tyr Trp Gly Gln Gly Thr Leu Val Thr Val Ser Ser
```

<210> SEQ ID NO 62
<211> LENGTH: 113
<212> TYPE: PRT
<213> ORGANISM: Artificial Sequence
<220> FEATURE:
<223> OTHER INFORMATION: Synthetic: Anti-STEAP1 light chain variable
      region

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys Val Glu Ile
            100                 105                 110

Lys

<210> SEQ ID NO 63
<211> LENGTH: 112
<212> TYPE: PRT
<213> ORGANISM: Artificial Sequence
<220> FEATURE:
<223> OTHER INFORMATION: Synthetic: Humanized 7C2.v2.2.LA (hu7C2) light
      chain variable region

<400> SEQUENCE: 63

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

<210> SEQ ID NO 64
<211> LENGTH: 118
<212> TYPE: PRT
<213> ORGANISM: Artificial Sequence
<220> FEATURE:
<223> OTHER INFORMATION: Synthetic: Hu7C2 heavy chain variable region

<400> SEQUENCE: 64

Glu Val Gln Leu Val Gln Ser Gly Ala Glu Val Lys Lys Pro Gly Ala

```
                1               5                  10                  15
            Ser Val Lys Val Ser Cys Lys Ala Ser Gly Tyr Ser Phe Thr Gly Tyr
                            20                  25                  30

Trp Met Asn Trp Val Arg Gln Ala Pro Gly Gln Gly Leu Glu Trp Ile
                        35                  40                  45

Gly Met Ile His Pro Leu Asp Ala Glu Ile Arg Ala Asn Gln Lys Phe
                    50                  55                  60

Arg Asp Arg Val Thr Ile Thr Val Asp Thr Ser Thr Ser Thr Ala Tyr
            65                  70                  75                  80

Leu Glu Leu Ser Ser Leu Arg Ser Glu Asp Thr Ala Val Tyr Tyr Cys
                            85                  90                  95

Ala Arg Gly Thr Tyr Asp Gly Gly Phe Glu Tyr Trp Gly Gln Gly Thr
                            100                 105                 110

Leu Val Thr Val Ser Ser
                    115

<210> SEQ ID NO 65
<211> LENGTH: 15
<212> TYPE: PRT
<213> ORGANISM: Artificial Sequence
<220> FEATURE:
<223> OTHER INFORMATION: Synthetic: Hu7C2 HVR-L1

<400> SEQUENCE: 65

Arg Ala Ser Gln Ser Val Ser Gly Ser Arg Phe Thr Tyr Met His
1               5                   10                  15

<210> SEQ ID NO 66
<211> LENGTH: 7
<212> TYPE: PRT
<213> ORGANISM: Artificial Sequence
<220> FEATURE:
<223> OTHER INFORMATION: Synthetic: Hu7C2 HVR-L2

<400> SEQUENCE: 66

Tyr Ala Ser Ile Leu Glu Ser
1               5

<210> SEQ ID NO 67
<211> LENGTH: 10
<212> TYPE: PRT
<213> ORGANISM: Artificial Sequence
<220> FEATURE:
<223> OTHER INFORMATION: Synthetic: Hu7C2 HVR-L3

<400> SEQUENCE: 67

Gln His Ser Trp Glu Ile Pro Pro Trp Thr
1               5                   10

<210> SEQ ID NO 68
<211> LENGTH: 5
<212> TYPE: PRT
<213> ORGANISM: Artificial Sequence
<220> FEATURE:
<223> OTHER INFORMATION: Synthetic: Hu7C2 HVR-H1

<400> SEQUENCE: 68

Gly Tyr Trp Met Asn
1               5

<210> SEQ ID NO 69
<211> LENGTH: 17
<212> TYPE: PRT
```

```
<213> ORGANISM: Artificial Sequence
<220> FEATURE:
<223> OTHER INFORMATION: Synthetic: Hu7C2 HVR-H2 (Hu7C2.v2.1.S53L,
      S55A HVR-H2)

<400> SEQUENCE: 69

Met Ile His Pro Leu Asp Ala Glu Ile Arg Ala Asn Gln Lys Phe Arg
1               5                   10                  15

Asp

<210> SEQ ID NO 70
<211> LENGTH: 9
<212> TYPE: PRT
<213> ORGANISM: Artificial Sequence
<220> FEATURE:
<223> OTHER INFORMATION: Synthetic: Hu7C2 HVR-H3

<400> SEQUENCE: 70

Gly Thr Tyr Asp Gly Gly Phe Glu Tyr
1               5

<210> SEQ ID NO 71
<211> LENGTH: 219
<212> TYPE: PRT
<213> ORGANISM: Artificial Sequence
<220> FEATURE:
<223> OTHER INFORMATION: Synthetic: Humanized 7C2.v2.2.LA (hu7C2) K149C
      kappa light chain

<400> SEQUENCE: 71

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
                20                  25                  30

Arg Phe Thr Tyr Met His Trp Tyr Gln Gln Lys Pro Gly Gln Pro Pro
            35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215
```

```
<210> SEQ ID NO 72
<211> LENGTH: 448
<212> TYPE: PRT
<213> ORGANISM: Artificial Sequence
<220> FEATURE:
<223> OTHER INFORMATION: Synthetic: Hu7C2 IgG1 heavy chain

<400> SEQUENCE: 72
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Ser | Phe | Thr | Gly | Tyr |
| | | | 20 | | | | | 25 | | | | | 30 | | |
| Trp | Met | Asn | Trp | Val | Arg | Gln | Ala | Pro | Gly | Gln | Gly | Leu | Glu | Trp | Ile |
| | | 35 | | | | | 40 | | | | | 45 | | | |
| Gly | Met | Ile | His | Pro | Leu | Asp | Ala | Glu | Ile | Arg | Ala | Asn | Gln | Lys | Phe |
| 50 | | | | | 55 | | | | | 60 | | | | | |
| Arg | Asp | Arg | Val | Thr | Ile | Thr | Val | Asp | Thr | Ser | Ser | Thr | Ala | Tyr | |
| 65 | | | | 70 | | | | | 75 | | | | | 80 | |
| Leu | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Thr | Tyr | Asp | Gly | Gly | Phe | Glu | Tyr | Trp | Gly | Gln | Gly | Thr |
| | | | 100 | | | | | 105 | | | | | 110 | | |
| Leu | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| | 130 | | | | | 135 | | | | | 140 | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | 195 | | | | | 200 | | | | | 205 | | | |
| Asn | Thr | Lys | Val | Asp | Lys | Lys | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | 275 | | | | | 280 | | | | | 285 | | | |
| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Glu | Glu | Met | Thr | Lys | Asn | Gln | Val | Ser | Leu | Thr | Cys |
| | | 355 | | | | | 360 | | | | | 365 | | | |
| Leu | Val | Lys | Gly | Phe | Tyr | Pro | Ser | Asp | Ile | Ala | Val | Glu | Trp | Glu | Ser |

-continued

```
                370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 73
<211> LENGTH: 17
<212> TYPE: PRT
<213> ORGANISM: Artificial Sequence
<220> FEATURE:
<223> OTHER INFORMATION: Synthetic: Hu7C2.v2.1.S53M HVR-H2

<400> SEQUENCE: 73

```
Met Ile His Pro Met Asp Ser Glu Ile Arg Ala Asn Gln Lys Phe Arg
1               5                   10                  15

Asp
```

<210> SEQ ID NO 74
<211> LENGTH: 17
<212> TYPE: PRT
<213> ORGANISM: Artificial Sequence
<220> FEATURE:
<223> OTHER INFORMATION: Synthetic: Hu7C2.v2.1.S53L HVR-H2

<400> SEQUENCE: 74

```
Met Ile His Pro Leu Asp Ser Glu Ile Arg Ala Asn Gln Lys Phe Arg
1               5                   10                  15

Asp
```

<210> SEQ ID NO 75
<211> LENGTH: 9
<212> TYPE: PRT
<213> ORGANISM: Artificial Sequence
<220> FEATURE:
<223> OTHER INFORMATION: Synthetic: Hu7C2.v2.1.E101K HVR-H3

<400> SEQUENCE: 75

```
Gly Thr Tyr Asp Gly Gly Phe Lys Tyr
1               5
```

<210> SEQ ID NO 76
<211> LENGTH: 106
<212> TYPE: PRT
<213> ORGANISM: Artificial Sequence
<220> FEATURE:
<223> OTHER INFORMATION: Synthetic: V205C cysteine engineered light
    chain constant region (IgK)

<400> SEQUENCE: 76

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60
```

```
Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Cys Thr Lys Ser Phe Asn Arg Gly Glu Cys
            100                 105

<210> SEQ ID NO 77
<211> LENGTH: 330
<212> TYPE: PRT
<213> ORGANISM: Artificial Sequence
<220> FEATURE:
<223> OTHER INFORMATION: Synthetic: A118C cysteine engineered heavy
      chain constant region (IgG1)

<400> SEQUENCE: 77

Cys Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

```
                    305                 310                 315                 320
Gln Lys Ser Leu Ser Leu Ser Pro Gly Lys
                325                 330

<210> SEQ ID NO 78
<211> LENGTH: 106
<212> TYPE: PRT
<213> ORGANISM: Artificial Sequence
<220> FEATURE:
<223> OTHER INFORMATION: Synthetic: K149C cysteine engineered light
      chain constant region (IgK)

<400> SEQUENCE: 78

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Cys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 79
<211> LENGTH: 330
<212> TYPE: PRT
<213> ORGANISM: Artificial Sequence
<220> FEATURE:
<223> OTHER INFORMATION: Synthetic: S400C cysteine engineered heavy
      chain constant region (IgG1)

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Cys Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 80
<211> LENGTH: 10
<212> TYPE: PRT
<213> ORGANISM: Artificial Sequence
<220> FEATURE:
<223> OTHER INFORMATION: Synthetic: Anti-HER2 HVR-H1

<400> SEQUENCE: 80

Gly Phe Asn Ile Lys Asp Thr Tyr Ile His
1               5                   10

<210> SEQ ID NO 81
<211> LENGTH: 17
<212> TYPE: PRT
<213> ORGANISM: Artificial Sequence
<220> FEATURE:
<223> OTHER INFORMATION: Synthetic: Anti-HER2 HVR-H2

<400> SEQUENCE: 81

Arg Ile Tyr Pro Thr Asn Gly Tyr Thr Arg Tyr Ala Asp Ser Val Lys
1               5                   10                  15

Gly

<210> SEQ ID NO 82
<211> LENGTH: 10
<212> TYPE: PRT
<213> ORGANISM: Artificial Sequence
<220> FEATURE:
<223> OTHER INFORMATION: Synthetic: Anti-HER2 HVR-H3
```

```
<400> SEQUENCE: 82

Trp Gly Gly Asp Gly Phe Tyr Ala Met Asp
1               5                   10

<210> SEQ ID NO 83
<211> LENGTH: 15
<212> TYPE: PRT
<213> ORGANISM: Artificial Sequence
<220> FEATURE:
<223> OTHER INFORMATION: Synthetic: Anti-HER2 HVR-L1

<400> SEQUENCE: 83

Ile Thr Cys Arg Ala Ser Gln Asp Val Asn Thr Ala Val Ala Trp
1               5                   10                  15

<210> SEQ ID NO 84
<211> LENGTH: 7
<212> TYPE: PRT
<213> ORGANISM: Artificial Sequence
<220> FEATURE:
<223> OTHER INFORMATION: Synthetic: Anti-HER2 HVR-L2

<400> SEQUENCE: 84

Ser Ala Ser Phe Leu Tyr Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic: Anti-HER2 HVR-L3

<400> SEQUENCE: 85

Gln Gln His Tyr Thr Thr Pro Pro Thr
1               5
```

ANTIBODIES AND IMMUNOCONJUGATES

CROSS-REFERENCE TO RELATED APPLICATIONS

The present application claims the benefit of priority to U.S. Provisional Application No. 62/175,802, filed Jun. 15, 2015, which is incorporated by reference herein in its entirety for any purpose.

SEQUENCE LISTING

The present application is filed with a Sequence Listing in electronic format. The Sequence Listing is provided as a file entitled "2016-06-14_01146-0044-00US_ST25_final.txt" created on Jun. 12, 2016, which is 59,620 bytes in size. The information in the electronic format of the sequence listing is incorporated herein by reference in its entirety.

FIELD OF THE INVENTION

The present invention relates to antibodies and immunoconjugates and methods of using the same.

BACKGROUND

The use of monoclonal antibodies (mABs) to deliver anticancer drugs directly to tumor cells has attracted a great deal of focus in recent years. Two new antibody-drug conjugates have been approved by the FDA for the treatment of cancer. Adcetris® (brentuximab vedotin) is a CD30-directed antibody-drug conjugate (ADC) indicated for the treatment of relapsed or refractory Hodgkin lymphoma and systemic anaplastic large cell lymphoma (ALCL). Kadcyla® (ado-trastuzumab emtansine), is a new therapy approved for patients with HER2-positive, late-stage (metastatic) breast cancer. To obtain a therapeutic both potent anti-tumor activity and acceptable therapeutic index in an ADC, several aspects of design may be optimized. Particularly, it is well known that the chemical structure of the linker can have significant impact on both the efficacy and the safety of ADC (Ducry & Stump, Bioconjugate Chem, 2010, 21, 5-13). Choosing the right linker influences proper drug delivery to the intended cellular compartment of cancer cells. Linkers can be generally divided into two categories: cleavable (such as peptide, hydrzone, or disulfide) or non-cleavable (such as thioether). Peptide linkers, such as Valine-Citrulline (Val-Cit), that can be hydrolyzed by lysosomal enzymes (such as Cathepsin B) have been used to connect the drug with the antibody (U.S. Pat. No. 6,214,345). They have been particularly useful, due in part to their relative stability in systemic circulation and the ability to efficiently release the drug in tumor. ADCs containing the Val-Cit linker have been shown to be relatively stable in vivo ($t_{1/2}$ for drug release is ~7 days (Doronina et al (2008), Bioconjugate Chem., 19, 1960-1963)). However, the chemical space represented by natural peptides is limited; therefore, it is desirable to have a variety of non-peptide linkers which act like peptides and can be effectively cleaved by lysosomal proteases. The greater diversity of non-peptide structures may yield novel, beneficial properties that are not afforded by the peptide linkers. Provided herein are different types of non-peptide linkers for ADC that can be cleaved by lysosomal enzymes.

There is a need in the art for agents that target antigens for the diagnosis and treatment of certain conditions, such as cancer. The invention fulfills that need and provides other benefits.

SUMMARY

In various embodiments, the invention provides immunoconjugates and methods of using the same.

In some embodiments, an immunoconjugates is provided, comprising a structure selected from:

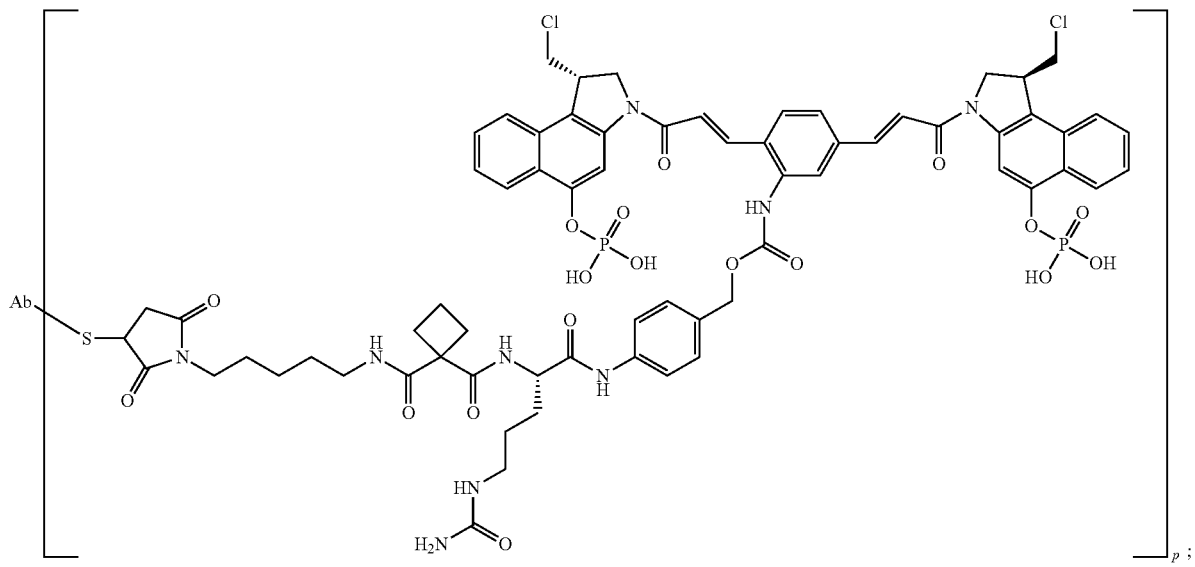

-continued

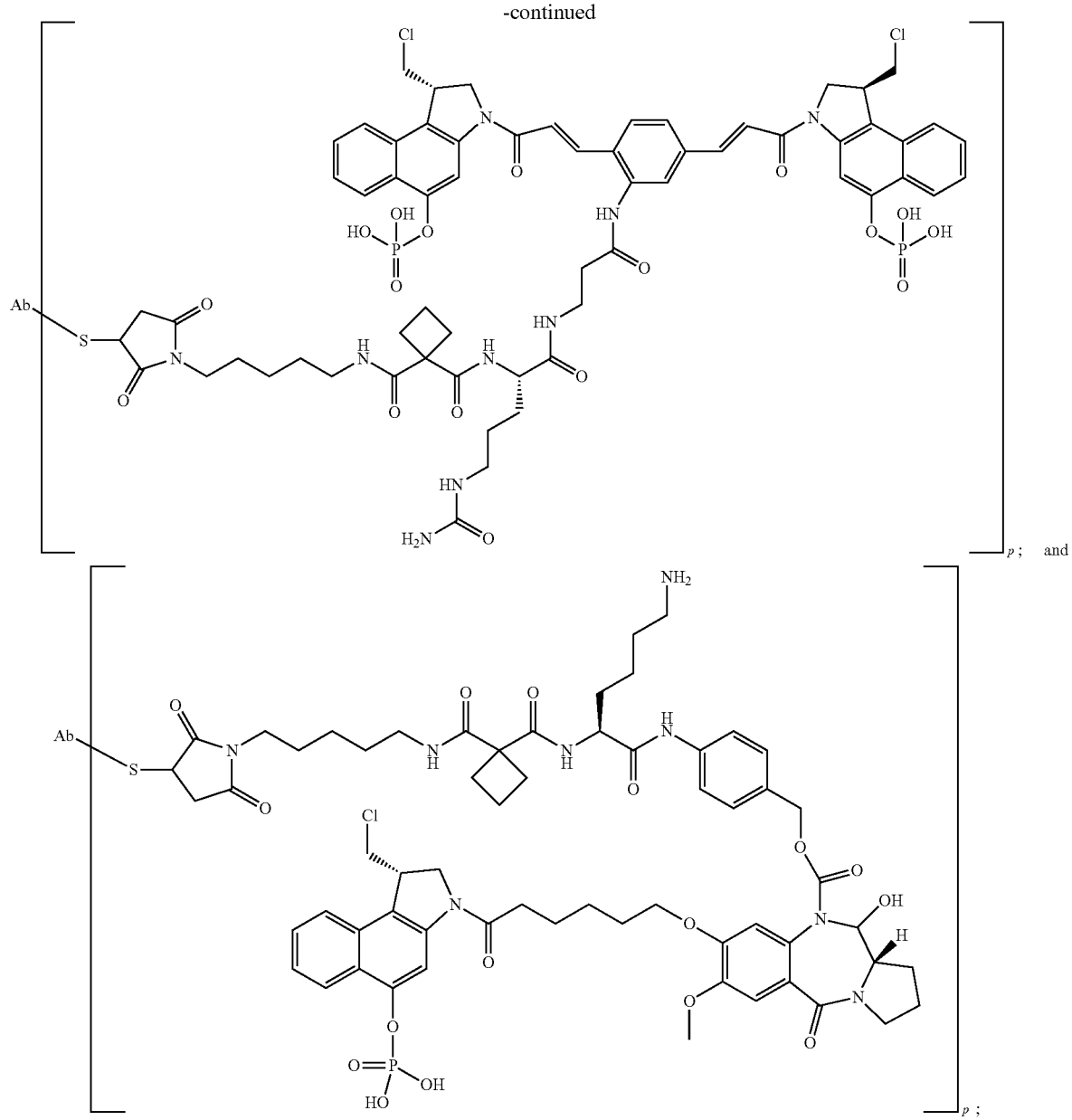

wherein p is from 1 to 4 and Ab is an antibody selected from:
a) an antibody comprising an HVR-H1 comprising the amino acid sequence of SEQ ID NO: 6, and an HVR-H2 comprising the amino acid sequence of SEQ ID NO: 7; an HVR-H3 comprising the amino acid sequence of SEQ ID NO: 8; an HVR-L1 comprising the amino acid sequence of SEQ ID NO: 3; an HVR-L2 comprising the amino acid sequence of SEQ ID NO: 4; and an HVR-L3 comprising the amino acid sequence of SEQ ID NO: 5;
b) an antibody comprising an HVR-H1 comprising the amino acid sequence of SEQ ID NO: 49, and an HVR-H2 comprising the amino acid sequence of SEQ ID NO: 50; an HVR-H3 comprising the amino acid sequence of SEQ ID NO: 51; an HVR-L1 comprising the amino acid sequence of SEQ ID NO: 52; an HVR-L2 comprising the amino acid sequence of SEQ ID NO: 53; and an HVR-L3 comprising the amino acid sequence of SEQ ID NO: 54;
c) an antibody comprising an HVR-H1 comprising the amino acid sequence of SEQ ID NO: 18, and an HVR-H2 comprising the amino acid sequence of SEQ ID NO: 19; an HVR-H3 comprising the amino acid sequence of SEQ ID NO: 20; an HVR-L1 comprising the amino acid sequence of SEQ ID NO: 15; an HVR-L2 comprising the amino acid sequence of SEQ ID NO: 16; and an HVR-L3 comprising the amino acid sequence of SEQ ID NO: 17;
d) an antibody comprising an HVR-H1 comprising the amino acid sequence of SEQ ID NO: 26, and an HVR-H2 comprising the amino acid sequence of SEQ ID NO: 27; an HVR-H3 comprising the amino acid sequence of SEQ ID NO: 28; an HVR-L1 comprising the amino acid sequence of SEQ ID NO: 23; an HVR-L2 comprising the amino acid sequence of SEQ ID NO: 24; and an HVR-L3 comprising the amino acid sequence of SEQ ID NO: 25;

e) an antibody comprising an HVR-H1 comprising the amino acid sequence of SEQ ID NO: 34, and an HVR-H2 comprising the amino acid sequence of SEQ ID NO: 35; an HVR-H3 comprising the amino acid sequence of SEQ ID NO: 36; an HVR-L1 comprising the amino acid sequence of SEQ ID NO: 31; an HVR-L2 comprising the amino acid sequence of SEQ ID NO: 32; and an HVR-L3 comprising the amino acid sequence of SEQ ID NO: 33;

f) an antibody comprising an HVR-H1 comprising the amino acid sequence of SEQ ID NO: 42, and an HVR-H2 comprising the amino acid sequence of SEQ ID NO: 43; an HVR-H3 comprising the amino acid sequence of SEQ ID NO: 44; an HVR-L1 comprising the amino acid sequence of SEQ ID NO: 39; an HVR-L2 comprising the amino acid sequence of SEQ ID NO: 40; and an HVR-L3 comprising the amino acid sequence of SEQ ID NO: 41;

g) an antibody comprising an HVR-H1 comprising the amino acid sequence of SEQ ID NO: 55, and an HVR-H2 comprising the amino acid sequence of SEQ ID NO: 56; an HVR-H3 comprising the amino acid sequence of SEQ ID NO: 57; an HVR-L1 comprising the amino acid sequence of SEQ ID NO: 58; an HVR-L2 comprising the amino acid sequence of SEQ ID NO: 59; and an HVR-L3 comprising the amino acid sequence of SEQ ID NO: 60;

h) an antibody comprising an HVR-H1 comprising the amino acid sequence of SEQ ID NO: 68, and an HVR-H2 comprising the amino acid sequence of SEQ ID NO: 69, 73, or 74; an HVR-H3 comprising the amino acid sequence of SEQ ID NO: 70 or 75; an HVR-L1 comprising the amino acid sequence of SEQ ID NO: 65; an HVR-L2 comprising the amino acid sequence of SEQ ID NO: 66; and an HVR-L3 comprising the amino acid sequence of SEQ ID NO: 67;

i) an antibody comprising an HVR-H1 comprising the amino acid sequence of SEQ ID NO: 68, and an HVR-H2 comprising the amino acid sequence of SEQ ID NO: 69; an HVR-H3 comprising the amino acid sequence of SEQ ID NO: 70; an HVR-L1 comprising the amino acid sequence of SEQ ID NO: 65; an HVR-L2 comprising the amino acid sequence of SEQ ID NO: 66; and an HVR-L3 comprising the amino acid sequence of SEQ ID NO: 67; and j) an antibody comprising an HVR-H1 comprising the amino acid sequence of SEQ ID NO: 80, and an HVR-H2 comprising the amino acid sequence of SEQ ID NO: 81; an HVR-H3 comprising the amino acid sequence of SEQ ID NO: 82; an HVR-L1 comprising the amino acid sequence of SEQ ID NO: 83; an HVR-L2 comprising the amino acid sequence of SEQ ID NO: 84; and an HVR-L3 comprising the amino acid sequence of SEQ ID NO: 85.

In some embodiments, Ab is an antibody selected from:

a) an antibody comprising a heavy chain variable region comprising the amino acid sequence of SEQ ID NO: 2 and a light chain variable region comprising the amino acid sequence of SEQ ID NO: 1;

b) an antibody comprising a heavy chain variable region comprising the amino acid sequence of SEQ ID NO: 47 and a light chain variable region comprising the amino acid sequence of SEQ ID NO: 48;

c) an antibody comprising a heavy chain variable region comprising the amino acid sequence of SEQ ID NO: 22 and a light chain variable region comprising the amino acid sequence of SEQ ID NO: 21;

d) an antibody comprising a heavy chain variable region comprising the amino acid sequence of SEQ ID NO: 30 and a light chain variable region comprising the amino acid sequence of SEQ ID NO: 29;

e) an antibody comprising a heavy chain variable region comprising the amino acid sequence of SEQ ID NO: 38 and a light chain variable region comprising the amino acid sequence of SEQ ID NO: 37;

f) an antibody comprising a heavy chain variable region comprising the amino acid sequence of SEQ ID NO: 46 and a light chain variable region comprising the amino acid sequence of SEQ ID NO: 45;

g) an antibody comprising a heavy chain variable region comprising the amino acid sequence of SEQ ID NO: 61 and a light chain variable region comprising the amino acid sequence of SEQ ID NO: 62;

h) an antibody comprising a heavy chain variable region comprising the amino acid sequence of SEQ ID NO: 64 and a light chain variable region comprising the amino acid sequence of SEQ ID NO: 63; and i) an antibody comprising a heavy chain variable region comprising the amino acid sequence of SEQ ID NO: 14 and a light chain variable region comprising the amino acid sequence of SEQ ID NO: 12.

In some embodiments, Ab is an antibody that binds Ly6E, wherein the antibody comprises:

a) an HVR-H1 comprising the amino acid sequence of SEQ ID NO: 6, and an HVR-H2 comprising the amino acid sequence of SEQ ID NO: 7; an HVR-H3 comprising the amino acid sequence of SEQ ID NO: 8; an HVR-L1 comprising the amino acid sequence of SEQ ID NO: 3; an HVR-L2 comprising the amino acid sequence of SEQ ID NO: 4; and an HVR-L3 comprising the amino acid sequence of SEQ ID NO: 5; or b) a heavy chain variable region comprising the amino acid sequence of SEQ ID NO: 2 and a light chain variable region comprising the amino acid sequence of SEQ ID NO: 1.

In some embodiments, Ab is an antibody that binds CD79b, wherein the antibody comprises:

a) an HVR-H1 comprising the amino acid sequence of SEQ ID NO: 49, and an HVR-H2 comprising the amino acid sequence of SEQ ID NO: 50; an HVR-H3 comprising the amino acid sequence of SEQ ID NO: 51; an HVR-L1 comprising the amino acid sequence of SEQ ID NO: 52; an HVR-L2 comprising the amino acid sequence of SEQ ID NO: 53; and an HVR-L3 comprising the amino acid sequence of SEQ ID NO: 54; or b) a heavy chain variable region comprising the amino acid sequence of SEQ ID NO: 47 and a light chain variable region comprising the amino acid sequence of SEQ ID NO: 48.

In some embodiments, Ab is an antibody that binds MUC16, wherein the antibody comprises:

a) an HVR-H1 comprising the amino acid sequence of SEQ ID NO: 18, and an HVR-H2 comprising the amino acid sequence of SEQ ID NO: 19; an HVR-H3 comprising the amino acid sequence of SEQ ID NO: 20; an HVR-L1 comprising the amino acid sequence of SEQ ID NO: 15; an HVR-L2 comprising the amino acid sequence of SEQ ID NO: 16; and an HVR-L3 comprising the amino acid sequence of SEQ ID NO: 17;

b) an HVR-H1 comprising the amino acid sequence of SEQ ID NO: 26, and an HVR-H2 comprising the amino acid sequence of SEQ ID NO: 27; an HVR-H3 comprising the amino acid sequence of SEQ ID NO: 28; an HVR-L1 comprising the amino acid sequence of SEQ ID NO: 23; an HVR-L2 comprising the amino acid sequence of SEQ ID NO: 24; and an HVR-L3 comprising the amino acid sequence of SEQ ID NO: 25;
c) an HVR-H1 comprising the amino acid sequence of SEQ ID NO: 34, and an HVR-H2 comprising the amino acid sequence of SEQ ID NO: 35; an HVR-H3 comprising the amino acid sequence of SEQ ID NO: 36; an HVR-L1 comprising the amino acid sequence of SEQ ID NO: 31; an HVR-L2 comprising the amino acid sequence of SEQ ID NO: 32; and an HVR-L3 comprising the amino acid sequence of SEQ ID NO: 33;
d) an HVR-H1 comprising the amino acid sequence of SEQ ID NO: 42, and an HVR-H2 comprising the amino acid sequence of SEQ ID NO: 43; an HVR-H3 comprising the amino acid sequence of SEQ ID NO: 44; an HVR-L1 comprising the amino acid sequence of SEQ ID NO: 39; an HVR-L2 comprising the amino acid sequence of SEQ ID NO: 40; and an HVR-L3 comprising the amino acid sequence of SEQ ID NO: 41;
e) a heavy chain variable region comprising the amino acid sequence of SEQ ID NO: 22 and a light chain variable region comprising the amino acid sequence of SEQ ID NO: 21;
f) a heavy chain variable region comprising the amino acid sequence of SEQ ID NO: 30 and a light chain variable region comprising the amino acid sequence of SEQ ID NO: 29;
g) a heavy chain variable region comprising the amino acid sequence of SEQ ID NO: 38 and a light chain variable region comprising the amino acid sequence of SEQ ID NO: 37;
h) a heavy chain variable region comprising the amino acid sequence of SEQ ID NO: 46 and a light chain variable region comprising the amino acid sequence of SEQ ID NO: 45;

In some embodiments, Ab is an antibody that binds STEAP1, wherein the antibody comprises:
a) an HVR-H1 comprising the amino acid sequence of SEQ ID NO: 55, and an HVR-H2 comprising the amino acid sequence of SEQ ID NO: 56; an HVR-H3 comprising the amino acid sequence of SEQ ID NO: 57; an HVR-L1 comprising the amino acid sequence of SEQ ID NO: 58; an HVR-L2 comprising the amino acid sequence of SEQ ID NO: 59; and an HVR-L3 comprising the amino acid sequence of SEQ ID NO: 60;
b) a heavy chain variable region comprising the amino acid sequence of SEQ ID NO: 61 and a light chain variable region comprising the amino acid sequence of SEQ ID NO: 62.

In some embodiments, Ab is an antibody that binds HER2, wherein the antibody comprises:
a) an HVR-H1 comprising the amino acid sequence of SEQ ID NO: 68, and an HVR-H2 comprising the amino acid sequence of SEQ ID NO: 69, 73, or 74; an HVR-H3 comprising the amino acid sequence of SEQ ID NO: 70 or 75; an HVR-L1 comprising the amino acid sequence of SEQ ID NO: 65; an HVR-L2 comprising the amino acid sequence of SEQ ID NO: 66; and an HVR-L3 comprising the amino acid sequence of SEQ ID NO: 67;
b) an HVR-H1 comprising the amino acid sequence of SEQ ID NO: 68, and an HVR-H2 comprising the amino acid sequence of SEQ ID NO: 69; an HVR-H3 comprising the amino acid sequence of SEQ ID NO: 70; an HVR-L1 comprising the amino acid sequence of SEQ ID NO: 65; an HVR-L2 comprising the amino acid sequence of SEQ ID NO: 66; and an HVR-L3 comprising the amino acid sequence of SEQ ID NO: 67;
c) an HVR-H1 comprising the amino acid sequence of SEQ ID NO: 80, and an HVR-H2 comprising the amino acid sequence of SEQ ID NO: 81; an HVR-H3 comprising the amino acid sequence of SEQ ID NO: 82; an HVR-L1 comprising the amino acid sequence of SEQ ID NO: 83; an HVR-L2 comprising the amino acid sequence of SEQ ID NO: 84; and an HVR-L3 comprising the amino acid sequence of SEQ ID NO: 85;
d) a heavy chain variable region comprising the amino acid sequence of SEQ ID NO: 64 and a light chain variable region comprising the amino acid sequence of SEQ ID NO: 63; or
e) a heavy chain variable region comprising the amino acid sequence of SEQ ID NO: 14 and a light chain variable region comprising the amino acid sequence of SEQ ID NO: 12.

In any of the embodiments provided herein, p may range from 1 to 4. In any of the embodiments provided herein, p may be about 2.

In some embodiments, the antibody is a monoclonal antibody. In some embodiments, the antibody is a humanized or chimeric antibody. In some embodiments, the antibody is an antibody fragment that binds to antigen. In some embodiments, the antibody is an IgG1, IgG2a or IgG2b antibody. In some embodiments, the antibody comprises at least one mutation in the heavy chain constant region selected from A118C and S400C. In some embodiments, the antibody comprises a heavy chain constant region comprising the amino acid sequence of SEQ ID NO: 77 or 79. In some embodiments, the antibody comprises at least one mutation in the light chain constant region selected from K149C and V205C. In some embodiments, the antibody comprises a light chain constant region comprising the amino acid sequence of SEQ ID NO: 76 or 78. In some embodiments, the antibody comprises a K149C mutation in the light chain constant region. In some embodiments, the light chain constant region comprises the amino acid sequence of SEQ ID NO: 78.

In some embodiments, an immunoconjugates is provided, wherein the antibody comprises:
a) a heavy chain comprising the sequence of SEQ ID NO: 10 and a light chain comprising the sequence of SEQ ID NO: 9; or
b) a heavy chain comprising the sequence of SEQ ID NO: 72 and a light chain comprising the sequence of SEQ ID NO: 71.

In some embodiments, a pharmaceutical formulation is provided, comprising an immunoconjugate provided herein and a pharmaceutically acceptable carrier.

In some embodiments, a method of treating cancer is provided, comprising administering to an individual with cancer an effective amount of an immunoconjugate described herein or a pharmaceutical formulation comprising an immunoconjugates described herein.

In some embodiments, the cancer is a Ly6E-positive cancer. In some embodiments, the immunoconjugate comprises an antibody that binds Ly6E. In some embodiments, the cancer is selected from breast cancer, metastatic breast cancer, Her2 negative breast cancer, triple negative breast cancer, pancreatic cancer, colon cancer, colorectal cancer, melanoma, ovarian cancer, non-small cell lung cancer, and gastric cancer.

In some embodiments, the cancer is a CD79b-positive cancer. In some embodiments, the immunoconjugate comprises an antibody that binds CD79b. In some embodiments, the cancer is selected from lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), Burkitt's lymphoma, and mantle cell lymphoma.

In some embodiments, the cancer is a MUC16-positive cancer. In some embodiments, the immunoconjugate comprises an antibody that binds MUC16. In some embodiments, the cancer is selected from ovarian cancer, endometrial cancer, non-small cell lung cancer, pancreatic cancer, breast cancer, metastatic breast cancer, Her2 negative breast cancer, and triple negative breast cancer.

In some embodiments, the cancer is a STEAP1-positive cancer. In some embodiments, the immunoconjugate comprises an antibody that binds STEAP1. In some embodiments, the cancer is selected from prostate cancer, lung cancer, colon cancer, bladder cancer, ovarian cancer, or Ewing's sarcoma.

In some embodiments, the cancer is a HER2-positive cancer. In some embodiments, the immunoconjugate comprises an antibody that binds HER2. In some embodiments, the cancer is selected from breast cancer and gastric cancer.

In some embodiments, a method of inhibiting proliferation of a cell is provided, comprising exposing the cell to an immunoconjugate described herein under conditions permissive for binding of the immunoconjugate to an antigen on the surface of the cell, thereby inhibiting proliferation of the cell. In some embodiments, the antigen is selected from Ly6E, CD79b, MUC16, STEAP1, and HER2.

In some embodiments, an immunoconjugate described herein is provided for treating cancer. In some embodiments, use of an immunoconjugate described herein for preparation of a medicament for treating cancer is provided.

DETAILED DESCRIPTION

Figure 1:
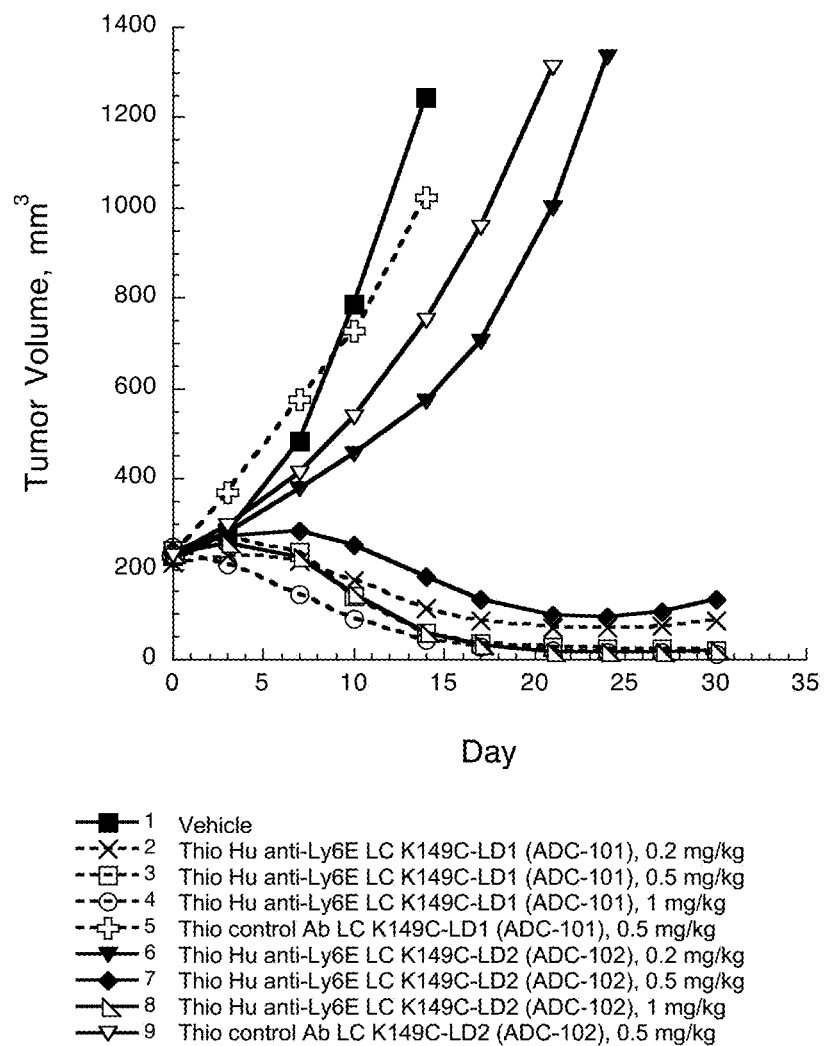
FIG. 1 shows change in tumor volume ($mm^3$) over time in a mouse HCC1569X2 xenograft model upon treatment with anti-Ly6E immunoconjugates, as described in Example 2.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described.

All references cited throughout the disclosure are expressly incorporated by reference herein in their entirety. In the event that one or more of the incorporated literature, patents, and similar materials differs from or contradicts this application, including but not limited to defined terms, term usage, described techniques, or the like, this application controls.

I. Definitions

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd) Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Ly6E antibody" and "an antibody that binds to Ly6E" refer to an antibody that is capable of binding Ly6E with sufficient affinity such that the antibody is useful as a diagnostic and/or therapeutic agent in targeting Ly6E. In one embodiment, the extent of binding of an anti-Ly6E antibody to an unrelated, non-Ly6E protein is less than about 10% of the binding of the antibody to Ly6E as measured, e.g., by a radioimmunoassay (RIA). In certain embodiments, an antibody that binds to Ly6E has a dissociation constant (Kd) of ≤1 µM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$ M). In certain embodiments, an anti-Ly6E antibody binds to an epitope of Ly6E that is conserved among Ly6E from different species.

The terms "anti-STEAP1 antibody" and "an antibody that binds to STEAP1" refer to an antibody that is capable of binding STEAP1 with sufficient affinity such that the antibody is useful as a diagnostic and/or therapeutic agent in targeting STEAP1. In one embodiment, the extent of binding of an anti-STEAP1 antibody to an unrelated, non-STEAP1 protein is less than about 10% of the binding of the antibody to STEAP1 as measured, e.g., by a radioimmunoassay (RIA). In certain embodiments, an antibody that binds to STEAP1 has a dissociation constant (Kd) of ≤1 µM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$M to $10^{-13}$M, e.g., from $10^{-9}$M to $10^{-13}$ M). In certain embodiments, an anti-STEAP1 antibody binds to an epitope of STEAP1 that is conserved among STEAP1 from different species.

The terms "anti-CD79b antibody" and "an antibody that binds to CD79b" refer to an antibody that is capable of binding CD79b with sufficient affinity such that the antibody is useful as a diagnostic and/or therapeutic agent in targeting CD79b. In one embodiment, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant (Kd) of ≤1 µM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$ M). In certain embodiments, an anti-CD79b antibody binds to an epitope of CD79b that is conserved among CD79b from different species.

The terms "anti-MUC16 antibody" and "an antibody that binds to MUC16" refer to an antibody that is capable of binding MUC16 with sufficient affinity such that the antibody is useful as a diagnostic and/or therapeutic agent in targeting MUC16. In one embodiment, the extent of binding of an anti-MUC16 antibody to an unrelated, non-MUC16 protein is less than about 10% of the binding of the antibody to MUC16 as measured, e.g., by a radioimmunoassay (RIA). In certain embodiments, an antibody that binds to MUC16 has a dissociation constant (Kd) of ≤1 µM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$ M). In certain embodiments, an anti-MUC16 antibody binds to an epitope of MUC16 that is conserved among MUC16 from different species.

The terms "anti-HER2 antibody" and "an antibody that binds to HER2" refer to an antibody that is capable of binding HER2 with sufficient affinity such that the antibody is useful as a diagnostic and/or therapeutic agent in targeting HER2. In one embodiment, the extent of binding of an anti-HER2 antibody to an unrelated, non-HER2 protein is less than about 10% of the binding of the antibody to HER2 as measured, e.g., by a radioimmunoassay (RIA). In certain embodiments, an antibody that binds to HER2 has a dissociation constant (Kd) of ≤1 µM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$ M). In certain embodiments, an anti-HER2 antibody binds to an epitope of HER2 that is conserved among HER2 from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include a cancer that over-expresses Ly6E, which may include, for example, breast cancer and/or metastatic breast cancer, including Her2 negative breast cancers and/or triple negative breast cancers, pancreatic cancer, colon cancer, colorectal cancer, melanoma, ovarian cancer, non-small cell lung cancer (either squamous and/or non-squamous), gastric cancer, squamous cell cancer, small-cell lung cancer, adenocarcinoma of the lung, squamous carcinoma of the lung, cancer of the peritoneum, hepatocellular cancer, gastrointestinal cancer, glioma, cervical cancer, liver cancer, bladder cancer, hepatoma, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "Ly6E," as used herein, refers to any native, mature Ly6E which results from processing of a Ly6E precursor protein in a cell. The term includes Ly6E from any vertebrate source, including mammals such as primates (e.g. humans and cynomolgus or rhesus monkeys) and rodents (e.g., mice and rats), unless otherwise indicated. The term also includes naturally occurring variants of Ly6E, e.g., splice variants or allelic variants. The amino acid sequence of an exemplary human Ly6E precursor protein, with signal sequence (amino acids 1-20=signal sequence) is shown in UniProtKB/Swiss-Prot Accession No. Q16553.1, dated 27 May 2015. The amino acid sequence of an exemplary mature human Ly6E is amino acids 21 to 101 of UniProtKB/Swiss-Prot Accession No. Q16553.1, dated 27 May 2015.

The term "Ly6E-positive cancer" refers to a cancer comprising cells that express Ly6E on their surface. For the purposes of determining whether a cell expresses Ly6E on the surface, Ly6E mRNA expression is considered to correlate to Ly6E expression on the cell surface. In some embodiments, expression of Ly6E mRNA is determined by a method selected from in situ hybridization and RT-PCR (including quantitative RT-PCR). Alternatively, expression of Ly6E on the cell surface can be determined, for example, using antibodies to Ly6E in a method such as immunohistochemistry, FACS, etc. In some embodiments, a Ly6E-positive cancer is a breast cancer, metastatic breast cancer, including Her2 negative breast cancers and/or triple negative breast cancers, pancreatic cancer, colon cancer, colorectal cancer, melanoma, ovarian cancer, non-small cell lung cancer (either squamous and/or non-squamous), or gastric cancer.

The term "Ly6E-positive cell" refers to a cancer cell that expresses Ly6E on its surface.

The term "STEAP1," as used herein, refers to any native, mature STEAP1 which results from processing of a STEAP1 precursor protein in a cell. The term includes STEAP1 from any vertebrate source, including mammals such as primates (e.g. humans and cynomolgus or rhesus monkeys) and rodents (e.g., mice and rats), unless otherwise indicated. The term also includes naturally occurring variants of STEAP1, e.g., splice variants or allelic variants. The amino acid sequence of an exemplary human STEAP1 protein is shown in UniProtKB/Swiss-Prot Accession No. Q9UHE8.1, dated 27 May 2015.

The term "STEAP1-positive cancer" refers to a cancer comprising cells that express STEAP1 on their surface. For the purposes of determining whether a cell expresses STEAP1 on the surface, STEAP1 mRNA expression is considered to correlate to STEAP1 expression on the cell surface. In some embodiments, expression of STEAP1 mRNA is determined by a method selected from in situ hybridization and RT-PCR (including quantitative RT-PCR). Alternatively, expression of STEAP1 on the cell surface can be determined, for example, using antibodies to STEAP1 in a method such as immunohistochemistry, FACS, etc. In some embodiments, a STEAP1-positive cancer is a prostate cancer, lung cancer, colon cancer, bladder cancer, ovarian cancer, or Ewing's sarcoma.

The term "STEAP1-positive cell" refers to a cancer cell that expresses STEAP1 on its surface.

The term "CD79b," as used herein, refers to any native, mature CD79b which results from processing of a CD79b precursor protein in a cell. The term includes CD79b from any vertebrate source, including mammals such as primates (e.g. humans and cynomolgus or rhesus monkeys) and rodents (e.g., mice and rats), unless otherwise indicated. The term also includes naturally occurring variants of CD79b, e.g., splice variants or allelic variants. The amino acid sequence of an exemplary human CD79b precursor protein, with signal sequence (amino acids 1-28=signal sequence) is shown in NCBI Accession No. NP_000617.1 dated 15 Mar. 2015. The amino acid sequence of an exemplary mature human CD79b is amino acids 29 to 228 of NCBI Accession No. NP_000617.1 dated 15 Mar. 2015.

The term "CD79b-positive cancer" refers to a cancer comprising cells that express CD79b on their surface. For the purposes of determining whether a cell expresses CD79b on the surface, CD79b mRNA expression is considered to correlate to CD79b expression on the cell surface. In some embodiments, expression of CD79b mRNA is determined by a method selected from in situ hybridization and RT-PCR (including quantitative RT-PCR). Alternatively, expression of CD79b on the cell surface can be determined, for example, using antibodies to CD79b in a method such as immunohistochemistry, FACS, etc. In some embodiments, a CD79b-positive disorder or cancer is a B cell disorder and/or a B cell proliferative disorder, such as, but not limited to, lymphoma, non-Hogkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), Burkitt's lymphoma, and mantle cell lymphoma.

The term "CD79b-positive cell" refers to a cancer cell that expresses CD79b on its surface.

The term "MUC16," as used herein, refers to any native, mature MUC16 which results from processing of a MUC16 precursor protein in a cell. The term includes MUC16 from any vertebrate source, including mammals such as primates (e.g. humans and cynomolgus or rhesus monkeys) and rodents (e.g., mice and rats), unless otherwise indicated. The term also includes naturally occurring variants of MUC16, e.g., splice variants or allelic variants. The amino acid sequence of an exemplary human MUC16 protein is shown in UniProtKB/Swiss-Prot: Q8WXI7.2, dated 27 Mar. 2015.

The term "MUC16-positive cancer" refers to a cancer comprising cells that express MUC16 on their surface. For the purposes of determining whether a cell expresses MUC16 on the surface, MUC16 mRNA expression is considered to correlate to MUC16 expression on the cell surface. In some embodiments, expression of MUC16 mRNA is determined by a method selected from in situ hybridization and RT-PCR (including quantitative RT-PCR). Alternatively, expression of MUC16 on the cell surface can be determined, for example, using antibodies to MUC16 in a method such as immunohistochemistry, FACS, etc. In some embodiments, a MUC16-positive cancer is ovarian cancer, endometrial cancer, non-small cell lung cancer (either squamous and/or non-squamous), pancreatic cancer, or breast cancer, such as metastatic breast cancer, including Her2 negative breast cancer and/or triple negative breast cancer.

The term "MUC16-positive cell" refers to a cancer cell that expresses MUC16 on its surface.

The term "HER2," as used herein, refers to any native, mature HER2 which results from processing of a HER2 precursor protein in a cell. The term includes HER2 from any vertebrate source, including mammals such as primates (e.g. humans and cynomolgus or rhesus monkeys) and rodents (e.g., mice and rats), unless otherwise indicated. The term also includes naturally occurring variants of HER2, e.g., splice variants or allelic variants. The amino acid sequence of an exemplary human HER2 precursor protein, with signal sequence (amino acids 1-22=signal sequence) is shown in UniProtKB/Swiss-Prot Accession No. P04626.1 dated 27 May 2015. The amino acid sequence of an exemplary mature human HER2 is amino acids 23 to 1255 of UniProtKB/Swiss-Prot Accession No. P04626.1 dated 27 May 2015.

The term "HER2-positive cancer" refers to a cancer comprising cells that express HER2 on their surface. For the purposes of determining whether a cell expresses HER2 on the surface, HER2 mRNA expression is considered to correlate to HER2 expression on the cell surface. In some embodiments, expression of HER2 mRNA is determined by a method selected from in situ hybridization and RT-PCR (including quantitative RT-PCR). Alternatively, expression of HER2 on the cell surface can be determined, for example, using antibodies to HER2 in a method such as immunohistochemistry, FACS, etc. In some embodiments, a HER2-positive cancer is a breast cancer, metastatic breast cancer, or gastric cancer.

The term "HER2-positive cell" refers to a cancer cell that expresses HER2 on its surface.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result. The effective amount of the drug for treating cancer may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human. In some embodiments, the patient may be a "cancer patient," i.e. one who is suffering or at risk for suffering from one or more symptoms of cancer, in particular gastric or breast cancer.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-[target] antibody," such as an "isolated nucleic acid encoding an anti-Ly6E antibody," refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3) Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

By "co-administering" is meant intravenously administering two (or more) drugs during the same administration, rather than sequential infusions of the two or more drugs.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

A "chemotherapy" is use of a chemotherapeutic agent useful in the treatment of cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Examples of chemotherapeutic agents include: anthracyclines, such as epirubicin or doxorubicin (ADRIAMYCIN®), cyclophosphamide (CYTOXAN®, NEOSAR®), anthracycline and cyclophosphamide in combination ("AC"); a taxane, e.g., docetaxel (TAXOTERE®,) or paclitaxel (TAXOL®), 5-FU (fluorouracil, 5-fluorouracil, CAS No. 51-21-8), lapatinib (TYKERB®), capecitabine (XELODA®), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), temozolomide (4-methyl-5-oxo-2,3,4,6,8-pentazabicyclo[4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®).

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaII (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimeterxate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; ibandronate; CPT-11; topoisomerase inhibitor RFS 2000; difluoromethylornithine (DMFO); retinoids such as retinoic acid; and pharmaceutically acceptable salts, acids and derivatives of any of the above.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J Immunol*. 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on immunoconjugates comprising antibodies that bind to Ly6E, STEAP1, CD79b, MUC16, or HER2. Antibodies and immunoconjugates of the invention are useful, e.g., for the diagnosis or treatment of cancers that express Ly6E, STEAP1, CD79b, MUC16, or HER2.

A. Exemplary Antibodies

Provided herein are immunoconjugates comprising isolated antibodies that bind to an antigen selected from Ly6E, STEAP1, CD79b, MUC16, and HER2. In any of the embodiments described herein, the antibodies may be monoclonal antibodies. In some embodiments, the antibodies may be human antibodies, humanized antibodies, or chimeric antibodies.

Exemplary Anti-Ly6E Antibodies

Lymphocyte antigen 6 complex, locus E (Ly6E), also known as retinoic acid induced gene E (RIG-E) and stem cell antigen 2 (SCA-2). It is a GPI linked, 131 amino acid length, ~8.4 kDa protein of unknown function with no known binding partners. It was initially identified as a transcript expressed in immature thymocyte, thymic medullary epithelial cells in mice. Mao, et al. *Proc. Natl. Acad. Sci. U.S.A.* 93:5910-5914 (1996).

In some embodiments, the invention provides an immunoconjugate comprising an anti-Ly6E antibody described in PCT Publication No. WO 2013/177055.

In some embodiments, the invention provides an immunoconjugate comprising an anti-Ly6E antibody comprising at least one, two, three, four, five, or six HVRs selected from (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 3; (e) HVR-L2 comprising the amino acid sequence of SEQ ID NO: 4; and (f) HVR-L3 comprising the amino acid sequence of SEQ ID NO: 5.

In one aspect, the invention provides an immunoconjugate comprising an antibody that comprises at least one, at least two, or all three VH HVR sequences selected from (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8. In a further embodiment, the antibody comprises (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8.

In another aspect, the invention provides an immunoconjugate comprising an antibody that comprises at least one, at least two, or all three VL HVR sequences selected from (a) HVR-L1 comprising the amino acid sequence of SEQ ID NO: 3; (b) HVR-L2 comprising the amino acid sequence of SEQ ID NO: 4; and (c) HVR-L3 comprising the amino acid sequence of SEQ ID NO: 5. In one embodiment, the antibody comprises (a) HVR-L1 comprising the amino acid sequence of SEQ ID NO: 3; (b) HVR-L2 comprising the amino acid sequence of SEQ ID NO: 4; and (c) HVR-L3 comprising the amino acid sequence of SEQ ID NO: 5.

In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 6, (ii) HVR-H2 comprising the amino acid sequence of SEQ ID NO: 7, and (iii) HVR-H3 comprising an amino acid sequence selected from SEQ ID NO: 8; and (b) a VL domain comprising at least one, at least two, or all three VL HVR sequences selected from (i) HVR-L1 comprising the amino acid sequence of SEQ ID NO: 3, (ii) HVR-L2 comprising the amino acid sequence of SEQ ID NO: 4, and (c) HVR-L3 comprising the amino acid sequence of SEQ ID NO: 5.

In another aspect, the invention provides an immunoconjugate comprising an antibody that comprises (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 3; (e) HVR-L2 comprising the amino acid sequence of SEQ ID NO: 4; and (f) HVR-L3 comprising the amino acid sequence of SEQ ID NO: 5.

In any of the above embodiments, an anti-Ly6E antibody of an immunoconjugate is humanized. In one embodiment, an anti-Ly6E antibody comprises HVRs as in any of the above embodiments, and further comprises a human acceptor framework, e.g. a human immunoglobulin framework or a human consensus framework.

In another aspect, an anti-Ly6E antibody of an immunoconjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 2. In certain embodiments, a VH sequence having at least 90%, 91%, 92%, 93%, 94%, 95%, 96%, 97%, 98%, or 99% identity to the amino acid sequence of SEQ ID NO:2 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 2. In certain embodiments, a total of 1 to 5 amino acids have been substituted, inserted and/or deleted in SEQ ID NO: 2. In certain embodiments, substitutions, insertions, or deletions occur in regions outside the HVRs (i.e., in the FRs). Optionally, the anti-Ly6E antibody comprises the VH sequence of SEQ ID NO: 2, including post-translational modifications of that sequence. In a particular embodiment, the VH comprises one, two or three HVRs selected from: (a) HVR-H1 comprising the amino acid sequence of SEQ ID NO: 6, (b) HVR-H2 comprising the amino acid sequence of SEQ ID NO: 7, and (c) HVR-H3 comprising the amino acid sequence of SEQ ID NO: 8.

In another aspect, an anti-Ly6E antibody of an immunoconjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 1. In certain embodiments, a VL sequence having at least 90%, 91%, 92%, 93%, 94%, 95%, 96%, 97%, 98%, or 99% identity to the amino acid sequence of SEQ ID NO:1 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 1. In certain embodiments, a total of 1 to 5 amino acids have been substituted, inserted and/or deleted in SEQ ID NO: 1. In certain embodiments, the substitutions, insertions, or deletions occur in regions outside the HVRs (i.e., in the FRs). Optionally, the anti-Ly6E antibody comprises the VL sequence of SEQ ID NO: 1, including post-translational modifications of that sequence. In a particular embodiment, the VL comprises one, two or three HVRs selected from (a) HVR-L1 comprising the amino acid sequence of SEQ ID NO: 3; (b) HVR-L2 comprising the amino acid sequence of SEQ ID NO: 4; and (c) HVR-L3 comprising the amino acid sequence of SEQ ID NO: 5.

In another aspect, an immunoconjugate comprising an anti-Ly6E antibody is provided, wherein the antibody comprises a VH as in any of the embodiments provided above, and a VL as in any of the embodiments provided above.

In one embodiment, an immunoconjugate is provided, wherein the antibody comprises the VH and VL sequences in SEQ ID NO: 2 and SEQ ID NO: 1, respectively, including post-translational modifications of those sequences.

In a further aspect, provided herein are immunoconjugates comprising antibodies that bind to the same epitope as an anti-Ly6E antibody provided herein. For example, in certain embodiments, an immunoconjugate is provided comprising an antibody that binds to the same epitope as an anti-Ly6E antibody comprising a VH sequence of SEQ ID NO: 2 and a VL sequence of SEQ ID NO: 1, respectively.

In a further aspect of the invention, an anti-Ly6E antibody of an immunoconjugate according to any of the above embodiments is a monoclonal antibody, including a human antibody.

In one embodiment, an anti-Ly6E antibody of an immunoconjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein. In some embodiments, an immunoconjugate comprises an anti-Ly6E antibody comprising a heavy chain and a light chain comprising the amino acid sequences of SEQ ID NO: 10 and 9, respectively.

In a further aspect, an anti-Ly6E antibody according to any of the above embodiments may incorporate any of the features, singly or in combination, as described in (1) to (7) below.

Exemplary Anti-STEAP1 Antibodies

Cell surface antigen STEAP-1 is described, e.g., in U.S. Pat. No. 6,329,503. STEAP-1 is member of cell surface serpentine transmembrane antigens. It is expressed predominantly in the prostate cancer, and thus members of this family have been termed "STEAP" (Six Transmembrane Epithelial Antigens of the Prostate). Human STEAP proteins exhibit a high degree of structural conservation within the family but show no significant structural homology to any known human proteins. STEAP-1 appears to be a type IIIa membrane protein expressed predominantly in prostate cells in normal human tissues. Structurally, STEAP-1 is a 339 amino acid protein characterized by a molecular topology of six transmembrane domains and intracellular N- and C-termini, suggesting that it folds in a "serpentine" manner into three extracellular and two intracellular loops. STEAP-1 protein expression is maintained at high levels across various states of prostate cancer. STEAP-1 is highly overexpressed in other human cancers such as lung and colon. Murine antibodies have been raised to human STEAP-1 fragments and the antibodies were shown to bind STEAP-1 on the cell surface (see US Patent Application No. 20040253232A1).

In some embodiments, the invention provides an immunoconjugate comprising an anti-STEAP1 antibody described in U.S. Pat. No. 8,436,147 B2.

In some embodiments, the invention provides an immunoconjugate comprising an anti-STEAP1 antibody comprising at least one, two, three, four, five, or six HVRs selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60.

In one aspect, the invention provides an immunoconjugate comprising an antibody that comprises at least one, at least two, or all three VH HVR sequences selected from (a) HVR-H1 comprising the amino acid sequence of SEQ ID NO: 55; (b) HVR-H2 comprising the amino acid sequence of SEQ ID NO: 56; and (c) HVR-H3 comprising the amino acid sequence of SEQ ID NO: 57. In a further embodiment, the antibody comprises (a) HVR-H1 comprising the amino acid sequence of SEQ ID NO: 55; (b) HVR-H2 comprising the amino acid sequence of SEQ ID NO: 56; and (c) HVR-H3 comprising the amino acid sequence of SEQ ID NO: 57.

In another aspect, the invention provides an immunoconjugate comprising an antibody that comprises at least one, at least two, or all three VL HVR sequences selected from (a) HVR-L1 comprising the amino acid sequence of SEQ ID NO: 58; (b) HVR-L2 comprising the amino acid sequence of SEQ ID NO: 59; and (c) HVR-L3 comprising the amino acid sequence of SEQ ID NO: 60. In one embodiment, the antibody comprises (a) HVR-L1 comprising the amino acid sequence of SEQ ID NO: 58; (b) HVR-L2 comprising the amino acid sequence of SEQ ID NO: 59; and (c) HVR-L3 comprising the amino acid sequence of SEQ ID NO: 60.

In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 55, (ii) HVR-H2 comprising the amino acid sequence of SEQ ID NO: 56, and (iii) HVR-H3 comprising an amino acid sequence selected from SEQ ID NO: 57; and (b) a VL domain comprising at least one, at least two, or all three VL HVR sequences selected from (i) HVR-L1 comprising the amino acid sequence of SEQ ID NO: 58, (ii) HVR-L2 comprising the amino acid sequence of SEQ ID NO: 59, and (c) HVR-L3 comprising the amino acid sequence of SEQ ID NO: 60.

In another aspect, the invention provides an immunoconjugate comprising an antibody that comprises (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 58; (e) HVR-L2 comprising the amino acid sequence of SEQ ID NO: 59; and (f) HVR-L3 comprising the amino acid sequence of SEQ ID NO: 60.

In any of the above embodiments, an anti-STEAP1 antibody of an immunoconjugate is humanized. In one embodiment, an anti-STEAP1 antibody comprises HVRs as in any of the above embodiments, and further comprises a human acceptor framework, e.g. a human immunoglobulin framework or a human consensus framework.

In another aspect, an anti-STEAP1 antibody of an immunoconjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 61. In certain embodiments, a VH sequence having at least 90%, 91%, 92%, 93%, 94%, 95%, 96%, 97%, 98%, or 99% identity to the amino acid sequence of SEQ ID NO: 61 contains substitutions (e.g., conservative substitutions), insertions, or deletions relative to the reference sequence, but an anti-STEAP1 antibody comprising that sequence retains the ability to bind to STEAP1. In certain embodiments, a total of 1 to 10 amino acids have been substituted, inserted and/or deleted in SEQ ID NO: 61. In certain embodiments, a total of 1 to 5 amino acids have been substituted, inserted and/or deleted in SEQ ID NO: 61. In certain embodiments, substitutions, insertions, or deletions occur in regions outside the HVRs (i.e., in the FRs). Optionally, the anti-STEAP1 antibody comprises the VH sequence of SEQ ID NO: 61, including post-translational modifications of that sequence. In a particular embodiment, the VH comprises one, two or three HVRs selected from: (a) HVR-H1 comprising the amino acid sequence of SEQ ID NO: 55, (b) HVR-H2 comprising the amino acid sequence of SEQ ID NO: 56, and (c) HVR-H3 comprising the amino acid sequence of SEQ ID NO: 57.

In another aspect, an anti-STEAP1 antibody of an immunoconjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 62. In certain embodiments, a VL sequence having at least 90%, 91%, 92%, 93%, 94%, 95%, 96%, 97%, 98%, or 99% identity to the amino acid sequence of SEQ ID NO: 62 contains substitutions (e.g., conservative substitutions), insertions, or deletions relative to the reference sequence, but an anti-STEAP1 antibody comprising that sequence retains the ability to bind to STEAP1. In certain embodiments, a total of 1 to 10 amino acids have been substituted, inserted and/or deleted in SEQ ID NO: 62. In certain embodiments, a total of 1 to 5 amino acids have been substituted, inserted and/or deleted in SEQ ID NO: 62. In certain embodiments, the substitutions, insertions, or deletions occur in regions outside the HVRs (i.e., in the FRs). Optionally, the anti-STEAP1 antibody comprises the VL sequence of SEQ ID NO: 62, including post-translational modifications of that sequence. In a particular embodiment, the VL comprises one, two or three HVRs selected from (a) HVR-L1 comprising the amino acid sequence of SEQ ID NO: 58; (b) HVR-L2 comprising the amino acid sequence of SEQ ID NO: 59; and (c) HVR-L3 comprising the amino acid sequence of SEQ ID NO: 60.

In another aspect, an immunoconjugate comprising an anti-STEAP1 antibody is provided, wherein the antibody comprises a VH as in any of the embodiments provided above, and a VL as in any of the embodiments provided above.

In one embodiment, an immunoconjugate is provided, wherein the antibody comprises the VH and VL sequences in SEQ ID NO: 61 and SEQ ID NO: 62, respectively, including post-translational modifications of those sequences.

In a further aspect, provided herein are immunoconjugates comprising antibodies that bind to the same epitope as an anti-STEAP1 antibody provided herein. For example, in certain embodiments, an immunoconjugate is provided comprising an antibody that binds to the same epitope as an anti-STEAP1 antibody comprising a VH sequence of SEQ ID NO: 61 and a VL sequence of SEQ ID NO: 62, respectively.

In a further aspect of the invention, an anti-STEAP1 antibody of an immunoconjugate according to any of the above embodiments is a monoclonal antibody, including a human antibody. In one embodiment, an anti-STEAP1 antibody of an immunoconjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-STEAP1 antibody according to any of the above embodiments may incorporate any of the features, singly or in combination, as described in (1) to (7) below.

Exemplary Anti-CD79b Antibodies

CD79 is the signaling component of the B-cell receptor consisting of a covalent heterodimer containing CD79a (Igα, mb-1) and CD79b (Igβ, B29). CD79a and CD79b each contain an extracellular immunoglobulin (Ig) domain, a transmembrane domain, and an intracellular signaling domain, an immunoreceptor tyrosine-based activation motif (ITAM) domain. CD79 is expressed on B cells and, for example, in Non-Hodgkin's Lymphoma cells (NHLs) (Cabezudo et al., *Haematologica*, 84:413-418 (1999); D'Arena et al., *Am. J. Hematol.*, 64: 275-281 (2000); Olejniczak et al., *Immunol. Invest.*, 35: 93-114 (2006)). CD79a and CD79b and sIg are all required for surface expression of the CD79 (Matsuuchi et al., *Curr. Opin. Immunol.*, 13(3): 270-7)). The average surface expression of CD79b on NHLs is similar to that on normal B-cells, but with a greater range (Matsuuchi et al., *Curr. Opin. Immunol.*, 13(3): 270-7 (2001)).

In some embodiments, the invention provides an immunoconjugate comprising an anti-CD79b antibody described in U.S. Pat. No. 8,088,378 B2.

In some embodiments, the invention provides an immunoconjugate comprising an anti-CD79b antibody comprising at least one, two, three, four, five, or six HVRs selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54.

In one aspect, the invention provides an immunoconjugate comprising an antibody that comprises at least one, at least two, or all three VH HVR sequences selected from (a) HVR-H1 comprising the amino acid sequence of SEQ ID NO: 49; (b) HVR-H2 comprising the amino acid sequence of SEQ ID NO: 50; and (c) HVR-H3 comprising the amino acid sequence of SEQ ID NO: 51. In a further embodiment, the antibody comprises (a) HVR-H1 comprising the amino acid sequence of SEQ ID NO: 49; (b) HVR-H2 comprising the amino acid sequence of SEQ ID NO: 50; and (c) HVR-H3 comprising the amino acid sequence of SEQ ID NO: 51.

In another aspect, the invention provides an immunoconjugate comprising an antibody that comprises at least one, at least two, or all three VL HVR sequences selected from (a) HVR-L1 comprising the amino acid sequence of SEQ ID NO: 52; (b) HVR-L2 comprising the amino acid sequence of SEQ ID NO: 53; and (c) HVR-L3 comprising the amino acid sequence of SEQ ID NO: 54. In one embodiment, the antibody comprises (a) HVR-L1 comprising the amino acid sequence of SEQ ID NO: 52; (b) HVR-L2 comprising the amino acid sequence of SEQ ID NO: 53; and (c) HVR-L3 comprising the amino acid sequence of SEQ ID NO: 54.

In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 49, (ii) HVR-H2 comprising the amino acid sequence of SEQ ID NO: 50, and (iii) HVR-H3 comprising an amino acid sequence selected from SEQ ID NO: 51; and (b) a VL domain comprising at least one, at least two, or all three VL HVR sequences selected from (i) HVR-L1 comprising the amino acid sequence of SEQ ID NO: 52, (ii) HVR-L2 comprising the amino acid sequence of SEQ ID NO: 53, and (c) HVR-L3 comprising the amino acid sequence of SEQ ID NO: 54.

In another aspect, the invention provides an immunoconjugate comprising an antibody that comprises (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54.

In any of the above embodiments, an anti-CD79b antibody of an immunoconjugate is humanized. In one embodiment, an anti-CD79b antibody of an immunoconjugate comprises HVRs as in any of the above embodiments, and further comprises a human acceptor framework, e.g. a human immunoglobulin framework or a human consensus framework.

In another aspect, an anti-CD79b antibody of an immunoconjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 47. In certain embodiments, a VH sequence having at least 90%, 91%, 92%, 93%, 94%, 95%, 96%, 97%, 98%, or 99% identity to the amino acid sequence of SEQ ID NO: 47 contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO: 47. In certain embodiments, a total of 1 to 5 amino acids have been substituted, inserted and/or deleted in SEQ ID NO: 47. In certain embodiments, substitutions, insertions, or deletions occur in regions outside the HVRs (i.e., in the FRs). Optionally, the anti-CD79b antibody comprises the VH sequence of SEQ ID NO: 47, including post-translational modifications of that sequence. In a particular embodiment, the VH comprises one, two or three HVRs selected from: (a) HVR-H1 comprising the amino acid sequence of SEQ ID NO: 49, (b) HVR-H2 comprising the amino acid sequence of SEQ ID NO: 50, and (c) HVR-H3 comprising the amino acid sequence of SEQ ID NO: 51.

In another aspect, an anti-CD79b antibody of an immunoconjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 10. In certain embodiments, a VL sequence having at least 90%, 91%, 92%, 93%, 94%, 95%, 96%, 97%, 98%, or 99% identity to the amino acid sequence of SEQ ID NO:48 contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO: 48. In certain embodiments, a total of 1 to 5 amino acids have been substituted, inserted and/or deleted in SEQ ID NO: 48. In certain embodiments, the substitutions, insertions, or deletions occur in regions outside the HVRs (i.e., in the FRs). Optionally, the anti-CD79b antibody comprises the VL sequence of SEQ ID NO: 48, including post-translational modifications of that sequence. In a particular embodiment, the VL comprises one, two or three HVRs selected from (a) HVR-L1 comprising the amino acid sequence of SEQ ID NO: 52; (b) HVR-L2 comprising the amino acid sequence of SEQ ID NO: 53; and (c) HVR-L3 comprising the amino acid sequence of SEQ ID NO: 54.

In another aspect, an immunoconjugate comprising an anti-CD79b antibody is provided, wherein the antibody comprises a VH as in any of the embodiments provided above, and a VL as in any of the embodiments provided above.

In one embodiment, an immunoconjugate comprising an antibody is provided, wherein the antibody comprises the VH and VL sequences in SEQ ID NO: 47 and SEQ ID NO: 48, respectively, including post-translational modifications of those sequences.

In a further aspect, provided herein are immunoconjugates comprising antibodies that bind to the same epitope as an anti-CD79b antibody provided herein. For example, in certain embodiments, an immunoconjugate is provided, comprising an antibody that binds to the same epitope as an anti-CD79b antibody comprising a VH sequence of SEQ ID NO: 47 and a VL sequence of SEQ ID NO: 48, respectively.

In a further aspect of the invention, an anti-CD79b antibody of an immunoconjugate according to any of the above embodiments is a monoclonal antibody, including a human antibody. In one embodiment, an anti-CD79b antibody of an immunoconjugate is an antibody fragment, e.g., a Fv, Fab, Fab', scFv, diabody, or F(ab')$_2$ fragment. In another embodiment, an immunoconjugate comprises an antibody that is a substantially full length antibody, e.g., an IgG1 antibody, IgG2a antibody or other antibody class or isotype as defined herein.

In a further aspect, an anti-CD79b antibody of an immunoconjugate according to any of the above embodiments may incorporate any of the features, singly or in combination, as described in (1) to (7) below.

Exemplary Anti-MUC16 Antibodies

MUC16 is a large transmembrane protein that is overexpressed by the majority (80%) of human epithelial ovarian cancers but not in the epithelium of normal ovaries (O'Brien et al (2001) Tumour Biol. 22:348-366), and on PC cells (50%). While the function of MUC16 remains unclear, MUC16 may facilitate the binding of tumor cells to mesothelial cells lining the peritoneal cavity and may inhibit natural killer cell-mediated anti-tumor cytotoxic responses and it may provide a protective, lubricating barrier against particles and infectious agents at mucosal surfaces. Highly polymorphic, MUC16 is composed of three domains, a Ser-/Thr-rich N-terminal domain, a repeat domain of between eleven and more than 60 partially conserved tandem repeats of on average 156 amino acids each, and a C-terminal non-repeating domain containing a transmembrane sequence and a short cytoplasmic tail. MUC16 is heavily O-glycosylated and N-glycosylated (O'Brien et al (2002) Tumour Biol. 23:154-169; O'Brien et al (2001) Tumour Biol. 22:348-366; Fendrick et al (1997) Tumour Biol. 18:278-289; Wong et al (2003) J. Biol. Chem. 278: 28619-28634; McLemore et al (2005) Biol. Res. Nurs. 6:262-267).

In some embodiments, the invention provides an immunoconjugate comprising an anti-MUC16 antibody described in U.S. Pat. No. 7,989,595 B2.

In some embodiments, the invention provides an immunoconjugate comprising an anti-MUC16 antibody comprising at least one, two, three, four, five, or six HVRs selected from (a) HVR-H1 comprising the amino acid sequence of SEQ ID NO: 18; (b) HVR-H2 comprising the amino acid sequence of SEQ ID NO: 19; (c) HVR-H3 comprising the amino acid sequence of SEQ ID NO: 20; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17. In some embodiments, the invention provides an immunoconjugate comprising an anti-MUC16 antibody comprising at least one, two, three, four, five, or six HVRs selected from (a) HVR-H1 comprising the amino acid sequence of SEQ ID NO: 26; (b) HVR-H2 comprising the amino acid sequence of SEQ ID NO: 27; (c) HVR-H3 comprising the amino acid sequence of SEQ ID NO: 28; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25. In some embodiments, the invention provides an immunoconjugate comprising an anti-MUC16 antibody comprising at least one, two, three, four, five, or six HVRs selected from (a) HVR-H1 comprising the amino acid sequence of SEQ ID NO: 34; (b) HVR-H2 comprising the amino acid sequence of SEQ ID NO: 35; (c) HVR-H3 comprising the amino acid sequence of SEQ ID NO: 36; (d) HVR-L1 comprising the amino acid sequence of SEQ ID NO: 31; (e) HVR-L2 comprising the amino acid sequence of SEQ ID NO: 32; and (f) HVR-L3 comprising the amino acid sequence of SEQ ID NO: 33. In some embodiments, the invention provides an immunoconjugate comprising an anti-MUC16 antibody comprising at least one, two, three, four, five, or six HVRs selected from (a) HVR-H1 comprising the amino acid sequence of SEQ ID NO: 42; (b) HVR-H2 comprising the amino acid sequence of SEQ ID NO: 43; (c) HVR-H3 comprising the amino acid sequence of SEQ ID NO: 44; (d) HVR-L1 comprising the amino acid sequence of SEQ ID NO: 39; (e) HVR-L2 comprising the amino acid sequence of SEQ ID NO: 40; and (f) HVR-L3 comprising the amino acid sequence of SEQ ID NO: 41.

In one aspect, the invention provides an immunoconjugate comprising an antibody that comprises at least one, at least two, or all three VH HVR sequences selected from (a) HVR-H1 comprising the amino acid sequence of SEQ ID NO: 18; (b) HVR-H2 comprising the amino acid sequence of SEQ ID NO: 19; and (c) HVR-H3 comprising the amino acid sequence of SEQ ID NO: 20. In a further embodiment, the antibody comprises (a) HVR-H1 comprising the amino acid sequence of SEQ ID NO: 18; (b) HVR-H2 comprising the amino acid sequence of SEQ ID NO: 19; and (c) HVR-H3 comprising the amino acid sequence of SEQ ID NO: 20. In one aspect, the invention provides an immunoconjugate comprising an antibody that comprises at least one, at least two, or all three VH HVR sequences selected from (a) HVR-H1 comprising the amino acid sequence of SEQ ID NO: 26; (b) HVR-H2 comprising the amino acid sequence of SEQ ID NO: 27; and (c) HVR-H3 comprising the amino acid sequence of SEQ ID NO: 28. In a further embodiment, the antibody comprises (a) HVR-H1 comprising the amino acid sequence of SEQ ID NO: 26; (b) HVR-H2 comprising the amino acid sequence of SEQ ID NO: 27; and (c) HVR-H3 comprising the amino acid sequence of SEQ ID NO: 28. In one aspect, the invention provides an immunoconjugate comprising an antibody that comprises at least one, at least two, or all three VH HVR sequences selected from (a) HVR-H1 comprising the amino acid sequence of SEQ ID NO: 34; (b) HVR-H2 comprising the amino acid sequence of SEQ ID NO: 35; and (c) HVR-H3 comprising the amino acid sequence of SEQ ID NO: 36. In a further embodiment, the antibody comprises (a) HVR-H1 comprising the amino acid sequence of SEQ ID NO: 34; (b) HVR-H2 comprising the amino acid sequence of SEQ ID NO: 35; and (c) HVR-H3 comprising the amino acid sequence of SEQ ID NO: 36. In one aspect, the invention provides an immunoconjugate comprising an antibody that comprises at least one, at least two, or all three VH HVR sequences selected from (a) HVR-H1 comprising the amino acid sequence of SEQ ID NO: 42; (b) HVR-H2 comprising the amino acid sequence of SEQ ID NO: 43; and (c) HVR-H3 comprising the amino acid sequence of SEQ ID NO: 44. In a further embodiment, the antibody comprises (a) HVR-H1 comprising the amino acid sequence of SEQ ID NO: 42; (b) HVR-H2 comprising the amino acid sequence of SEQ ID NO: 43; and (c) HVR-H3 comprising the amino acid sequence of SEQ ID NO: 44.

In another aspect, the invention provides an immunoconjugate comprising an antibody that comprises at least one, at least two, or all three VL HVR sequences selected from (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17. In one embodiment, the antibody comprises (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17. In another aspect, the invention provides an immunoconjugate comprising an antibody that comprises at least one, at least two, or all three VL HVR sequences selected from (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25. In one embodiment, the antibody comprises (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25. In another aspect, the invention provides an immunoconjugate comprising an antibody that comprises at least one, at least two, or all three VL HVR sequences selected from (a) HVR-L1 comprising the amino acid sequence of SEQ ID NO: 31; (b) HVR-L2 comprising the amino acid sequence of SEQ ID NO: 32; and (c) HVR-L3 comprising the amino acid sequence of SEQ ID NO: 33. In one embodiment, the antibody comprises (a) HVR-L1 comprising the amino acid sequence of SEQ ID NO: 31; (b) HVR-L2 comprising the amino acid sequence of SEQ ID NO: 32; and (c) HVR-L3 comprising the amino acid sequence of SEQ ID NO: 33. In another aspect, the invention provides an immunoconjugate comprising an antibody that comprises at least one, at least two, or all three VL HVR sequences selected from (a) HVR-L1 comprising the amino acid sequence of SEQ ID NO: 39; (b) HVR-L2 comprising the amino acid sequence of SEQ ID NO: 40; and (c) HVR-L3 comprising the amino acid sequence of SEQ ID NO: 41. In one embodiment, the antibody comprises (a) HVR-L1 comprising the amino acid sequence of SEQ ID NO: 39; (b) HVR-L2 comprising the amino acid sequence of SEQ ID NO: 40; and (c) HVR-L3 comprising the amino acid sequence of SEQ ID NO: 41.

In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 18, (ii) HVR-H2 comprising the amino acid sequence of SEQ ID NO: 19, and (iii) HVR-H3 comprising an amino acid sequence selected from SEQ ID NO: 20; and (b) a VL domain comprising at least one, at least two, or all three VL HVR sequences selected from (i) HVR-L1 comprising the amino acid sequence of SEQ ID NO: 15, (ii) HVR-L2 comprising the amino acid sequence of SEQ ID NO: 16, and (c) HVR-L3 comprising the amino acid sequence of SEQ ID NO: 17. In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 26, (ii) HVR-H2 comprising the amino acid sequence of SEQ ID NO: 27, and (iii) HVR-H3 comprising an amino acid sequence selected from SEQ ID NO: 28; and (b) a VL domain comprising at least one, at least two, or all three VL HVR sequences selected from (i) HVR-L1 comprising the amino acid sequence of SEQ ID NO: 23, (ii) HVR-L2 comprising the amino acid sequence of SEQ ID NO: 24, and (c) HVR-L3 comprising the amino acid sequence of SEQ ID NO: 25. In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 34, (ii) HVR-H2 comprising the amino acid sequence of SEQ ID NO: 35, and (iii) HVR-H3 comprising an amino acid sequence selected from SEQ ID NO: 36; and (b) a VL domain comprising at least one, at least two, or all three VL HVR sequences selected from (i) HVR-L1 comprising the amino acid sequence of SEQ ID NO: 31, (ii) HVR-L2 comprising the amino acid sequence of SEQ ID NO: 32, and (c) HVR-L3 comprising the amino acid sequence of SEQ ID NO: 33. In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 42, (ii) HVR-H2 comprising the amino acid sequence of SEQ ID NO: 43, and (iii) HVR-H3 comprising an amino acid sequence selected from SEQ ID NO: 44; and (b) a VL domain comprising at least one, at least two, or all three VL HVR sequences selected from (i) HVR-L1 comprising the amino acid sequence of SEQ ID NO: 39, (ii) HVR-L2 comprising the amino acid sequence of SEQ ID NO: 40, and (c) HVR-L3 comprising the amino acid sequence of SEQ ID NO: 41.

In some embodiments, the invention provides an immunoconjugate comprising an antibody that comprises (a) HVR-H1 comprising the amino acid sequence of SEQ ID NO: 18; (b) HVR-H2 comprising the amino acid sequence of SEQ ID NO: 19; (c) HVR-H3 comprising the amino acid sequence of SEQ ID NO: 20; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17. In some embodiments, the invention provides an immunoconjugate comprising an antibody that comprises (a) HVR-H1 comprising the amino acid sequence of SEQ ID NO: 26; (b) HVR-H2 comprising the amino acid sequence of SEQ ID NO: 27; (c) HVR-H3 comprising the amino acid sequence of SEQ ID NO: 28; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25. In some embodiments, the invention provides an immunoconjugate comprising an antibody that comprises (a) HVR-H1 comprising the amino acid sequence of SEQ ID NO: 34; (b) HVR-H2 comprising the amino acid sequence of SEQ ID NO: 35; (c) HVR-H3 comprising the amino acid sequence of SEQ ID NO: 36; (d) HVR-L1 comprising the amino acid sequence of SEQ ID NO: 31; (e) HVR-L2 comprising the amino acid sequence of SEQ ID NO: 32; and (f) HVR-L3 comprising the amino acid sequence of SEQ ID NO: 33. In some embodiments, the invention provides an immunoconjugate comprising an antibody that comprises (a) HVR-H1 comprising the amino acid sequence of SEQ ID NO: 42; (b) HVR-H2 comprising the amino acid sequence of SEQ ID NO: 43; (c) HVR-H3 comprising the amino acid sequence of SEQ ID NO: 44; (d) HVR-L1 comprising the amino acid sequence of SEQ ID NO: 39; (e) HVR-L2 comprising the amino acid sequence of SEQ ID NO: 40; and (f) HVR-L3 comprising the amino acid sequence of SEQ ID NO: 41.

In any of the above embodiments, an immunoconjugate comprises an anti-MUC16 antibody that is humanized. In one embodiment, an anti-MUC16 antibody of an immunoconjugate comprises HVRs as in any of the above embodiments, and further comprises a human acceptor framework, e.g. a human immunoglobulin framework or a human consensus framework.

In another aspect, an immunoconjugate comprises an anti-MUC16 antibody that comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 22, 30, 38, or 46. In certain embodiments, a VH sequence having at least 90%, 91%, 92%, 93%, 94%, 95%, 96%, 97%, 98%, or 99% identity to the amino acid sequence of SEQ ID NO: 22, 30, 38, or 46 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 22, 30, 38, or 46. In certain embodiments, a total of 1 to 5 amino acids have been substituted, inserted and/or deleted in SEQ ID NO: 22, 30, 38, or 46. In certain embodiments, substitutions, insertions, or deletions occur in regions outside the HVRs (i.e., in the FRs). Optionally, the anti-MUC16 antibody comprises the VH sequence of SEQ ID NO: 22, 30, 38, or 46, including post-translational modifications of that sequence. In some embodiments, the VH comprises one, two or three HVRs selected from: (a) HVR-H1 comprising the amino acid sequence of SEQ ID NO: 18, 26, 34, or 42, (b) HVR-H2 comprising the amino acid sequence of SEQ ID NO: 19, 27, 35, or 43, and (c) HVR-H3 comprising the amino acid sequence of SEQ ID NO: 20, 28, 36, or 44.

In another aspect, an anti-MUC16 antibody of an immunoconjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 21, 29, 37, or 45. In certain embodiments, a VL sequence having at least 90%, 91%, 92%, 93%, 94%, 95%, 96%, 97%, 98%, or 99% identity to the amino acid sequence of SEQ ID NO: 21, 29, 37, or 45 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 21, 29, 37, or 45. In certain embodiments, a total of 1 to 5 amino acids have been substituted, inserted and/or deleted in SEQ ID NO: 21, 29, 37, or 45. In certain embodiments, the substitutions, insertions, or deletions occur in regions outside the HVRs (i.e., in the FRs). Optionally, the anti-MUC16 antibody comprises the VL sequence of SEQ ID NO: 21, 29, 37, or 45, including post-translational modifications of that sequence. In a particular embodiment, the VL comprises one, two or three HVRs selected from (a) HVR-L1 comprising the amino acid sequence of SEQ ID NO: 15, 23, 31, or 39; (b) HVR-L2 comprising the amino acid sequence of SEQ ID NO: 16, 24, 32, or 40; and (c) HVR-L3 comprising the amino acid sequence of SEQ ID NO: 17, 25, 33, or 41.

In another aspect, an immunoconjugate comprising anti-MUC16 antibody is provided, wherein the antibody comprises a VH as in any of the embodiments provided above, and a VL as in any of the embodiments provided above.

In one embodiment, the antibody of the immunoconjugate comprises the VH and VL sequences in SEQ ID NO: 22 and SEQ ID NO: 21, respectively, including post-translational modifications of those sequences. In one embodiment, the antibody of the immunoconjugate comprises the VH and VL sequences in SEQ ID NO: 30 and SEQ ID NO: 29, respectively, including post-translational modifications of those sequences. In one embodiment, the antibody of the immunoconjugate comprises the VH and VL sequences in SEQ ID NO: 38 and SEQ ID NO: 37, respectively, including post-translational modifications of those sequences. In one embodiment, the antibody of the immunoconjugate comprises the VH and VL sequences in SEQ ID NO: 46 and SEQ ID NO: 45, respectively, including post-translational modifications of those sequences.

In a further aspect, provided herein are Immunoconjugates comprising antibodies that bind to the same epitope as an anti-MUC16 antibody provided herein. For example, in certain embodiments, an immunoconjugate is provided, comprising an antibody that binds to the same epitope as an anti-MUC16 antibody comprising a VH sequence and a VL sequence comprising of SEQ ID NOs: 22 and 21, respectively; or SEQ ID NOs: 30 and 29, respectively; or SEQ ID NOs: 38 and 37, respectively; or SEQ ID NOs: 46 and 45, respectively.

In a further aspect of the invention, an immunoconjugate comprises anti-MUC16 antibody according to any of the above embodiments, wherein the antibody is a monoclonal antibody, including a human antibody. In one embodiment, an anti-MUC16 antibody of an immunoconjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-MUC16 antibody of an immunoconjugate according to any of the above embodiments may incorporate any of the features, singly or in combination, as described in (1) to (7) below.

Exemplary Anti-HER2 Antibodies

The HER2 (ErbB2) receptor tyrosine kinase is a member of the epidermal growth factor receptor (EGFR) family of transmembrane receptors. Overexpression of HER2 is observed in approximately 20% of human breast cancers and is implicated in the aggressive growth and poor clinical outcomes associated with these tumors (Slamon et al (1987) Science 235:177-182). HER2 protein overexpression can be determined using an immunohistochemistry based assessment of fixed tumor blocks (Press M F, et al (1993) Cancer Res 53:4960-70).

In some embodiments, the invention provides an immunoconjugate comprising an anti-HER2 antibody. In some embodiments, an anti-HER2 antibody comprises the HVRs of an antibody described in WO 98/17797. In some embodiments, an antibody comprises the HVRs, or the humanized heavy chain variable region and humanized light chain variable region, of an antibody described in U.S. Pat. Nos. 5,677,171; 5,821,337; 6,054,297; 6,165,464; 6,339,142; 6,407,213; 6,639,055; 6,719,971; 6,800,738; or 7,074,404. In some embodiments, the invention provides an immunoconjugate comprising the heavy chain variable region and the light chain variable region of Herceptin® (trastuzumab).

In some embodiments, the invention provides an immunoconjugate comprising an anti-HER2 antibody comprising at least one, two, three, four, five, or six HVRs selected from (a) HVR-H1 comprising the amino acid sequence of SEQ ID NO: 68; (b) HVR-H2 comprising the amino acid sequence of SEQ ID NO: 69, 73, or 74; (c) HVR-H3 comprising the amino acid sequence of SEQ ID NO: 70 or 75; (d) HVR-L1 comprising the amino acid sequence of SEQ ID NO: 65; (e) HVR-L2 comprising the amino acid sequence of SEQ ID NO: 66; and (f) HVR-L3 comprising the amino acid sequence of SEQ ID NO: 67. In some embodiments, the invention provides an immunoconjugate comprising an anti-HER2 antibody comprising at least one, two, three, four, five, or six HVRs selected from (a) HVR-H1 comprising the amino acid sequence of SEQ ID NO: 68; (b) HVR-H2 comprising the amino acid sequence of SEQ ID NO: 69; (c) HVR-H3 comprising the amino acid sequence of SEQ ID NO: 70; (d) HVR-L1 comprising the amino acid sequence of SEQ ID NO: 65; (e) HVR-L2 comprising the amino acid sequence of SEQ ID NO: 66; and (f) HVR-L3 comprising the amino acid sequence of SEQ ID NO: 67.

In some embodiments, the invention provides an immunoconjugate comprising an anti-HER2 antibody comprising at least one, two, three, four, five, or six HVRs selected from (a) HVR-H1 comprising the amino acid sequence of SEQ ID NO: 80; (b) HVR-H2 comprising the amino acid sequence of SEQ ID NO: 81; (c) HVR-H3 comprising the amino acid sequence of SEQ ID NO: 82; (d) HVR-L1 comprising the amino acid sequence of SEQ ID NO: 83; (e) HVR-L2 comprising the amino acid sequence of SEQ ID NO: 84; and (f) HVR-L3 comprising the amino acid sequence of SEQ ID NO: 85.

In one aspect, the invention provides an immunoconjugate comprising an antibody that comprises at least one, at least two, or all three VH HVR sequences selected from (a) HVR-H1 comprising the amino acid sequence of SEQ ID NO: 68; (b) HVR-H2 comprising the amino acid sequence of SEQ ID NO: 69, 73, or 74; and (c) HVR-H3 comprising the amino acid sequence of SEQ ID NO: 70 or 75. In one aspect, the invention provides an immunoconjugate comprising an antibody that comprises at least one, at least two, or all three VH HVR sequences selected from (a) HVR-H1 comprising the amino acid sequence of SEQ ID NO: 68; (b) HVR-H2 comprising the amino acid sequence of SEQ ID NO: 69; and (c) HVR-H3 comprising the amino acid sequence of SEQ ID NO: 70. In a further embodiment, the antibody comprises (a) HVR-H1 comprising the amino acid sequence of SEQ ID NO: 68; (b) HVR-H2 comprising the amino acid sequence of SEQ ID NO: 69, 73, or 74; and (c) HVR-H3 comprising the amino acid sequence of SEQ ID NO: 70 or 75. In a further embodiment, the antibody comprises (a) HVR-H1 comprising the amino acid sequence of SEQ ID NO: 68; (b) HVR-H2 comprising the amino acid sequence of SEQ ID NO: 69; and (c) HVR-H3 comprising the amino acid sequence of SEQ ID NO: 70.

In some embodiments, the antibody comprises (a) HVR-H1 comprising the amino acid sequence of SEQ ID NO: 80; (b) HVR-H2 comprising the amino acid sequence of SEQ ID NO: 81; and (c) HVR-H3 comprising the amino acid sequence of SEQ ID NO: 82.

In another aspect, the invention provides an immunoconjugate comprising an antibody that comprises at least one, at least two, or all three VL HVR sequences selected from (a) HVR-L1 comprising the amino acid sequence of SEQ ID NO: 65; (b) HVR-L2 comprising the amino acid sequence of SEQ ID NO: 66; and (c) HVR-L3 comprising the amino acid sequence of SEQ ID NO: 67. In one embodiment, the antibody comprises (a) HVR-L1 comprising the amino acid sequence of SEQ ID NO: 65; (b) HVR-L2 comprising the amino acid sequence of SEQ ID NO: 66; and (c) HVR-L3 comprising the amino acid sequence of SEQ ID NO: 67.

In some embodiments, the antibody comprises (a) HVR-L1 comprising the amino acid sequence of SEQ ID NO: 83; (b) HVR-L2 comprising the amino acid sequence of SEQ ID NO: 84; and (c) HVR-L3 comprising the amino acid sequence of SEQ ID NO: 85.

In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 68, (ii) HVR-H2 comprising the amino acid sequence of SEQ ID NO: 69, 73, or 74, and (iii) HVR-H3 comprising an amino acid sequence selected from SEQ ID NO: 70 or 75; and (b) a VL domain comprising at least one, at least two, or all three VL HVR sequences selected from (i) HVR-L1 comprising the amino acid sequence of SEQ ID NO: 65, (ii) HVR-L2 comprising the amino acid sequence of SEQ ID NO: 66, and (c) HVR-L3 comprising the amino acid sequence of SEQ ID NO: 67. In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 68, (ii) HVR-H2 comprising the amino acid sequence of SEQ ID NO: 69, and (iii) HVR-H3 comprising an amino acid sequence selected from SEQ ID NO: 70; and (b) a VL domain comprising at least one, at least two, or all three VL HVR sequences selected from (i) HVR-L1 comprising the amino acid sequence of SEQ ID NO: 65, (ii) HVR-L2 comprising the amino acid sequence of SEQ ID NO: 66, and (c) HVR-L3 comprising the amino acid sequence of SEQ ID NO: 67.

In another aspect, an immunoconjugate of the invention comprises an antibody comprising (a) a VH domain comprising at least one, at least two, or all three VH HVR sequences selected from (i) HVR-H1 comprising the amino acid sequence of SEQ ID NO: 80, (ii) HVR-H2 comprising the amino acid sequence of SEQ ID NO: 81, and (iii) HVR-H3 comprising an amino acid sequence selected from SEQ ID NO: 82; and (b) a VL domain comprising at least one, at least two, or all three VL HVR sequences selected from (i) HVR-L1 comprising the amino acid sequence of SEQ ID NO: 83, (ii) HVR-L2 comprising the amino acid sequence of SEQ ID NO: 84, and (c) HVR-L3 comprising the amino acid sequence of SEQ ID NO: 85.

In another aspect, the invention provides an immunoconjugate comprising an antibody that comprises (a) HVR-H1 comprising the amino acid sequence of SEQ ID NO: 68; (b) HVR-H2 comprising the amino acid sequence of SEQ ID NO: 69, 73, or 74; (c) HVR-H3 comprising the amino acid sequence of SEQ ID NO: 70 or 75; (d) HVR-L1 comprising the amino acid sequence of SEQ ID NO: 65; (e) HVR-L2 comprising the amino acid sequence of SEQ ID NO: 66; and (f) HVR-L3 comprising the amino acid sequence of SEQ ID NO: 67. In another aspect, the invention provides an immunoconjugate comprising an antibody that comprises (a) HVR-H1 comprising the amino acid sequence of SEQ ID NO: 68; (b) HVR-H2 comprising the amino acid sequence of SEQ ID NO: 69; (c) HVR-H3 comprising the amino acid sequence of SEQ ID NO: 70; (d) HVR-L1 comprising the amino acid sequence of SEQ ID NO: 65; (e) HVR-L2 comprising the amino acid sequence of SEQ ID NO: 66; and (f) HVR-L3 comprising the amino acid sequence of SEQ ID NO: 67. In another aspect, the invention provides an immunoconjugate comprising an antibody that comprises (a) HVR-H1 comprising the amino acid sequence of SEQ ID NO: 80; (b) HVR-H2 comprising the amino acid sequence of SEQ ID NO: 81; (c) HVR-H3 comprising the amino acid sequence of SEQ ID NO: 82; (d) HVR-L1 comprising the amino acid sequence of SEQ ID NO: 83; (e) HVR-L2 comprising the amino acid sequence of SEQ ID NO: 84; and (f) HVR-L3 comprising the amino acid sequence of SEQ ID NO: 85.

In any of the above embodiments, an anti-HER2 antibody of an immunoconjugate is humanized. In one embodiment, an anti-HER2 antibody of an immunoconjugate comprises HVRs as in any of the above embodiments, and further comprises a human acceptor framework, e.g. a human immunoglobulin framework or a human consensus framework.

In another aspect, an anti-HER2 antibody of an immunoconjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 64 or 14. In certain embodiments, a VH sequence having at least 90%, 91%, 92%, 93%, 94%, 95%, 96%, 97%, 98%, or 99% identity to the amino acid sequence of SEQ ID NO: 64 or 14 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 64 or 14. In certain embodiments, a total of 1 to 5 amino acids have been substituted, inserted and/or deleted in SEQ ID NO: 64 or 14. In certain embodiments, substitutions, insertions, or deletions occur in regions outside the HVRs (i.e., in the FRs). Optionally, the anti-HER2 antibody comprises the VH sequence of SEQ ID NO: 64 or 14, including post-translational modifications of that sequence. In a particular embodiment, the VH comprises one, two or three HVRs selected from: (a) HVR-H1 comprising the amino acid sequence of SEQ ID NO: 68, (b) HVR-H2 comprising the amino acid sequence of SEQ ID NO: 69, and (c) HVR-H3 comprising the amino acid sequence of SEQ ID NO: 70. In another embodiment, the VH comprises one, two or three HVRs selected from: (a) HVR-H1 comprising the amino acid sequence of SEQ ID NO: 80, (b) HVR-H2 comprising the amino acid sequence of SEQ ID NO: 81, and (c) HVR-H3 comprising the amino acid sequence of SEQ ID NO: 82.

In another aspect, an anti-HER2 antibody of an immunoconjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 63 or 12. In certain embodiments, a VL sequence having at least 90%, 91%, 92%, 93%, 94%, 95%, 96%, 97%, 98%, or 99% identity to the amino acid sequence of SEQ ID NO: 63 or 12 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 63 or 12. In certain embodiments, a total of 1 to 5 amino acids have been substituted, inserted and/or deleted in SEQ ID NO: 63 or 12. In certain embodiments, the substitutions, insertions, or deletions occur in regions outside the HVRs (i.e., in the FRs). Optionally, the anti-HER2 antibody comprises the VL sequence of SEQ ID NO: 63 or 12, including post-translational modifications of that sequence. In a particular embodiment, the VL comprises one, two or three HVRs selected from (a) HVR-L1 comprising the amino acid sequence of SEQ ID NO: 65; (b) HVR-L2 comprising the amino acid sequence of SEQ ID NO: 66; and (c) HVR-L3 comprising the amino acid sequence of SEQ ID NO: 67. In a particular embodiment, the VL comprises one, two or three HVRs selected from (a) HVR-L1 comprising the amino acid sequence of SEQ ID NO: 83; (b) HVR-L2 comprising the amino acid sequence of SEQ ID NO: 84; and (c) HVR-L3 comprising the amino acid sequence of SEQ ID NO: 85.

In another aspect, an immunoconjugate comprising an anti-HER2 antibody is provided, wherein the antibody comprises a VH as in any of the embodiments provided above, and a VL as in any of the embodiments provided above.

In one embodiment, an immunoconjugate comprising an antibody is provided, wherein the antibody comprises the VH and VL sequences in SEQ ID NO: 64 and SEQ ID NO: 63, respectively, including post-translational modifications of those sequences. In one embodiment, an immunoconjugate comprising an antibody is provided, wherein the antibody comprises the VH and VL sequences in SEQ ID NO: 14 and SEQ ID NO: 12, respectively, including post-translational modifications of those sequences.

In a further aspect, provided herein are immunoconjugates comprising antibodies that bind to the same epitope as an anti-HER2 antibody provided herein. For example, in certain embodiments, an immunoconjugate is provided, comprising an antibody that binds to the same epitope as an anti-HER2 antibody comprising a VH sequence of SEQ ID NO: 64 and a VL sequence of SEQ ID NO: 63, respectively. In certain embodiments, an immunoconjugate is provided, comprising an antibody that binds to the same epitope as an anti-HER2 antibody comprising a VH sequence of SEQ ID NO: 14 and a VL sequence of SEQ ID NO: 12, respectively.

In a further aspect of the invention, an anti-HER2 antibody of an immunoconjugate according to any of the above embodiments is a monoclonal antibody, including a human antibody.

In one embodiment, an anti-HER2 antibody of an immunoconjugate is an antibody fragment, e.g., a Fv, Fab, Fab', scFv, diabody, or F(ab')$_2$ fragment. In another embodiment, an immunoconjugate comprises an antibody that is a substantially full length antibody, e.g., an IgG1 antibody, IgG2a antibody or other antibody class or isotype as defined herein.

In a further aspect, an anti-HER2 antibody of an immunoconjugate according to any of the above embodiments may incorporate any of the features, singly or in combination, as described in (1) to (7) below.

1. Antibody Affinity

In certain embodiments, an antibody provided herein has a dissociation constant (Kd) of ≤1 μM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody.

In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Ly6E, STEAP1, CD79b, MUC16, or HER2 and the other is for any other antigen. In certain embodiments, one of the binding specificities is for HER2 and the other is for CD3. See, e.g., U.S. Pat. No. 5,821,337. In certain embodiments, bispecific antibodies may bind to two different epitopes of an antigen. Bispecific antibodies may also be used to localize cytotoxic agents to cells which express antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5): 1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to a first antigen, such as Ly6E, STEAP1, CD79b, HER2, or MUC16, as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., a "THIOMAB™," in which one or more residues of an antibody are substituted with cysteine residues. In particular embodiments, the substituted residues occur at sites of the antibody that are available for conjugation. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: K149C (Kabat numbering) of the light chain; V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

An exemplary V205C cysteine engineered light chain is shown in SEQ ID NO: 76. The V205C cysteine engineered light chain may be fused to the C-terminus of a light chain variable region described herein and paired with a heavy chain to make a cysteine-engineered antibody.

An exemplary K149C cysteine engineered light chain is shown in SEQ ID NO: 78. The V205C cysteine engineered light chain may be fused to the C-terminus of a light chain variable region described herein and paired with a heavy chain to make a cysteine-engineered antibody.

An exemplary A118C cysteine engineered heavy chain is shown in SEQ ID NO: 77. The A118C cysteine engineered light chain may be fused to the C-terminus of a light chain variable region described herein and paired with a heavy chain to make a cysteine-engineered antibody.

An exemplary S400C cysteine engineered heavy chain is shown in SEQ ID NO: 79. The A118C cysteine engineered light chain may be fused to the C-terminus of a light chain variable region described herein and paired with a heavy chain to make a cysteine-engineered antibody.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

C. Assays

Antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to antigen (such as Ly6E, STEAP1, CD79b, HER2, or MUC16). In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized antigen (such as Ly6E, STEAP1, CD79b, HER2, or MUC16) is incubated in a solution comprising a first labeled antibody that binds to the antigen (e.g., any of the antibodies described herein) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to antigen. See Harlow and Lane (1988) *Antibodies: A Laboratory Manual* ch. 14 (Cold Spring Harbor Laboratory, Cold Spring Harbor, N.Y.).

D. Immunoconjugates

The invention also provides immunoconjugates comprising any antibody provided herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

$$\text{Ab-(L-D)}_p \qquad \qquad \text{I}$$

where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linker-Drug Moieties

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

In some embodiments, the drug portion of a linker-drug moiety comprises 1-(chloromethyl)-2,3-dihydro-1H-benzo[e]indole (CBI). The 5-amino-1-(chloromethyl)-1,2-dihydro-3H-benz[e]indole (amino CBI) class of DNA minor groove alkylators are potent cytotoxins (Atwell, et al (1999) J. Med. Chem., 42:3400), and have been utilized as effector units in a number of classes of prodrugs designed for cancer therapy. These have included antibody conjugates, (Jeffrey, et al. (2005) J. Med. Chem., 48:1344), prodrugs for gene therapy based on nitrobenzyl carbamates (Hay, et al (2003) J. Med. Chem. 46:2456) and the corresponding nitro-CBI derivatives as hypoxia-activated prodrugs (Tercel, et al (2011) Angew. Chem., Int. Ed., 50:2606-2609). In some embodiments, the drug portion of a linker-drug moiety comprises a 1-(chloromethyl)-2,3-dihydro-1H-benzo[e]indole (CBI) dimer. In some embodiments, the linker-drug moiety comprises a CBI/pyrrolo[2,1-c][1,4]benzodiazepine (PBD) dimer.

In some embodiments, a linker-drug intermediate for forming an immunoconjugate of the invention has the structure (LD-1):
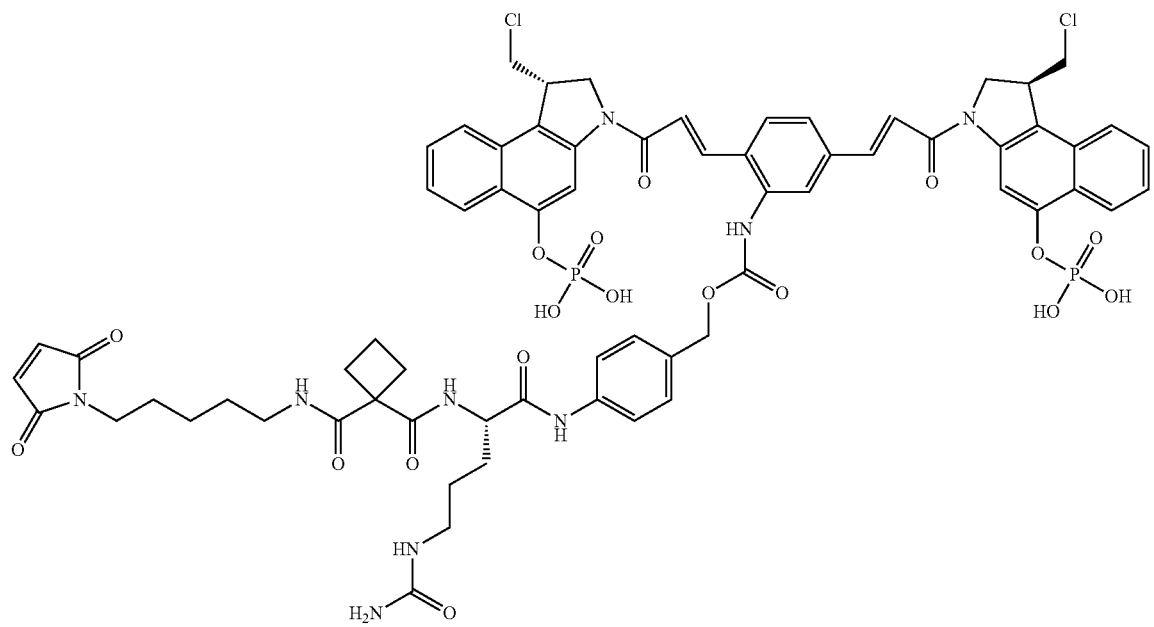 [SMILES: NC(=O)NCCC[C@H](NC(=O)C1(C(=O)NCCCCCN2C(=O)C=CC2=O)CCC1)C(=O)Nc1ccc(COC(=O)Nc2cc(/C=C/C(=O)N3C[C@@H](CCl)c4c3cc(OP(=O)(O)O)c3ccccc43)ccc2/C=C/C(=O)N2C[C@@H](CCl)c3c2cc(OP(=O)(O)O)c2ccccc32)cc1]
In some embodiments, a linker-drug intermediate for forming an immunoconjugate of the invention has the structure (LD-2):
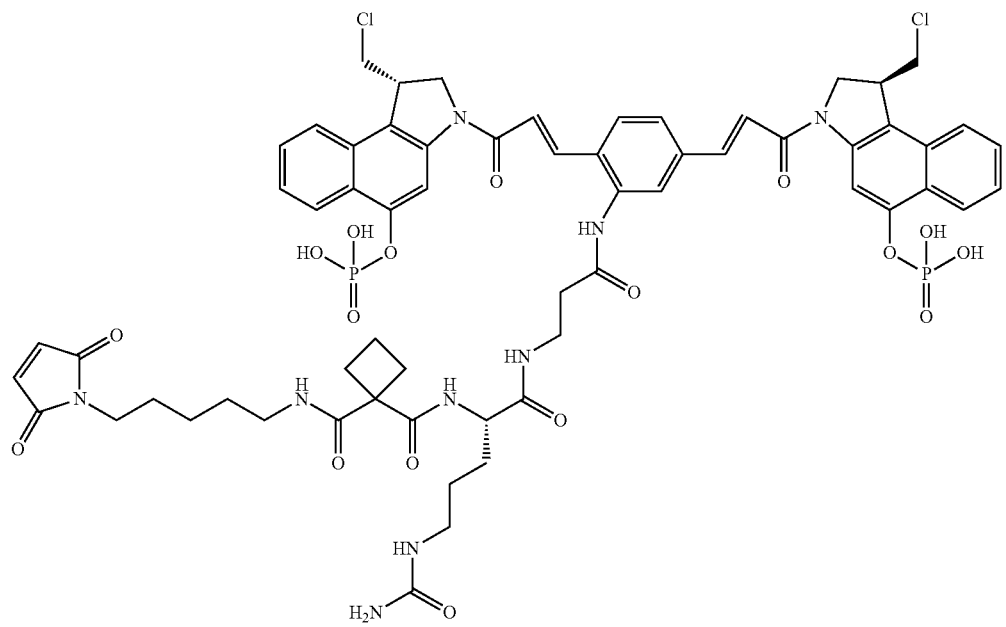 [SMILES: NC(=O)NCCC[C@H](NC(=O)C1(C(=O)NCCCCCN2C(=O)C=CC2=O)CCC1)C(=O)NCCC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21]

In some embodiments, a linker-drug intermediate for forming an immunoconjugate of the invention has the structure (LD-3):
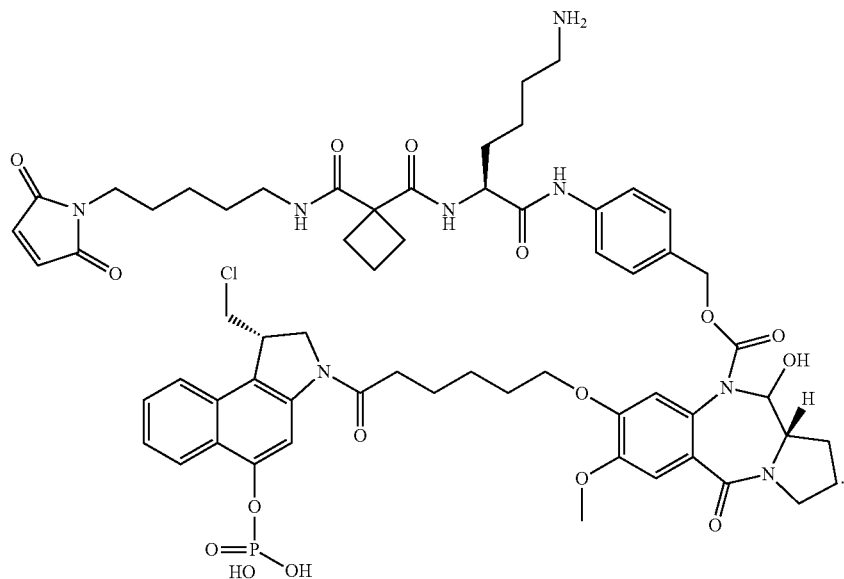
In some embodiments, an antibody-drug conjugate has the structure (I):
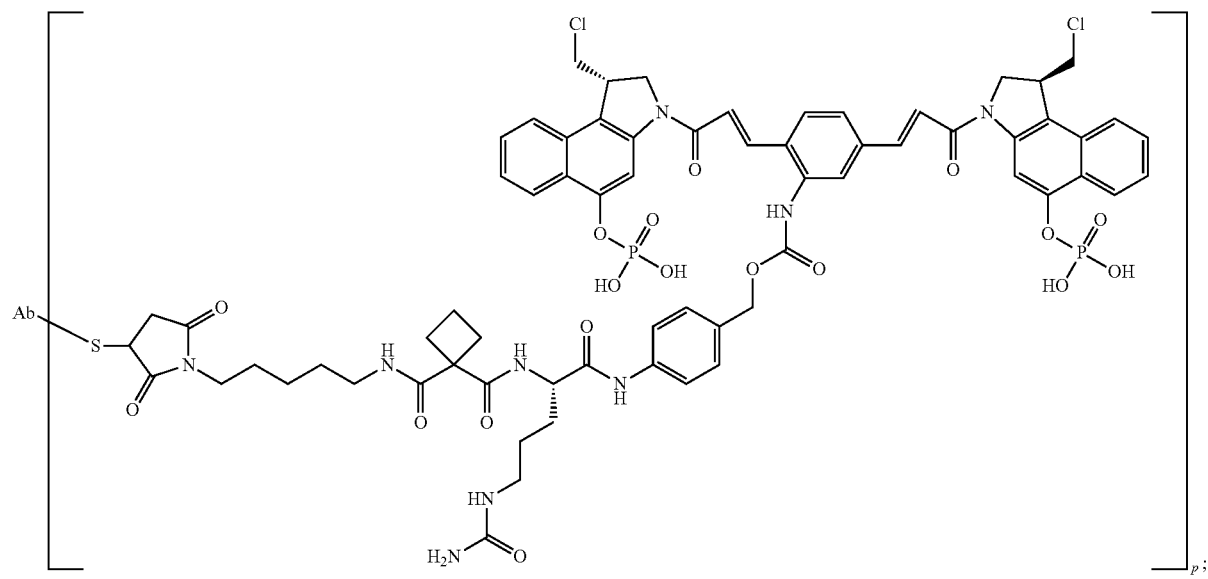
wherein Ab is the antibody and p is from 1 to 4. In some embodiments, p is from 1 to 2. In some embodiments, p is about 2.

In some embodiments, an antibody-drug conjugate has the structure (II):

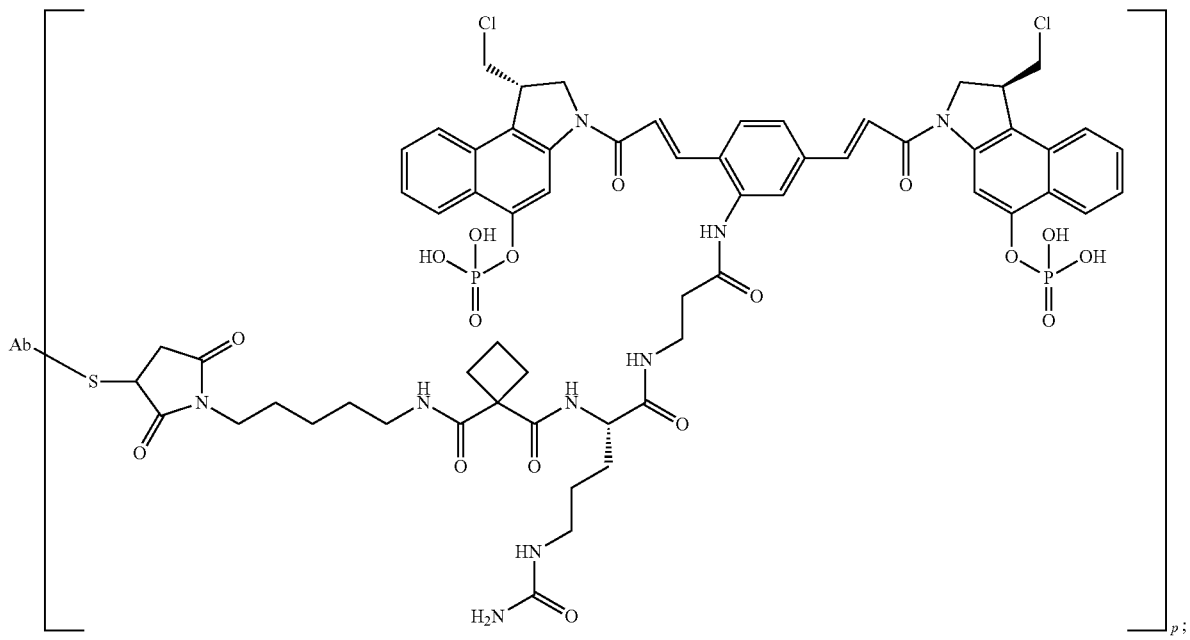

wherein Ab is the antibody and p is from 1 to 4. In some embodiments, p is from 1 to 2. In some embodiments, p is about 2.

In some embodiments, an antibody-drug conjugate has the structure (III):

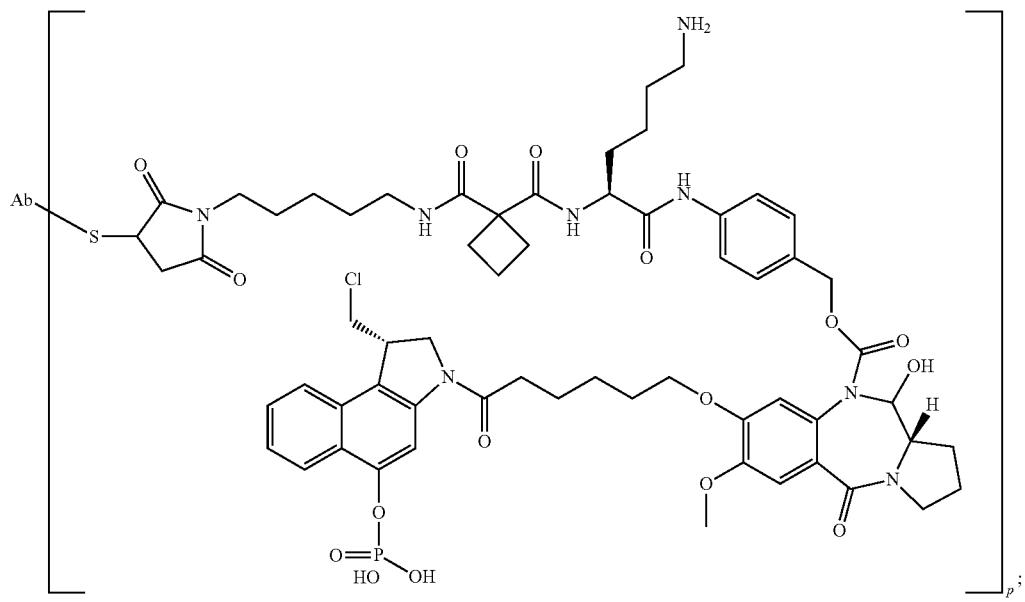

wherein Ab is the antibody and p is from 1 to 4. In some embodiments, p is from 1 to 2. In some embodiments, p is about 2.

In some embodiments, the antibody (Ab) is an antibody that binds an antigen selected from Ly6E, STEAP1, CD79b, HER2, and MUC16. In some embodiments, the antibody (Ab) is an antibody described herein.

b) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

c) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

E. Methods and Compositions for Diagnostics and Detection

In certain embodiments, any of the antibodies provided herein is useful for detecting the presence of antigen in a biological sample. The term "detecting" as used herein encompasses quantitative or qualitative detection. A "biological sample" comprises, e.g., a cell or tissue (e.g., biopsy material, including cancerous or potentially cancerous breast tissue).

In one embodiment, an antibody described herein for use in a method of diagnosis or detection is provided. In a further aspect, a method of detecting the presence of an antigen (such as Ly6E, STEAP1, CD79b, HER2, or MUC16) in a biological sample is provided. In certain embodiments, the method comprises contacting the biological sample with an antibody described herein under conditions permissive for binding of the antibody to the antigen, and detecting whether a complex is formed between the antibody and the antigen in the biological sample. Such method may be an in vitro or in vivo method. In one embodiment, an antibody described herein is used to select subjects eligible for therapy with an immunoconjugate described herein, e.g. where the antigen (such as Ly6E, STEAP1, CD79b, HER2, or MUC16) is a biomarker for selection of patients. In a further embodiment, the biological sample is a cell or tissue.

In a further embodiment, an antibody described herein is used in vivo to detect, e.g., by in vivo imaging, an antigen-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., The Oncologist 12:1379-1389 (2007) and Verel et al., J. Nucl. Med. 44:1271-1281 (2003). In such embodiments, a method is provided for detecting an antigen-positive cancer in a subject, the method comprising administering a labeled antibody to a subject having or suspected of having an antigen-positive cancer, and detecting the labeled antibody in the subject, wherein detection of the labeled antibody indicates an antigen-positive cancer in the subject. In certain of such embodiments, the labeled antibody comprises an antibody described herein conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr. In some embodiments, the antigen is selected from Ly6E, STEAP1, CD79b, HER2, and MUC16.

In further embodiments, a method of diagnosis or detection comprises contacting a first antibody immobilized to a substrate with a biological sample to be tested for the presence of the antigen, exposing the substrate to a second antibody, and detecting whether the second antibody is bound to a complex between the first antibody and the antigen in the biological sample. A substrate may be any supportive medium, e.g., glass, metal, ceramic, polymeric beads, slides, chips, and other substrates. In certain embodiments, a biological sample comprises a cell or tissue.

In certain embodiments, the first or second antibody is any of the antibodies described herein. In certain embodiments, labeled antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an antibody or immunoconjugate as described herein (such as an anti-Ly6E antibody of immunoconjugate) are prepared by mixing such antibody or immunoconjugate having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the immunoconjugates provided herein may be used in methods, e.g., therapeutic methods.

In one aspect, an anti-Ly6E antibody or immunoconjugate provided herein is used in a method of inhibiting proliferation of a Ly6E-positive cell, the method comprising exposing the cell to the anti-Ly6E antibody or immunoconjugate under conditions permissive for binding of the anti-Ly6E antibody or immunoconjugate to Ly6E on the surface of the cell, thereby inhibiting the proliferation of the cell. In certain embodiments, the method is an in vitro or an in vivo method. In some embodiments, the cell is a breast cancer cell, pancreatic cancer cell, colon cancer cell, colorectal cancer cell, melanoma cell, ovarian cancer cell, non-small cell lung cancer cell (either squamous and/or non-squamous), or gastric cancer cell.

In one aspect, an anti-STEAP1 antibody or immunoconjugate provided herein is used in a method of inhibiting proliferation of a STEAP1-positive cell, the method comprising exposing the cell to the anti-STEAP1 antibody or immunoconjugate under conditions permissive for binding of the anti-STEAP1 antibody or immunoconjugate to STEAP1 on the surface of the cell, thereby inhibiting the proliferation of the cell. In certain embodiments, the method is an in vitro or an in vivo method. In some embodiments, the cell is a prostate cancer cell, lung cancer cell, colon cancer cell, bladder cancer cell, ovarian cancer cell, or Ewing's sarcoma cell.

In one aspect, an anti-CD79b antibody or immunoconjugate provided herein is used in a method of inhibiting proliferation of a CD79b-positive cell, the method comprising exposing the cell to the anti-CD79b antibody or immunoconjugate under conditions permissive for binding of the anti-CD79b antibody or immunoconjugate to CD79b on the surface of the cell, thereby inhibiting the proliferation of the cell. In certain embodiments, the method is an in vitro or an in vivo method. In some embodiments, the cell is a lymphoma cell, non-Hogkins lymphoma (NHL) cell, chronic lymphocytic leukemia (CLL) cell, small lymphocytic lymphoma cell, leukemia cell, hairy cell leukemia (HCL) cell, acute lymphocytic leukemia (ALL) cell, Burkitt's lymphoma cell, or mantle cell lymphoma cell.

In one aspect, an anti-MUC16 antibody or immunoconjugate provided herein is used in a method of inhibiting proliferation of a MUC16-positive cell, the method comprising exposing the cell to the anti-MUC16 antibody or immunoconjugate under conditions permissive for binding of the anti-MUC16 antibody or immunoconjugate to MUC16 on the surface of the cell, thereby inhibiting the proliferation of the cell. In certain embodiments, the method is an in vitro or an in vivo method. In some embodiments, the cell is an ovarian cancer cell, endometrial cancer cell, non-small cell lung cancer cell (either squamous and/or non-squamous), pancreatic cancer cell, or breast cancer cell, including a Her2 negative breast cancer cell and/or triple negative breast cancer cell.

In one aspect, an anti-HER2 antibody or immunoconjugate provided herein is used in a method of inhibiting proliferation of a HER2-positive cell, the method comprising exposing the cell to the anti-HER2 antibody or immunoconjugate under conditions permissive for binding of the anti-HER2 antibody or immunoconjugate to HER2 on the surface of the cell, thereby inhibiting the proliferation of the cell. In certain embodiments, the method is an in vitro or an in vivo method. In some embodiments, the cell is a breast cancer cell or a gastric cancer cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602, 677. The assay may be conducted in 96- or 384-well format, making it amenable to automated high-throughput screening (HTS). See Cree et al. (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an immunoconjugate for use as a medicament is provided. In further aspects, an anti-Ly6E immunoconjugate for use in a method of treatment is provided. In certain embodiments, an anti-Ly6E immunoconjugate for use in treating Ly6E-positive cancer is provided. In certain embodiments, the invention provides an anti-Ly6E immunoconjugate for use in a method of treating an individual having a Ly6E-positive cancer, the method comprising administering to the individual an effective amount of the anti-Ly6E immunoconjugate. In one such embodiment, the method further comprises administering to the individual an effective amount of at least one additional therapeutic agent, e.g., as described below.

In a further aspect, the invention provides for the use of an anti-Ly6E immunoconjugate in the manufacture or preparation of a medicament. In one embodiment, the medicament is for treatment of Ly6E-positive cancer. In a further embodiment, the medicament is for use in a method of treating Ly6E-positive cancer, the method comprising administering to an individual having Ly6E-positive cancer an effective amount of the medicament. In one such embodiment, the method further comprises administering to the individual an effective amount of at least one additional therapeutic agent, e.g., as described below.

In a further aspect, the invention provides a method for treating Ly6E-positive cancer. In one embodiment, the method comprises administering to an individual having such Ly6E-positive cancer an effective amount of an anti-Ly6E immunoconjugate. In one such embodiment, the method further comprises administering to the individual an effective amount of at least one additional therapeutic agent, as described below.

A Ly6E-positive cancer according to any of the above embodiments may be, e.g., Ly6E-positive breast cancer, Ly6E-positive metastatic breast cancer, including Ly6E-positive/Her2 negative breast cancers and/or Ly6E-positive/triple negative breast cancers, Ly6E-positive pancreatic cancer, Ly6E-positive colon cancer, Ly6E-positive colorectal cancer, Ly6E-positive melanoma, Ly6E-positive ovarian cancer, Ly6E-positive non-small cell lung cancer (either squamous and/or non-squamous), or Ly6E-positive gastric cancer.

In another aspect, an immunoconjugate for use as a medicament is provided. In further aspects, an anti-STEAP1 immunoconjugate for use in a method of treatment is provided. In certain embodiments, an anti-STEAP1 immunoconjugate for use in treating STEAP1-positive cancer is provided. In certain embodiments, the invention provides an anti-STEAP1 immunoconjugate for use in a method of treating an individual having a STEAP1-positive cancer, the method comprising administering to the individual an effective amount of the anti-STEAP1 immunoconjugate. In one such embodiment, the method further comprises administering to the individual an effective amount of at least one additional therapeutic agent, e.g., as described below.

In a further aspect, the invention provides for the use of an anti-STEAP1 immunoconjugate in the manufacture or preparation of a medicament. In one embodiment, the medicament is for treatment of STEAP1-positive cancer. In a further embodiment, the medicament is for use in a method of treating STEAP1-positive cancer, the method comprising administering to an individual having STEAP1-positive cancer an effective amount of the medicament. In one such embodiment, the method further comprises administering to the individual an effective amount of at least one additional therapeutic agent, e.g., as described below.

In a further aspect, the invention provides a method for treating STEAP1-positive cancer. In one embodiment, the method comprises administering to an individual having such STEAP1-positive cancer an effective amount of an anti-STEAP1 immunoconjugate. In one such embodiment, the method further comprises administering to the individual an effective amount of at least one additional therapeutic agent, as described below.

A STEAP1-positive cancer according to any of the above embodiments may be, e.g., STEAP1-positive prostate cancer, STEAP1-positive lung cancer, STEAP1-positive colon cancer, STEAP1-positive bladder cancer, STEAP1-positive ovarian cancer, or STEAP1-positive Ewing's sarcoma.

In another aspect, an immunoconjugate for use as a medicament is provided. In further aspects, an anti-CD79b immunoconjugate for use in a method of treatment is provided. In certain embodiments, an anti-CD79b immunoconjugate for use in treating CD79b-positive cancer is provided. In certain embodiments, the invention provides an anti-CD79b immunoconjugate for use in a method of treating an individual having a CD79b-positive cancer, the method comprising administering to the individual an effective amount of the anti-CD79b immunoconjugate. In one such embodiment, the method further comprises administering to the individual an effective amount of at least one additional therapeutic agent, e.g., as described below.

In a further aspect, the invention provides for the use of an anti-CD79b immunoconjugate in the manufacture or preparation of a medicament. In one embodiment, the medicament is for treatment of CD79b-positive cancer. In a further embodiment, the medicament is for use in a method of treating CD79b-positive cancer, the method comprising administering to an individual having CD79b-positive cancer an effective amount of the medicament. In one such embodiment, the method further comprises administering to the individual an effective amount of at least one additional therapeutic agent, e.g., as described below.

In a further aspect, the invention provides a method for treating CD79b-positive cancer. In one embodiment, the method comprises administering to an individual having such CD79b-positive cancer an effective amount of an anti-CD79b immunoconjugate. In one such embodiment, the method further comprises administering to the individual an effective amount of at least one additional therapeutic agent, as described below.

A CD79b-positive cancer according to any of the above embodiments may be, e.g., CD79b-positive lymphoma, CD79b-positive non-Hogkins lymphoma (NHL), CD79b-positive aggressive NHL, CD79b-positive relapsed aggressive NHL, CD79b-positive relapsed indolent NHL, CD79b-positive refractory NHL, CD79b-positive refractory indolent NHL, CD79b-positive chronic lymphocytic leukemia (CLL), CD79b-positive small lymphocytic lymphoma, CD79b-positive leukemia, CD79b-positive hairy cell leukemia (HCL), CD79b-positive acute lymphocytic leukemia (ALL), CD79b-positive Burkitt's lymphoma, and CD79b-positive mantle cell lymphoma.

In another aspect, an immunoconjugate for use as a medicament is provided. In further aspects, an anti-MUC16 immunoconjugate for use in a method of treatment is provided. In certain embodiments, an anti-MUC16 immunoconjugate for use in treating MUC16-positive cancer is provided. In certain embodiments, the invention provides an anti-MUC16 immunoconjugate for use in a method of treating an individual having a MUC16-positive cancer, the method comprising administering to the individual an effective amount of the anti-MUC16 immunoconjugate. In one such embodiment, the method further comprises administering to the individual an effective amount of at least one additional therapeutic agent, e.g., as described below.

In a further aspect, the invention provides for the use of an anti-MUC16 immunoconjugate in the manufacture or preparation of a medicament. In one embodiment, the medicament is for treatment of MUC16-positive cancer. In a further embodiment, the medicament is for use in a method of treating MUC16-positive cancer, the method comprising administering to an individual having MUC16-positive cancer an effective amount of the medicament. In one such embodiment, the method further comprises administering to the individual an effective amount of at least one additional therapeutic agent, e.g., as described below.

In a further aspect, the invention provides a method for treating MUC16-positive cancer. In one embodiment, the method comprises administering to an individual having such MUC16-positive cancer an effective amount of an anti-MUC16 immunoconjugate. In one such embodiment, the method further comprises administering to the individual an effective amount of at least one additional therapeutic agent, as described below.

A MUC16-positive cancer according to any of the above embodiments may be, e.g., MUC16-positive ovarian cancer, MUC16-positive endometrial cancer, MUC16-positive non-small cell lung cancer (either squamous and/or non-squamous), MUC16-positive pancreatic cancer, or MUC16-positive breast cancer, such as MUC16-positive metastatic breast cancer, including MUC16-positive Her2 negative breast cancer and/or MUC16-positive triple negative breast cancer.

In another aspect, an anti-HER2 immunoconjugate for use as a medicament is provided. In further aspects, an anti-HER2 immunoconjugate for use in a method of treatment is provided. In certain embodiments, an anti-HER2 immunoconjugate for use in treating HER2-positive cancer is provided. In certain embodiments, the invention provides an anti-HER2 immunoconjugate for use in a method of treating an individual having a HER2-positive cancer, the method comprising administering to the individual an effective amount of the anti-HER2 immunoconjugate. In one such embodiment, the method further comprises administering to the individual an effective amount of at least one additional therapeutic agent, e.g., as described below.

In a further aspect, the invention provides for the use of an anti-HER2 immunoconjugate in the manufacture or preparation of a medicament. In one embodiment, the medicament is for treatment of HER2-positive cancer. In a further embodiment, the medicament is for use in a method of treating HER2-positive cancer, the method comprising administering to an individual having HER2-positive cancer an effective amount of the medicament. In one such embodiment, the method further comprises administering to the individual an effective amount of at least one additional therapeutic agent, e.g., as described below.

In a further aspect, the invention provides a method for treating HER2-positive cancer. In one embodiment, the method comprises administering to an individual having such HER2-positive cancer an effective amount of an anti-HER2 immunoconjugate. In one such embodiment, the method further comprises administering to the individual an effective amount of at least one additional therapeutic agent, as described below.

A HER2-positive cancer according to any of the above embodiments may be, e.g., HER2-positive breast cancer or HER2-positive gastric cancer. In some embodiments, HER2-positive cancer has an immunohistochemistry (IHC) score of 2+ or 3+ and/or an in situ hybridization (ISH) amplification ratio≥2.0.

An "individual," "patient," or "subject" according to any of the above embodiments may be a human.

In a further aspect, the invention provides pharmaceutical formulations comprising any of the immunoconjugates provided herein, e.g., for use in any of the above therapeutic methods. In one embodiment, a pharmaceutical formulation comprises any of the immunoconjugates provided herein and a pharmaceutically acceptable carrier. In another embodiment, a pharmaceutical formulation comprises any of the immunoconjugates provided herein and at least one additional therapeutic agent, e.g., as described below.

Antibodies or immunoconjugates of the invention can be used either alone or in combination with other agents in a therapy. For instance, an immunoconjugate of the invention may be co-administered with at least one additional therapeutic agent.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an antibody.

H. Articles of Manufacture

Articles of manufacture, or "kits", containing an immunoconjugate described herein for the treatment methods herein are provided. The kit may comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold immunoconjugate or a formulation thereof which is effective for use in a treatment method herein, and may have a sterile access port (for example, the container may be an intravenous solution bag or a vial having a stopper pierceable by a hypodermic injection needle). The label or package insert indicates that the composition is used in a treatment method as described and claimed herein. The article of manufacture may also contain a further container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the immunoconjugate. For example, if the kit comprises a first composition comprising an immunoconjugate described herein and a second pharmaceutical formulation, the kit may further comprise directions for the simultaneous, sequential or separate administration of the first and second pharmaceutical compositions to a patient in need thereof.

In another embodiment, the kits are suitable for oral delivery of immunoconjugates, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

III. Examples

The following are examples of methods and compositions of the invention. It is understood that various other embodiments may be practiced, given the general description provided above.

Example 1

Production of Antibody Drug Conjugates

For larger scale antibody production, antibodies may be produced in CHO cells. Vectors coding for heavy chain and light chain may be transfected into CHO cells and IgG purified from cell culture media by standard column chromatography, such as protein A affinity chromatography.

The CBI-CBI dimer and CBI-PBD dimer peptidomimetic linker drug intermediates shown in Table 2 were synthesized as described below.

TABLE 2

CBI-CBI dimer and CBI-PBD dimer peptidomimetic linker drug intermediates

| LD No. | Structure | IUPAC Name |
|---|---|---|
| LD-1 | 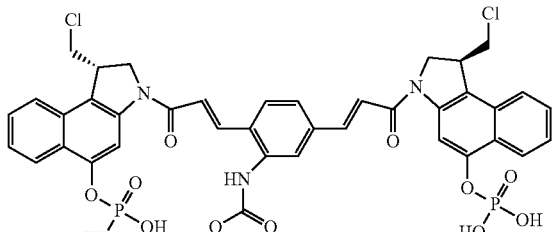 | 4-((S)-2-(1-((5-(2,5-dioxo-2,5-dihydro-1H-pyrrol-1-yl)pentyl)carbamoyl)cyclobutanecarboxamido)-5-ureidopentanamido)benzyl (2,5-bis((E)-3-((S)-1-(chloromethyl)-5-(phosphonooxy)-1H-benzo[e]indol-3(2H)-yl)-3-oxoprop-1-en-1-yl)phenyl)carbamate |

TABLE 2-continued

CBI-CBI dimer and CBI-PBD dimer peptidomimetic linker drug intermediates

| LD No. | Structure | IUPAC Name |
|---|---|---|
| LD-2 | 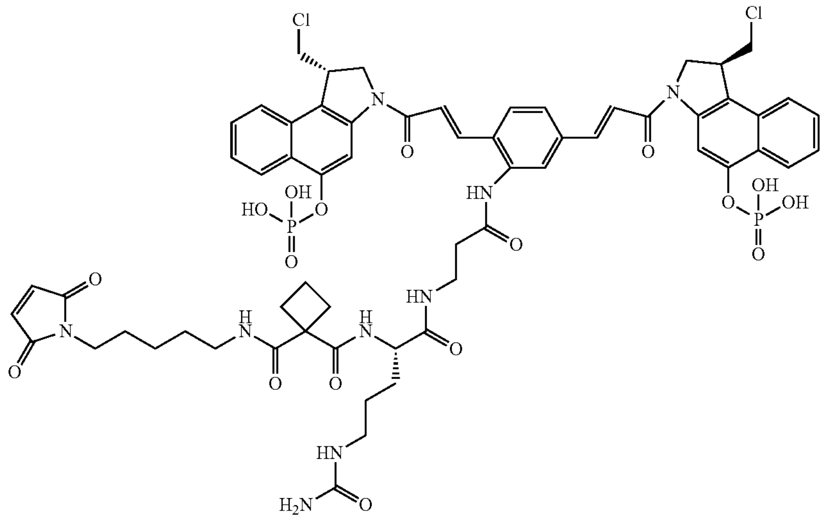 [SMILES: NC(=O)NCCC[C@H](NC(=O)C1(C(=O)NCCCCCN2C(=O)C=CC2=O)CCC1)C(=O)NCCC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21] | (1S,1'S)-3,3'-((2E,2'E)-3,3'-(2-(3-((S)-2-(1-((5-(2,5-dioxo-2,5-dihydro-1H-pyrrol-1-yl)pentyl)carbamoyl)cyclobutanecarboxamido)-5-ureidopentanamido)propanamido)-1,4-phenylene)bis(acryloyl))bis(1-(chloromethyl)-2,3-dihydro-1H-benzo[e]indole-5,3-diyl)bis(dihydrogen phosphate) |
| LD-3 | 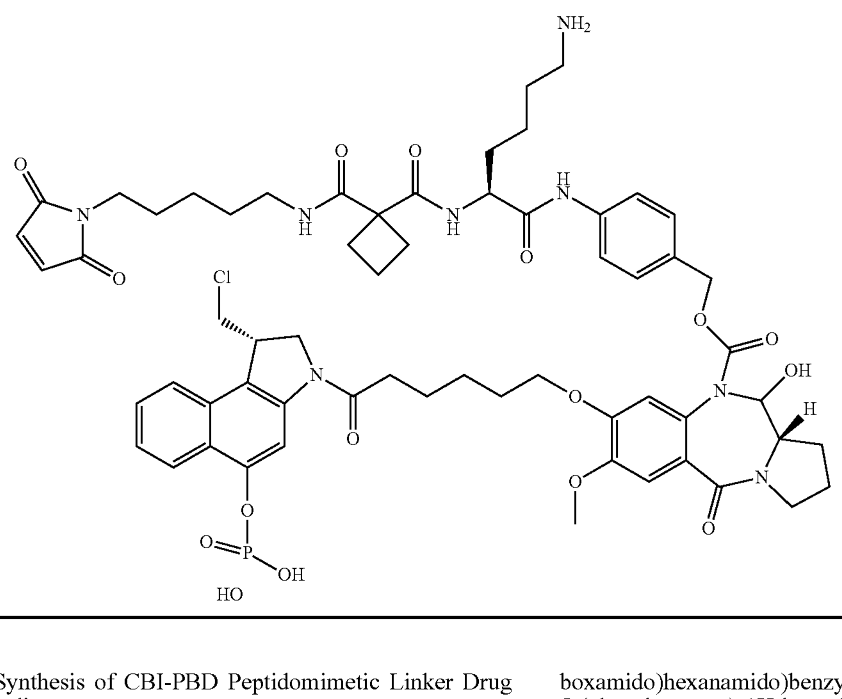 | (11aS)-4-((S)-6-amino-2-(1-((5-(2,5-dioxo-2,5-dihydro-1H-pyrrol-1-yl)pentyl)carbamoyl)cyclobutanecarboxamido)hexanamido)benzyl 8-((6-((S)-1-(chloromethyl)-5-(phosphonooxy)-1H-benzo[e]indol-3(2H)-yl)-6-oxohexyl)oxy)-11-hydroxy-7-methoxy-5-oxo-2,3,11,11a-tetrahydro-1H-benzo[e]pyrrolo[1,2-a][1,4]diazepine-10(5H)-carboxylate |

A. Synthesis of CBI-PBD Peptidomimetic Linker Drug Intermediate

The CBI-PBD dimer peptidomimetic linker-drug intermediate ((11aS)-4-((S)-6-amino-2-(1-((5-(2,5-dioxo-2,5-dihydro-1H-pyrrol-1-yl)pentyl)carbamoyl)cyclobutanecarboxamido)hexanamido)benzyl 8-((6-((S)-1-(chloromethyl)-5-(phosphonooxy)-1H-benzo[e]indol-3 (2H)-yl)-6-oxohexyl)oxy)-11-hydroxy-7-methoxy-5-oxo-2,3,11,11a-tetrahydro-1H-benzo[e]pyrrolo[1,2-a][1,4]diazepine-10 (5H)-carboxylate; LD-3) having the formula:

LD-3

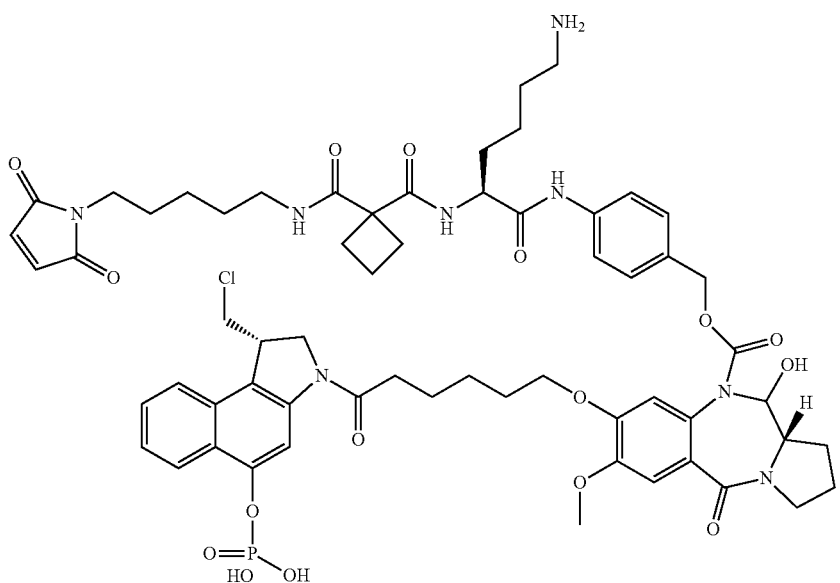

was synthesized as follows.

Step A: Synthesis of (S)-di-tert-butyl (1-(chloromethyl)-3-(2,2,2-trifluoroacetyl)-2,3-dihydro-1H-benzo[e]indol-5-yl) phosphate 1u

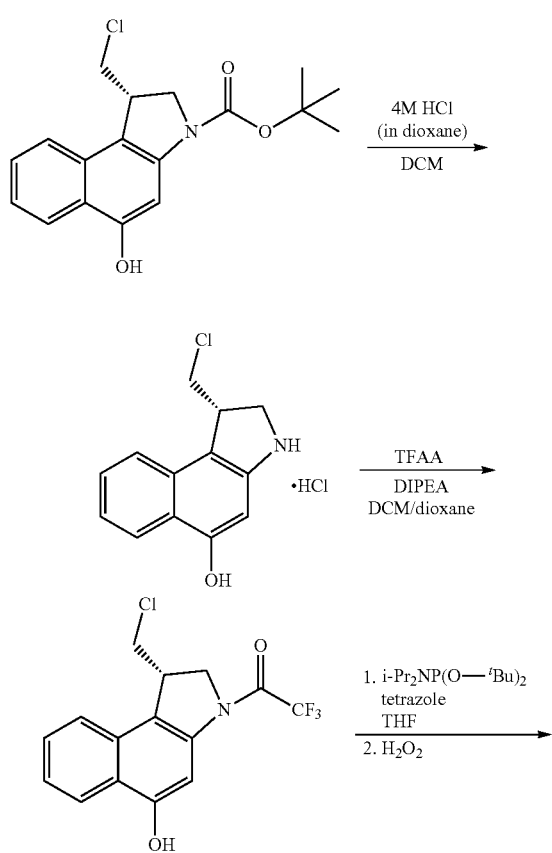

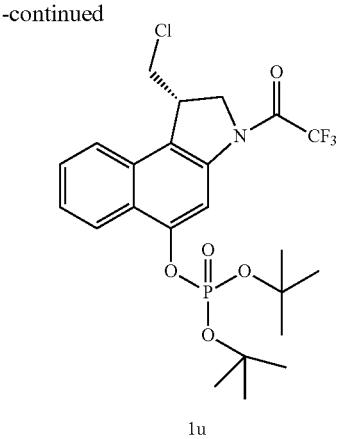

1u

To a stirred homogeneous solution of tert-butyl (S)-1-(chloromethyl)-5-hydroxy-1,2-dihydro-3H-benzo[e]indole-3-carboxylate (3.34 g, 10.0 mmol) in dry DCM (25 mL) at 20° C. under a nitrogen atmosphere was added 4M HCl in dioxane (12.5 mL, 50.0 mmol). After addition the reaction mixture was stirred at 20° C. under nitrogen for a further 20 h. The mixture was diluted with petroleum ether (250 mL) and stirred at 20° C. under nitrogen for 20 min. Solvents were decanted and the procedure was repeated once more with petroleum ether (250 mL). The resulting solid was dried under vacuum at 25° C. for 1 h to give (S)-1-(chloromethyl)-2,3-dihydro-1H-benzo[e]indol-5-ol hydrochloride (2.7 g, 100%); $^1$H NMR [(CD$_3$)$_2$SO] δ 10.80 (s, 1 H), 8.15 (d, J=8.3 Hz, 1 H), 7.87 (d, J=8.2 Hz, 1 H), 7.58 (br t, J=7.5 Hz, 1 H), 7.43 (br t, J=7.4 Hz, 1 H), 6.81 (s, 1 H), 4.27-4.17 (m, 1 H), 4.01 (dd, J=11.0, 3.2 Hz, 1 H), 3.93-3.74 (m, 3 H), 2 protons not observed. The crude product was used for the next step without further purification.

To a stirred heterogeneous mixture of (S)-1-(chloromethyl)-2,3-dihydro-1H-benzo[e]indol-5-ol hydrochloride (2.7 g, 10.0 mmol) in dry DCM (10 mL) and dioxane (30 mL) at 0° C. under a nitrogen atmosphere was added trifluoroacetic anhydride (TFAA) (3.4 mL, 24.0 mmol), followed by diisopropylethylamine (DIPEA) (8.71 mL, 50.0 mmol). After addition the reaction mixture was stirred at 0° C. under nitrogen for a further 50 min. Ethyl acetate (400 mL) was added and 1N HCl (200 mL) were added at 0° C. and the mixture stirred for 20 min under nitrogen. The ethyl acetate layer was separated, washed successively with 1N HCl (200 mL) and water (2×200 mL), and then dried (MgSO₄) and evaporated under reduced pressure at a bath temperature of 25° C. to give (S)-1-(1-(chloromethyl)-5-hydroxy-1,2-dihydro-3H-benzo[e]indol-3-yl)-2,2,2-trifluoroethan-1-one (3.3 g, 100%) as a green-grey solid. This material was used for the next step without further purification.

To a stirred homogeneous solution of (S)-1-(1-(chloromethyl)-5-hydroxy-1,2-dihydro-3H-benzo[e]indol-3-yl)-2,2,2-trifluoroethan-1-one (3.3 g, 10.0 mmol) in dry THF (40 mL) at 20° C. under a nitrogen atmosphere was added di-tert-butyl-N,N-diisopropylphosphoramidite (4.31 mL, 13.0 mmol). After addition the reaction mixture was stirred at 20° C. under nitrogen for 5-10 min and then tetrazole (3% solution in CH₃CN, 38.0 mL, 13.0 mmol) was added dropwise over 17 min. The final reaction mixture was stirred further at 20° C. under nitrogen for 19 h. The mixture was cooled in an ice-bath and 30% H₂O₂ (11.3 mL, 100.0 mmol) was added. After addition the reaction mixture was stirred at 20° C. for a further 1 h 30 min. The mixture was diluted with ethyl acetate (300 mL) and 10% aqueous Na₂S₂O₃ (500 mL) at stirred at 0° C. for 20 min. The ethyl acetate layer was separated and washed successively with water (200 mL), saturated NaHCO₃ (200 mL), and water (200 mL) and then dried (MgSO₄) and evaporated under reduced pressure at a bath temperature of 25° C. to give an amber oil. Purification by chromatography on a silica gel (eluting with ethyl acetate:petroleum ether 1:3) gave 1u (4.7 g, 90%) as a colorless foamy solid, mp 39-42° C.; [α]$_D$–61.8° (c 1.02, CHCl₃). Anal. (C₂₃H₂₈ClF₃NO₅P) Calc: C, 52.93; H, 5.41; N, 2.68. Found: C, 53.05; H, 5.43; N, 2.80.

Step B: Synthesis of ((S)-1-(2-((((4-((S)-2-(((allyloxy)carbonyl)amino)-6-((tert-butoxycarbonyl)amino)hexanamido)benzyl)oxy)carbonyl)amino)-4-((6-((S)-1-(chloromethyl)-5-((di-tert-butoxyphosphoryl)oxy)-1,2-dihydro-3H-benzo[e]indol-3-yl)-6-oxohexyl)oxy)-5-methoxybenzoyl)pyrrolidin-2-yl)methyl acetate 3g

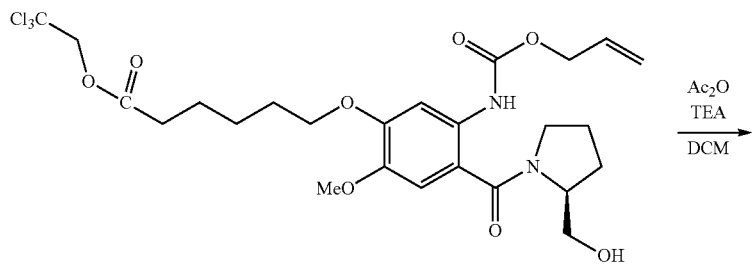

3a

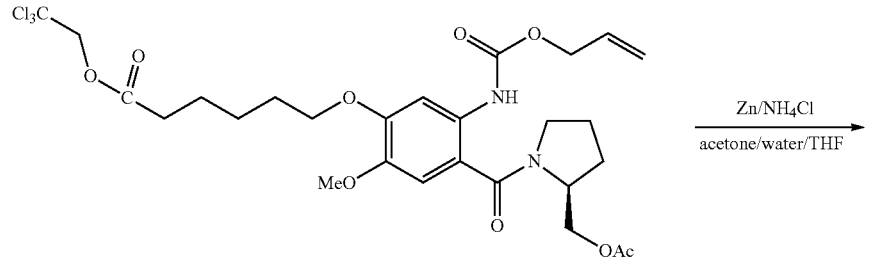

3b

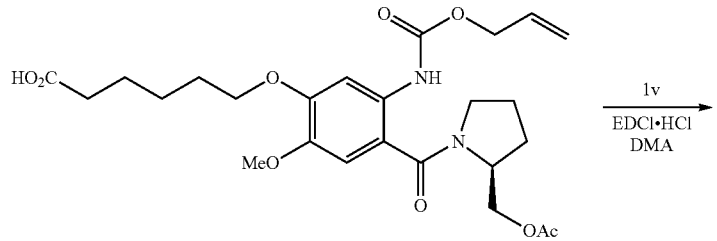

3c

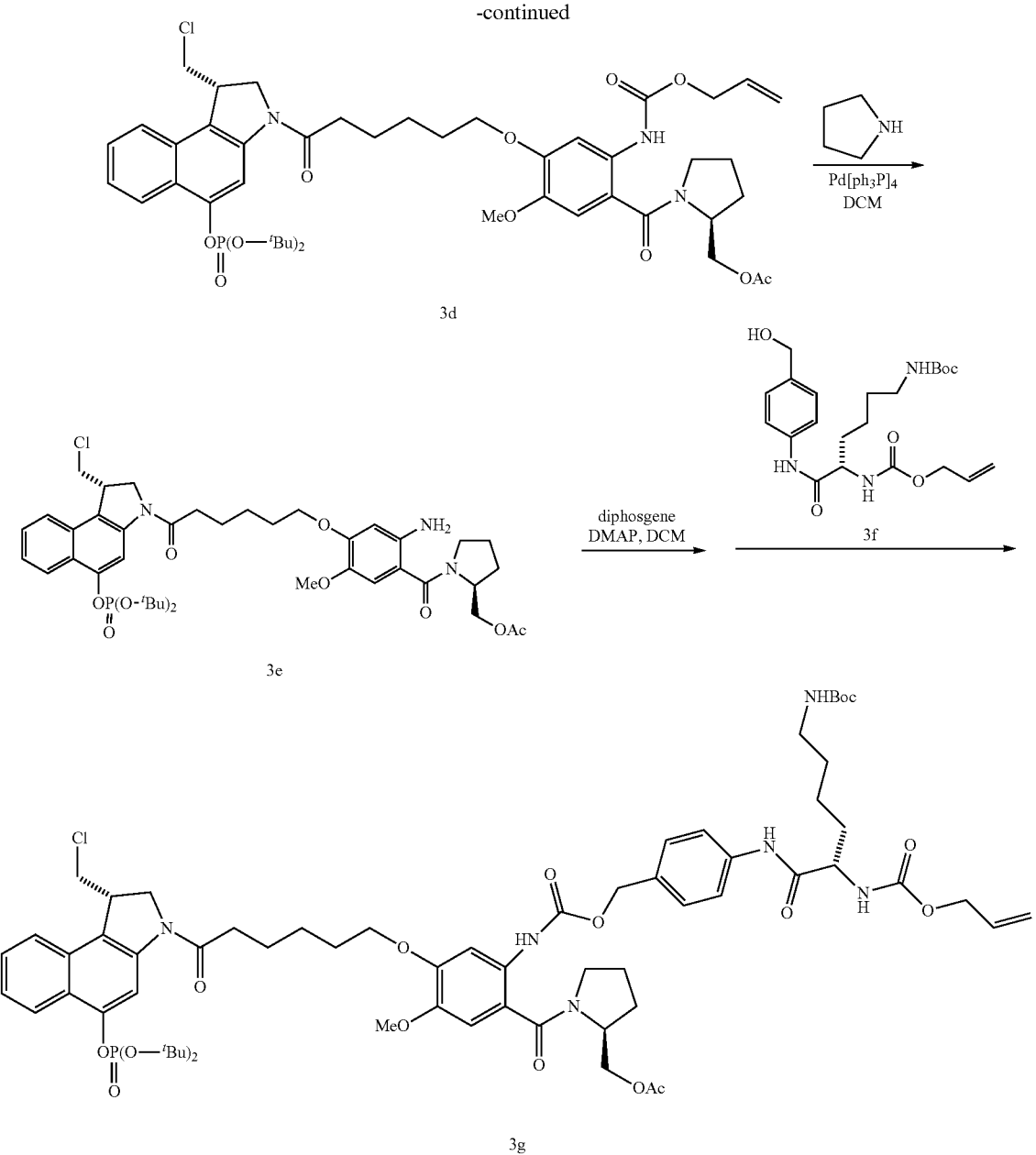

To a stirred solution of 2,2,2-trichloroethyl (S)-6-(5-(((allyloxy)carbonyl)amino)-4-(2-(hydroxymethyl)pyrrolidine-1-carbonyl)-2-methoxyphenoxy)hexanoate 3a (4.14 g, 6.95 mmol) (J. Med. Chem. 2003, 46, 2132-2151) in dry DCM (25 mL) was added acetic anhydride (3.30 mL, 34.8 mmol) and triethylamine (5.81 mL, 41.7 mmol). The mixture was stirred at 20° C. for 3 h 30 min. Dry MeOH (4.0 mL) was added and the mixture was stirred for 30 min. The mixture was partitioned between EtOAc (400 mL) and water (400 mL). The EtOAc layer was separated, washed with water (2×200 mL), and then dried (MgSO$_4$) and evaporated to give 2,2,2-trichloroethyl (S)-6-(4-(2-(acetoxymethyl)pyrrolidine-1-carbonyl)-5-(((allyloxy)carbonyl)amino)-2-methoxyphenoxy)hexanoate 3b (4.28 g, 96%) as an oil; [α]$_D$–57.4° (c 0.21, CHCl$_3$); $^1$H NMR [(CD$_3$)$_2$SO] δ 9.10 (s, 1 H), 7.17 (s, 1 H), 6.87 (s, 1 H), 6.01-5.87 (m, 1 H), 5.32 (dd, J=17.2, 1.5 Hz, 1 H), 5.21 (dd, J=10.4, 1.4 Hz, 1 H), 4.89 (s, 2 H), 4.54 (d, J=5.4 Hz, 2 H), 4.39-4.20 (m, 3 H), 3.93 (t, J=6.4 Hz, 2 H), 3.75 (s, 3 H), 3.46-3.27 (m, 2 H), 2.13-1.90 (m, 4 H), 1.89-1.60 (m, 7 H), 1.54-1.40 (m, 2 H), 2 protons obscured by DMSO peak. HRMS (ESI) m/z calc. for C$_{27}$H$_{36}$Cl$_3$N$_2$O$_9$: 637.1481, found: 637.1475 [MH$^+$]; calc. for C$_{27}$H$_{35}$Cl$_3$N$_2$NaO$_9$: 659.1300, found: 659.1303 [MNa$^+$]; calc. for C$_{27}$H$_{35}$Cl$_3$KN$_2$O$_9$: 675.1040, found: 675.1035 [MK$^+$].

To a stirred solution of 3b (4.27 g, 6.69 mmol) in acetone (75 mL), water (50 mL), and THF (30 mL) was added zinc powder (17.5 g, 268 mmol) and NH$_4$Cl (28.6 g, 535 mmol). The mixture was stirred at 20° C. under a nitrogen atmosphere for 42 h. Acetone (100 mL) was added, the mixture was stirred for 10 min, and the supernatant was decanted. The procedure was repeated twice and the combined supernatants were evaporated under reduced pressure to remove acetone and THF. The residue was diluted with water (50 mL) and acidified with aqueous 1N HCl to pH ca. 1. The acidic mixture was washed with petroleum ether (2×200 mL) and extracted with EtOAc (400 mL). The EtOAc extract was washed with water (200 mL) and dried (MgSO$_4$) and the solvent was evaporated to give (S)-6-(4-(2-(acetoxymethyl)pyrrolidine-1-carbonyl)-5-(((allyloxy)carbonyl)amino)-2-methoxyphenoxy)hexanoic acid 3c (2.72 g, 80%) as an oil; [α]$_D$ –73.5° (c 1.12, CHCl$_3$); $^1$H NMR [(CD$_3$)$_2$SO] δ 11.99 (s, exchangeable with D$_2$O, 1 H), 9.10 (s, exchangeable with D$_2$O, 1 H), 7.17 (s, 1 H), 6.87 (s, 1 H), 6.00-5.86 (m, 1 H), 5.32 (dd, J=17.2, 1.5 Hz, 1 H), 5.20 (dd, J=10.4, 1.5 Hz, 1 H), 4.57-4.52 (m, 2 H), 4.37-4.03 (m, 3 H), 3.93 (t, J=6.5 Hz, 2 H), 3.75 (s, 3 H), 3.40-3.10 (m, 2 H), 2.23 (t, J=7.3 Hz, 2 H), 2.07-1.93 (m, 4 H), 1.89-1.66 (m, 5 H), 1.62-1.49 (m, 2 H), 1.47-1.34 (m, 2 H). HRMS (ESI) m/z calc. for C$_{25}$H$_{35}$N$_2$O$_9$: 507.2337, found: 507.2340 [MH$^+$]; calc. for C$_{25}$H$_{34}$KN$_2$O$_9$: 545.1896, found: 545.1906 [MK$^+$]; calc. for C$_{25}$H$_{34}$N$_2$NaO$_9$: 529.2157, found: 529.2169 [MNa$^+$].

To a stirred solution of (S)-di-tert-butyl (1-(chloromethyl)-3-(2,2,2-trifluoroacetyl)-2,3-dihydro-1H-benzo[e]indol-5-yl) phosphate 1u (1.38 g, 2.64 mmol) in MeOH (10 mL) at 0° C. under a nitrogen atmosphere was added Cs$_2$CO$_3$ (1.03 g, 3.17 mmol). The mixture was stirred at 0° C. for 2 h 30 min and then partitioned between EtOAc (200 mL) and water (150 mL). The EtOAc layer was separated and washed again with water (100 mL), and then dried (MgSO$_4$) and evaporated under reduced pressure at a bathe temperature of 25° C. to give the (S)-di-tert-butyl (1-(chloromethyl)-2,3-dihydro-1H-benzo[e]indol-5-yl) phosphate 1v (1.17 g) as a pale yellow foamy solid which was treated with 3c (1.24 g, 2.45 mmol), EDCI.HCl (1.41 g, 7.35 mmol) and p-toluenesulfonic acid (84 mg, 0.49 mmol) in dry DMA (14 mL) at 0-20° C. for 22 h. The mixture was partitioned between EtOAc (400 mL) and water (300 mL). The EtOAc layer was separated and washed again with water (100 mL), and then dried (MgSO$_4$) and evaporated. Purification by chromatography on silica gel (eluting with EtOAc:petroleum ether 2:1) gave ((S)-1-(2-(((allyloxy)carbonyl)amino)-4-((6-((S)-1-(chloromethyl)-5-((di-tert-butoxyphosphoryl)oxy)-1,2-dihydro-3H-benzo[e]indol-3-yl)-6-oxohexyl)oxy)-5-methoxybenzoyl)pyrrolidin-2-yl)methyl acetate 3d (1.49 g, 66%) as a pale yellow foamy solid, mp 55-59° C.; [α]$_D$ –68.0° (c 1.00, CHCl$_3$); $^1$H NMR [(CD$_3$)$_2$SO] δ 9.10 (s, exchangeable with D$_2$O, 1 H), 8.56 (s, 1 H), 8.03 (d, J=8.1 Hz, 1 H), 7.92 (d, J=8.4 Hz, 1 H), 7.57 (t, J=8.1 Hz, 1 H), 7.47 (t, J=7.6 Hz, 1 H), 7.19 (s, 1 H), 6.86 (s, 1 H), 5.99-5.86 (m, 1 H), 5.32 (dd, J=17.2, 1.6 Hz, 1 H), 5.20 (dd, J=10.4, 1.5 Hz, 1 H), 4.53 (d, J=5.4 Hz, 2 H), 4.45-3.84 (m, 10 H), 3.74 (s, 3 H), 3.44-3.26 (m, 2 H), 2.68-2.47 (m, 2 H), 2.02 (br s, 3 H), 1.93-1.43 (m, 10 H), 1.474 and 1.469 (2 s, 18 H). HRMS (ESI) m/z calc. for C$_{46}$H$_{62}$ClN$_3$O$_{12}$P: 914.3754, found: 914.3749 [MH$^+$]; calc. for: C$_{46}$H$_{61}$ClKN$_3$O$_{12}$P: 952.3313, found: 952.3381 [MK$^+$]; calc. for C$_{46}$H$_{61}$ClN$_3$NaO$_{12}$P: 936.3574, found: 936.3589 [MNa$^+$].

To a stirred solution of 3d (548 mg, 0.60 mmol) in DCM (8 mL) at 20° C. under a nitrogen atmosphere was added Pd(Ph$_3$P)$_4$ (17.1 mg; 9.8% Pd) and pyrrolidine (0.49 mL, 6.00 mmol). The mixture was stirred at 20° C. for 30 min and then partitioned between EtOAc (200 mL) and water (150 mL). The EtOAc layer was separated and washed again with water (50 mL), and then dried (MgSO$_4$) and evaporated under reduced pressure at a bath temperature of 25° C. The crude product was purified by chromatography on silica gel (eluting with EtOAc:MeOH 50:1) to give ((S)-1-(2-amino-4-((6-((S)-1-(chloromethyl)-5-((di-tert-butoxyphosphoryl)oxy)-1,2-dihydro-3H-benzo[e]indol-3-yl)-6-oxohexyl)oxy)-5-methoxybenzoyl)pyrrolidin-2-yl)methyl acetate 3e (323 mg, 65%) as a pale yellow foamy solid, mp 46-49° C.; [α]$_D$ –85.2° (c 0.36, CHCl$_3$); $^1$H NMR [(CD$_3$)$_2$SO] δ 8.56 (s, 1 H), 8.04 (d, J=8.3 Hz, 1 H), 7.93 (d, J=8.4 Hz, 1 H), 7.58 (t, J=8.2 Hz, 1 H), 7.47 (t, J=8.1 Hz, 1 H), 6.67 (s, 1 H), 6.37 (s, 1 H), 5.09 (s, exchangeable with D$_2$O, 2 H), 4.46-3.85 (m, 10 H), 3.63 (s, 3 H), 3.52-3.34 (m, 2 H), 2.69-2.50 (m, 2 H), 2.08-1.94 (m, 1 H), 2.01 (s, 3 H), 1.91-1.61 (m, 7 H), 1.58-1.44 (m, 2 H), 1.476 and 1.470 (2 s, 18 H). HRMS (ESI) m/z calc. for C$_{42}$H$_{58}$ClN$_3$O$_{10}$P: 830.3522, found: 830.3543 [MH$^+$].

To a stirred solution of 3e (293 mg, 0.35 mmol) and DMAP (202 mg, 1.65 mmol) in dry DCM (7 mL) at 20° C. under a nitrogen atmosphere was added a solution of diphosgene in dry DCM (0.05 M, 6.7 mL, 0.33 mmol). The mixture was stirred for 25 min and then a solution of allyl tert-butyl (6-((4-(hydroxymethyl)phenyl)amino)-6-oxohexane-1,5-diyl)(S)-dicarbamate 3f (1.54 g, 3.54 mmol) in dry DCM (20 mL) was added. The mixture was stirred at 20° C. under a nitrogen atmosphere for 68 h and then partitioned between EtOAc (300 mL) and water (200 mL). The EtOAc layer was separated, washed again with water (100 mL) and then dried (MgSO$_4$) and evaporated at a bath temperature of 30° C. The resulting orange oil was purified by chromatography on silica gel (eluting with EtOAc:MeOH:petroleum ether 30:0.5:10) to afford ((S)-1-(2-((((4-((S)-2-(((allyloxy)carbonyl)amino)-6-((tert-butoxycarbonyl)amino)hexanamido)benzyl)oxy)carbonyl)amino)-4-((6-((S)-1-(chloromethyl)-5-((di-tert-butoxyphosphoryl)oxy)-1,2-dihydro-3H-benzo[e]indol-3-yl)-6-oxohexyl)oxy)-5-methoxybenzoyl)pyrrolidin-2-yl)methyl acetate 3g (385 mg, 84%) as a foamy solid, mp 72-75° C.; [α]$_D$ –55.2° (c 0.53, CHCl$_3$); $^1$H NMR [(CD$_3$)$_2$SO] δ 10.04 (s, exchangeable with D$_2$O, 1 H), 9.12 (br s, exchangeable with D$_2$O, 1 H), 8.56 (s, 1 H), 8.03 (d, J=8.3 Hz, 1 H), 7.92 (d, J=8.4 Hz, 1 H), 7.65-7.52 (m, 3H, reduced to 2H after D$_2$O), 7.46 (t, J=7.8 Hz, 2 H), 7.31 (d, J=8.5 Hz, 2 H), 7.20 (br s, 1 H), 6.86 (s, 1 H), 6.75 (poorly resolved t, exchangeable with D$_2$O, 1 H), 5.97-5.83 (m, 1 H), 5.30 (br d, J=17.3 Hz, 1 H), 5.17 (br d, J=10.6 Hz, 1 H), 5.18-4.97 (m, 2 H), 4.51-3.85 (m, 13 H), 3.74 (s, 3 H), 3.43-3.23 (m, 2H, partially obscured by water peak), 2.94-2.83 (m, 2 H), 2.65-2.50 (m, 2H, partially obscured by DMSO peak), 2.07-1.91 (m, 1 H), 2.01 (br s, 3 H), 1.88-1.43 (m, 11 H), 1.473-1.468 (2 s, 18 H), 1.43-1.20 (m, 4 H), 1.35 (s, 9 H). HRMS (ESI) m/z calc. for C$_{65}$H$_{89}$ClN$_6$O$_{17}$P: 1291.5665, found: 1291.5705 [MH$^+$]; calc. for C$_{65}$H$_{88}$ClKN$_6$O$_{17}$P: 1329.5262, found: 1329.5264 [MK$^+$]; calc. for C$_{65}$H$_{88}$ClN$_6$NaO$_{17}$P: 1313.5554, found: 1313.5524 [MNa$^+$].

Step C: Synthesis of LD-3
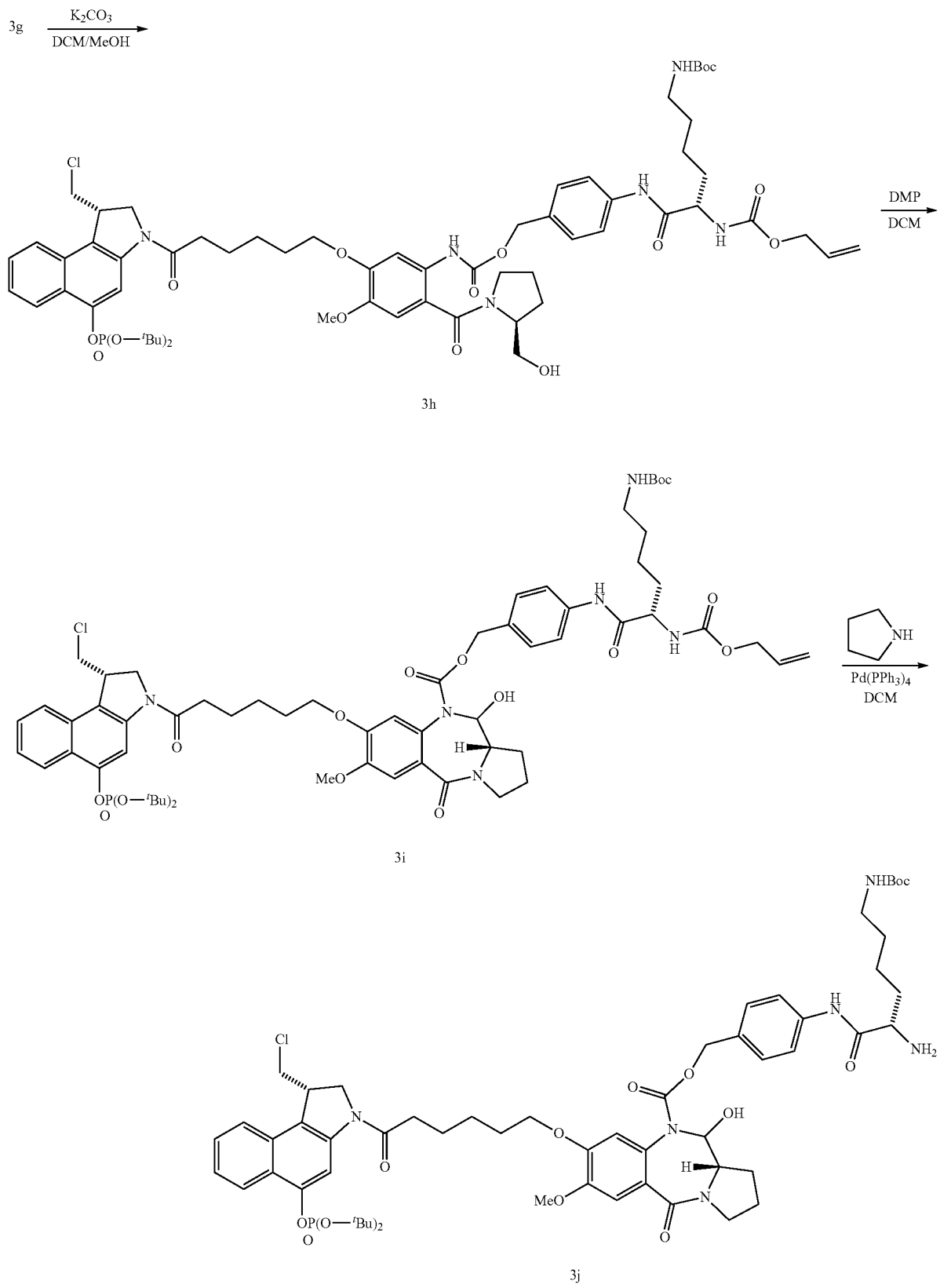

A mixture of 3g (366 mg, 0.28 mmol) and $K_2CO_3$ (1.14 g, 8.24 mmol) in DCM (9 mL) and MeOH (9 mL) was stirred at 0° C. for 3 h 30 min. The mixture was stirred with cold EtOAc (200 mL) and ice-water (150 mL) for 10 min. The EtOAc layer was separated, washed again with water (100 mL), and then dried ($MgSO_4$) and evaporated at a bath temperature of 25° C. to give allyl tert-butyl ((S)-6-((4-((((5-((6-((S)-1-(chloromethyl)-5-((di-tert-butoxyphosphoryl)oxy)-1,2-dihydro-3H-benzo[e]indol-3-yl)-6-oxohexyl)oxy)-2-((S)-2-(hydroxymethyl)pyrrolidine-1-carbonyl)-4-methoxyphenyl)carbamoyl)oxy)methyl)phenyl)amino)-6-oxohexane-1,5-diyl)dicarbamate 3h (343 mg, 97%) as a colorless foamy solid, mp 71-75° C.; $[\alpha]_D$−58.2° (c 0.57, $CHCl_3$); $^1H$ NMR [$(CD_3)_2SO$] δ 10.04 (s, exchangeable with $D_2O$, 1 H), 9.11 (br s, exchangeable with $D_2O$, 1 H), 8.56 (s, 1 H), 8.03 (d, J=8.3 Hz, 1 H), 7.92 (d, J=8.4 Hz, 1 H), 7.65-7.53 (m, 3H, reduced to 2H after $D_2O$), 7.46 (t, J=7.6 Hz, 2 H), 7.32 (d, J=8.6 Hz, 2 H), 7.27 (br s, 1 H), 6.93 (s, 1 H), 6.75 (poorly resolved t, exchangeable with $D_2O$, 1 H), 5.97-5.82 (m, 1 H), 5.29 (br d, J=17.2 Hz, 1 H), 5.17 (br d, J=10.5 Hz, 1 H), 5.03 (br s, 2 H), 4.73 (t, J=5.8 Hz, exchangeable with $D_2O$, 1 H), 4.50-3.82 (m, 11 H), 3.74 (s, 3 H), 3.62-3.44 (m, 2 H), 3.40-3.21 (m, 2 H, partially obscured by water peak), 2.95-2.80 (m, 2 H), 2.65-2.50 (m, 2 H, partially obscured by DMSO peak), 1.93-1.21 (m, 16 H), 1.473-1.468 (2 s, 18 H), 1.35 (s, 9 H). HRMS (ESI) m/z calc. for $C_{63}H_{86}ClKN_6O_{16}P$: 1287.5158, found: 1287.5113 [MK$^+$]; calc. for $C_{63}H_{86}ClN_6NaO_{16}P$: 1271.5419, found: 1271.5381 [MNa$^+$].

To a stirred solution of 3h (322 mg, 0.26 mmol) in dry DCM (14 mL) at 0° C. was added Dess-Martin periodinane (DMP) (131 mg, 0.31 mmol) portionwise over 3 min. The reaction mixture was stirred at 0° C. for a further 2 h, then at 20° C. for 50 h. The mixture was diluted with DCM (40 mL) and 10% $Na_2S_2O_3$ (40 mL), stirred at 20° C. for 10 min, and then partitioned between DCM (200 mL) and saturated $NaHCO_3$ solution (150 mL). The DCM layer was separated and the aqueous layer was further extracted with DCM (2×50 mL). The combined DCM extracts were washed with saturated $NaHCO_3$ solution (2×100 mL) and water (2×100 mL), and then dried ($MgSO_4$) and evaporated at a bath temperature of 25° C. The resulting orange oil was purified by chromatography on silica gel (eluting with $CHCl_3$:MeOH 40:1) to give 4-((S)-2-(((allyloxy)carbonyl)amino)-6-((tert-butoxycarbonyl)amino)hexanamido)benzyl (11aS)-8-((6-((S)-1-(chloromethyl)-5-((di-tert-butoxyphosphoryl)oxy)-1,2-dihydro-3H-benzo[e]indol-3-yl)-6-oxohexyl)oxy)-11-hydroxy-7-methoxy-5-oxo-2,3,11,11a-tetrahydro-1H-benzo[e]pyrrolo[1,2-a][1,4]diazepine-10(5H)-carboxylate 3i (228 mg, 71%) as a pale brown foamy solid, mp 98° C. (decomp); $[\alpha]_D$+74.5° (c 0.26, $CHCl_3$); $^1H$ NMR [$(CD_3)_2SO$] δ 10.02 (s, exchangeable with $D_2O$, 1 H), 8.56 (s, 1 H), 8.04 (d, J=8.3 Hz, 1 H), 7.92 (d, J=8.4 Hz, 1 H), 7.65-7.47 (m, 5 H, reduced to 4 H after $D_2O$), 7.25-7.12 (m, 2 H, br s and 1 H on $D_2O$ exchange), 7.03 (s, 1 H), 6.83-6.64 (m, 2 H), 6.48 (br s, exchangeable with $D_2O$, 1 H), 5.96-5.80 (m, 1 H), 5.52-5.39 (m, d on $D_2O$ exchange, J=9.6 Hz, 1 H), 5.27 (br d, J=16.8 Hz, 1 H), 5.21-5.10 (m, 2 H), 4.81 (br d, J=12.3 Hz, 1 H), 4.54-3.85 (m, 8 H), 3.83-3.70 (m, 5 H), 3.53-3.21 (m, 3 H, partially obscured by water peak), 2.93-2.82 (m, 2 H), 2.64-2.47 (m, 2 H, partially obscured by DMSO peak), 2.10-1.20 (m, 16 H), 1.470 and 1.464 (2 s, 18 H), 1.34 (s, 9 H). HRMS (ESI) m/z calc. for $C_{63}H_{84}ClKN_6O_{16}P$: 1285.5002, found: 1285.4938 [MK$^+$]; calc. for $C_{63}H_{84}ClN_6NaO_{16}P$: 1269.5262, found: 1269.5220 [MNa$^+$].

To a stirred solution of 3i (125 mg, 0.10 mmol) in DCM (2 mL) at 20° C. under a nitrogen atmosphere was added $Pd(Ph_3P)_4$ (2.9 mg; 9.8% Pd) and pyrrolidine (0.08 mL, 1.00 mmol). The mixture was stirred at 20° C. and monitored by TLC (EtOAc:MeOH 20:1). After 40 min more $Pd(Ph_3P)_4$ (5.8 mg; 9.8% Pd) and pyrrolidine (0.16 mL, 2.00 mmol) were added and the mixture was stirred for another 3 h. The mixture was partitioned between EtOAc (100 mL) and water (100 mL). The EtOAc layer was separated and washed again with water (50 mL), and then dried ($MgSO_4$) and evaporated at a bath temperature of 25° C. The crude 4-((S)-2-amino-6-((tert-butoxycarbonyl)amino)hexanamido)benzyl (11aS)-8-((6-((S)-1-(chloromethyl)-5-((di-tert-butoxyphosphoryl)oxy)-1,2-dihydro-3H-benzo[e]indol-3-yl)-6-oxohexyl)oxy)-11-hydroxy-7-methoxy-5-oxo-2,3,11,11a-tetrahydro-1H-benzo[e]pyrrolo[1,2-a][1,4]diazepine-10(5H)-carboxylate 3j (94 mg, 81%) was used for the next step without further purification. HRMS (ESI) m/z calc. for $C_{59}H_{81}ClN_6O_{14}P$: 1163.5231, found: 1163.5188 [MH$^+$].

A solution of 3j (91 mg, 0.078 mmol) in dry DMA (1.0 mL) was treated with a pre-formed (at 20° C. for 10 min) mixture of 1-((5-(2,5-dioxo-2,5-dihydro-1H-pyrrol-1-yl)pentyl)carbamoyl)cyclobutanecarboxylic acid 1p (36 mg, 0.12 mmol), EDCI.HCl (34 mg, 0.18 mmol), and TsOH (4.0 mg, 0.023 mmol) in dry DMA (0.5 mL) at 20° C. under a nitrogen atmosphere. After 10 min DIPEA (0.016 mL, 0.078 mmol) was added and the reaction mixture was stirred for 23 h. The mixture was partitioned between EtOAc (100 mL) and water (100 mL). The EtOAc layer was separated and washed further with saturated $NaHCO_3$ (50 mL), water (50 mL), and then dried ($MgSO_4$). Evaporation of solvent at a bath temperature of 25° C. gave a crude product which was purified by chromatography on silica gel (eluting with $CHCl_3$:EtOAc:MeOH 30:10:2) to give 4-((S)-6-((tert-butoxycarbonyl)amino)-2-(1-((5-(2,5-dioxo-2,5-dihydro-1H-pyrrol-1-yl)pentyl)carbamoyl)cyclobutane-1-carboxamido)hexanamido)benzyl (11aS)-8-((6-((S)-1-(chloromethyl)-5-(phosphonooxy)-1,2-dihydro-3H-benzo[e]indol-3-yl)-6-oxohexyl)oxy)-11-hydroxy-7-methoxy-5-oxo-2,3,11,11a-tetrahydro-1H-benzo[e]pyrrolo[1,2-a][1,4]diazepine-10(5H)-carboxylate 3k (63 mg, 56%) as a pale brown foamy solid; mp 67-70° C.; $[\alpha]_D$+23.9° (c 2.09, $CHCl_3$); $^1H$ NMR [$(CD_3)_2SO$] δ 10.05 (s, exchangeable with $D_2O$, 1 H), 8.56 (s, 1 H), 8.03 (d, J=8.3 Hz, 1 H), 7.92 (d, J=8.4 Hz, 1 H), 7.84-7.71 (m, 2 H, exchangeable with $D_2O$), 7.62-7.52 (m, 3 H), 7.46 (t, J=7.7 Hz, 1 H), 7.22-7.13 (m, 2 H), 7.03 (br s, 1 H), 6.96 (s, 2 H), 6.71 (br s, 2 H, reduced to 1 H after $D_2O$), 6.49 (br s, exchangeable with $D_2O$, 1 H), 5.51-5.41 (m, but d on $D_2O$ exchange with J=9.5 Hz, 1 H), 5.15 (d, J=12.2 Hz, 1 H), 4.82 (br d, J=12.4 Hz, 1 H), 4.47-3.85 (m, 8 H), 3.77 (br s, 3 H), 3.52-3.20 (m, 3 H, partially obscured by water peak), 3.12-3.20 (m, but t on $D_2O$ exchange with J=6.7 Hz, 2 H), 2.92-2.80 (m, 2 H), 2.65-2.50 (m, 2 H, partially obscured by DMSO peak), 2.39 (t, J=7.9 Hz, 2 H), 2.07-1.24 (m, 28 H), 1.469 and 1.463 (2 s, 18 H), 1.33 (s, 9 H). HRMS (ESI) m/z calc. for $C_{74}H_{98}ClN_8NaO_{18}P$: 1475.6317, found: 1475.6267 [MNa$^+$].

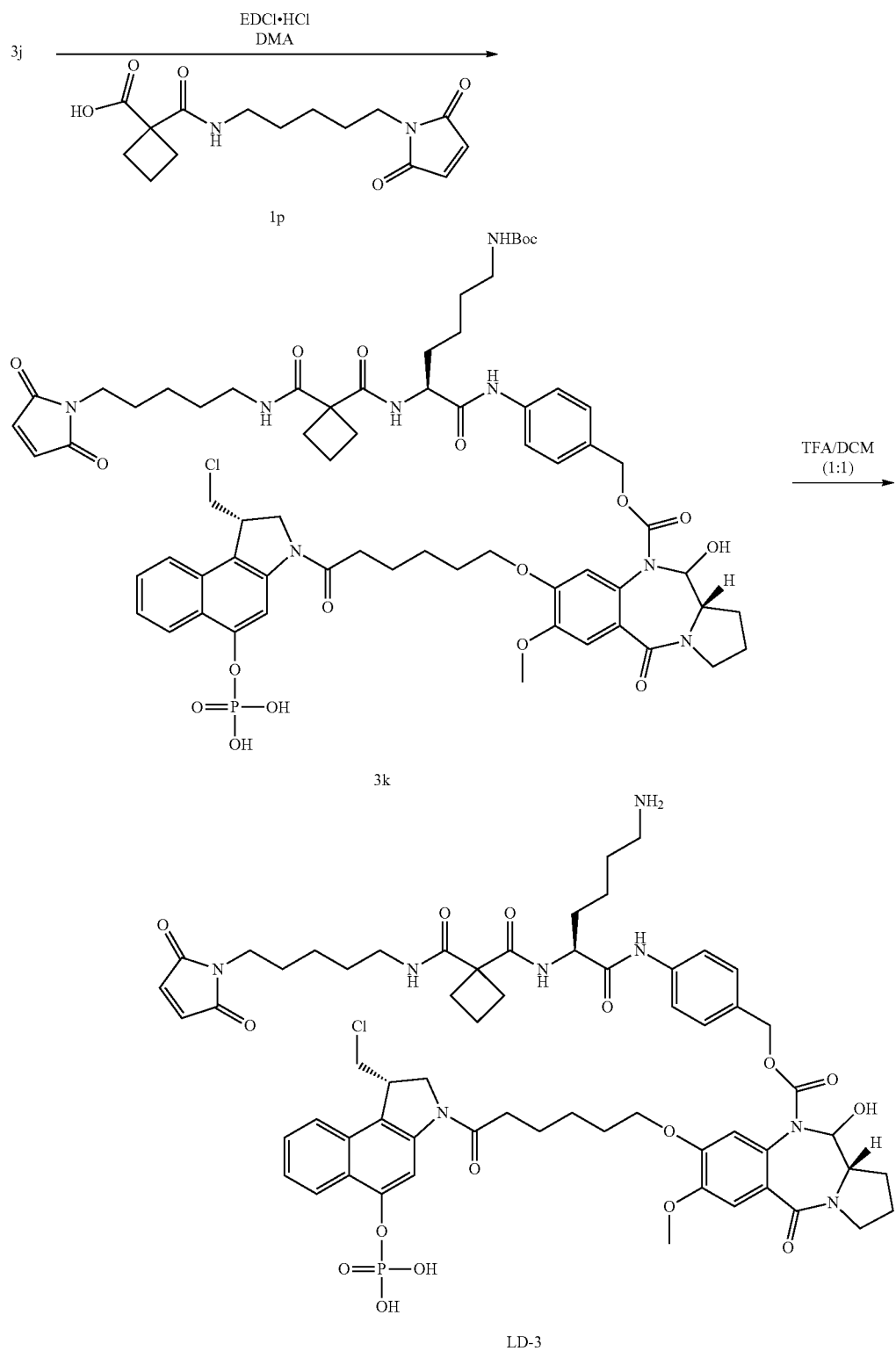

To a stirred solution of 3k (45 mg, 0.031 mmol) in DCM (1.0 mL) at 20° C. under nitrogen was added TFA (1.0 mL) and the mixture was stirred for 15 min. Petroleum ether (20 mL) was added and the mixture was stirred for 30 min. The supernatant was decanted and the procedure was repeated using EtOAc:petroleum ether (1:5) (2×20 mL). The resulting solid was collected and purified by preparative HPLC [Synergi PolarRP column; aqueous TFA (pH=2.56; 90% to 2%)/10% water in CH$_3$CN (10% to 98%); gradient elution over 23 min with a flow rate of 12 mL/min] to give pure LD-3 (17.5 mg, 38%) as a beige solid, purity (HPLC): 99.1%; [α]$_D$+54.9° (c 0.18, MeOH); $^1$H NMR [(CD$_3$)$_2$SO]

δ 10.20 (s, exchangeable with D₂O, 1 H), 8.50 (s, 1 H), 8.20-7.78 (m, 7 H, reduced to 1H after D₂O), 8.12 (d, J=9.1 Hz, 1 H), 7.72-7.47 (m, 4 H, reduced to 3H after D₂O), 7.40 (t, J=7.5 Hz, 1 H), 7.17 (br d, J=7.3 Hz, 2 H), 7.03 (br s, 1 H), 6.97 (s, 2 H), 6.66 (br s, exchangeable with D₂O, 1 H), 5.51 (br s, 1 H), 5.48 (br d, J=9.7 Hz, 1 H), 5.32-5.18 (m, but d after D₂O, J=12.6 Hz, 1 H), 4.75 (br d, J=12.4 Hz, 1 H), 4.44-3.81 (m, 8 H), 3.77 (s, 3 H), 3.52-3.21 (m, 5 H, partially obscured by water peak), 3.04 (q, but t after D₂O with J=6.8 Hz, 2 H), 2.80-2.68 (m, 2 H), 2.39 (t, J=7.7 Hz, 2 H), 2.12-1.08 (m, 28 H). HRMS (ESI) m/z calc. for $C_{61}H_{75}ClN_8O_{16}P$: 1241.4722, found: 1241.4700 [MH⁺]; calc. for $C_{61}H_{74}ClN_8NaO_{16}P$: 1263.4541, found: 1263.4531 [MNa⁺].

B. Synthesis of CBI Dimer Linker Drug Intermediates

1. LD-1

The CBI-CBI peptidomimetic linker dimer (4-((S)-2-(1-((5-(2,5-dioxo-2,5-dihydro-1H-pyrrol-1-yl)pentyl)carbamoyl)cyclobutanecarboxamido)-5-ureidopentanamido)benzyl (2,5-bis((E)-3-((S)-1-(chloromethyl)-5-(phosphonooxy)-1H-benzo[e]indol-3(2H)-yl)-3-oxoprop-1-en-1-yl)phenyl) carbamate, LD-1) having the formula:

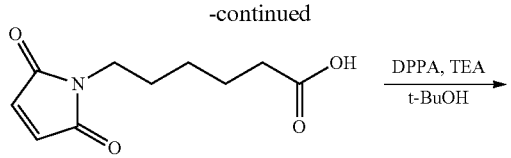

1c

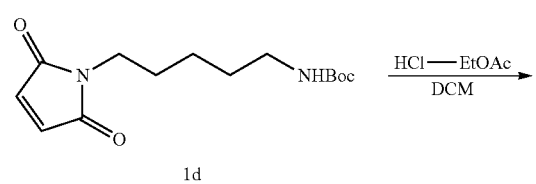

1d

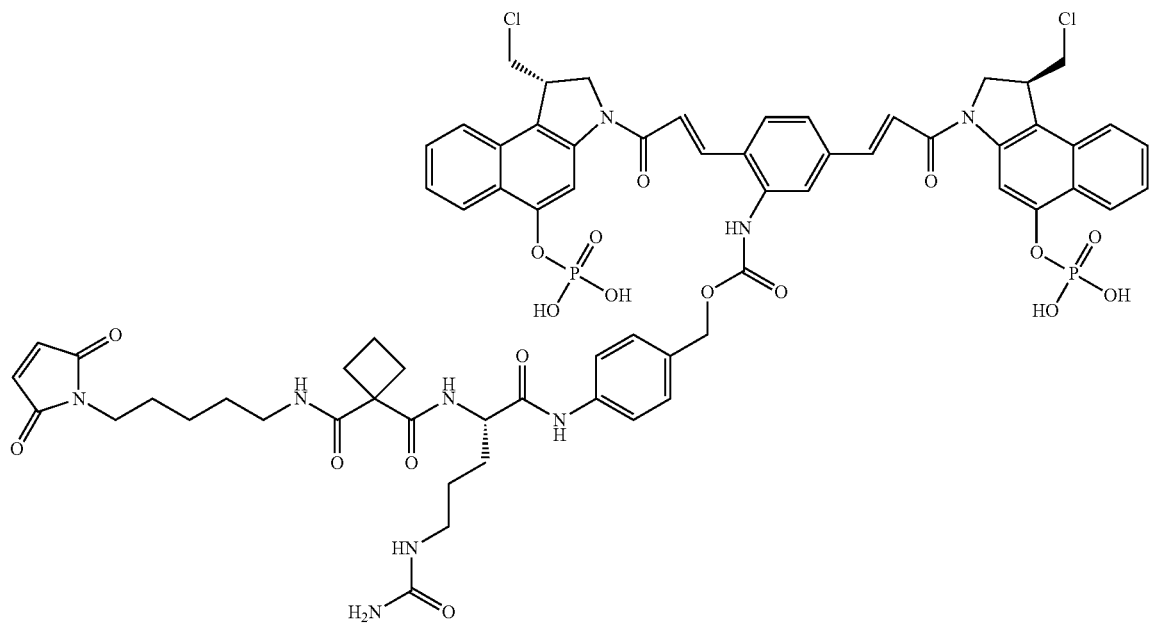

LD-1 was synthesized in three steps (steps A, B, and C) as follows.

Step A: Synthesis of (S)-N-(5-(2,5-dioxo-2,5-dihydro-1H-pyrrol-1-yl)pentyl)-N-(1-(4-(hydroxymethyl)phenylamino)-1-oxo-5-ureidopentan-2-yl)cyclobutane-1,1-dicarboxamide 1m

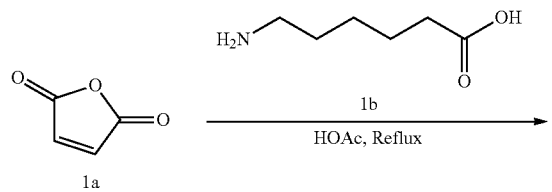

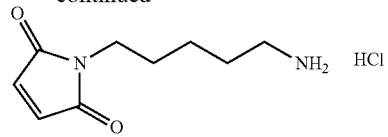

1e

Maleic anhydride (furan-2,5-dione) 1a (150 g, 1.53 mol) was added to a stirred solution of 6-aminohexanoic acid 1b (201 g, 1.53 mol) in HOAc (1000 mL). After the mixture was stirred at r.t. (room temperature) for 2 h, it was heated at reflux for 8 h. The organic solvents were removed under reduced pressure and the residue was extracted with EtOAc (500 mL×3), washed with H₂O. The combined organic layers was dried over Na$_2$SO$_4$ and concentrated to give the crude product. It was washed with petroleum ether to give 6-(2,5-dioxo-2,5-dihydro-1H-pyrrol-1-yl)hexanoic acid 1c as white solid (250 g, 77.4%).

DPPA (130 g, 473 mmol) and TEA (47.9 g, 473 mmol) was added to a solution of 1c (100 g, 473 mmol) in t-BuOH (200 mL). The mixture was heated at reflux for 8 h under N$_2$. The mixture was concentrated, and the residue was purified by column chromatography on silica gel (PE:EtOAc=3:1) to give tert-butyl (5-(2,5-dioxo-2,5-dihydro-1H-pyrrol-1-yl)pentyl)carbamate 1d (13 g, 10%).

To a solution of 1d (28 g, 992 mmol) in anhydrous EtOAc (30 mL) was added HCl/EtOAc (50 mL) dropwise. After the mixture was stirred at r.t. for 5 h, it was filtered and the solid was dried to give 1-(5-aminopentyl)-1H-pyrrole-2,5-dione hydrochloride 1e (16 g, 73.7%). $^1$H NMR (400 MHz, DMSO-d$_6$): δ 8.02 (s, 2H), 6.99 (s, 2H), 3.37-3.34 (m, 2H), 2.71-2.64 (m, 2H), 1.56-1.43 (m, 4H), 1.23-1.20 (m, 2H).

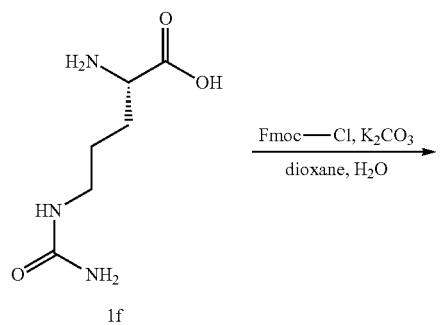

1f

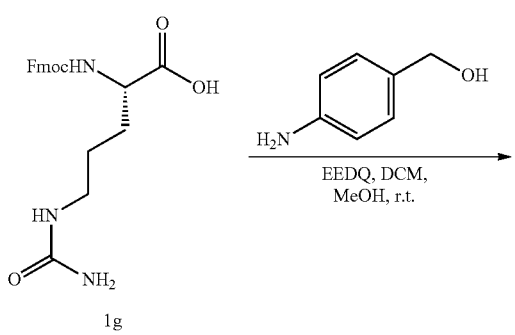

1g

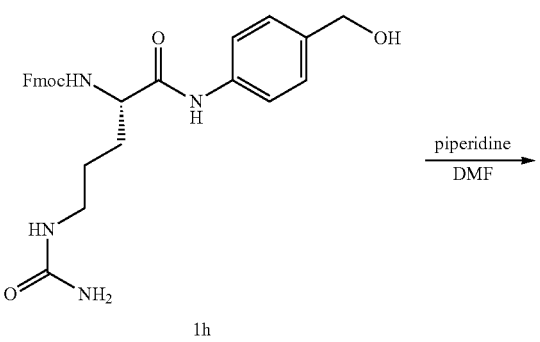

1h

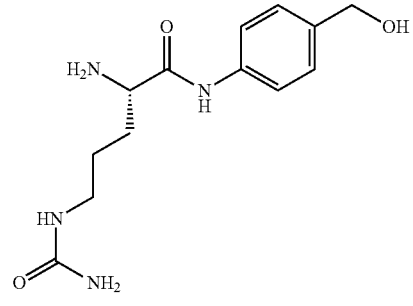

1i

To a mixture of (S)-2-amino-5-ureidopentanoic acid 1f (17.50 g, 0.10 mol) in a mixture of dioxane and H$_2$O (50 mL/75 mL) was added K$_2$CO$_3$ (34.55 g, 0.25 mol). Fmoc-Cl (30.96 g, 0.12 mol) was added slowly at 0° C. The reaction mixture was warmed to r.t. over 2 h. Organic solvent was removed under reduced pressure, and the water slurry was adjusted to pH=3 with 6 M HCl solution, and extracted with EtOAc (100 mL×3). The organic layer was dried over Na$_2$SO$_4$, filtered, and concentrated under reduced pressure to give (S)-2-((((9H-fluoren-9-yl)methoxy)carbonyl)amino)-5-ureidopentanoic acid 1g (38.0 g, 95.6%).

To a solution of 1g (4 g, 10 mmol) in a mixture of DCM and MeOH (100 mL/50 mL) were added 4-amino-phenyl-methanol (1.6 g, 13 mmol, 1.3 eq) and EEDQ (3.2 g, 13 mmol, 1.3 eq). After the mixture was stirred at r.t. for 16 h under N$_2$, it was concentrated to give a brown solid. MTBE (200 mL) was added and it was stirred at 15° C. for 2 h. The solid was collected by filtration, washed with MTBE (50 mL×2) to give (S)-(9H-fluoren-9-yl)methyl (1-((4-(hydroxymethyl)phenyl)amino)-1-oxo-5-ureidopentan-2-yl)carbamate 1h as an orange solid (4.2 g, 84%). LCMS (ESI): m/z 503.0 [M+1].

To a stirred solution of 1h (4.2 g, 8.3 mmol) in dry DMF (20 ml) was added piperidine (1.65 mL, 17 mmol, 2 eq) dropwise at r.t. The mixture was stirred at r.t. for 30 min, and solid precipitate formed. Dry DCM (50 mL) was added, and the mixture became transparent immediately. The mixture was stirred at r.t. for another 30 min, and LCMS showed 1h was consumed. It was concentrated to dryness under reduced pressure (make sure no piperidine remained), and the residue was partitioned between EtOAc and H$_2$O (50 mL/20 mL). Aqueous phase was washed with EtOAc (50 mL×2) and concentrated to give (S)-2-amino-N-(4-(hydroxymethyl)phenyl)-5-ureidopentanamide 1i as an oily residual (2.2 g, 94%) (contained small amount of DMF).

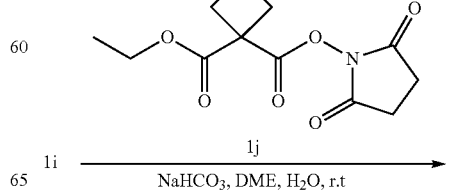

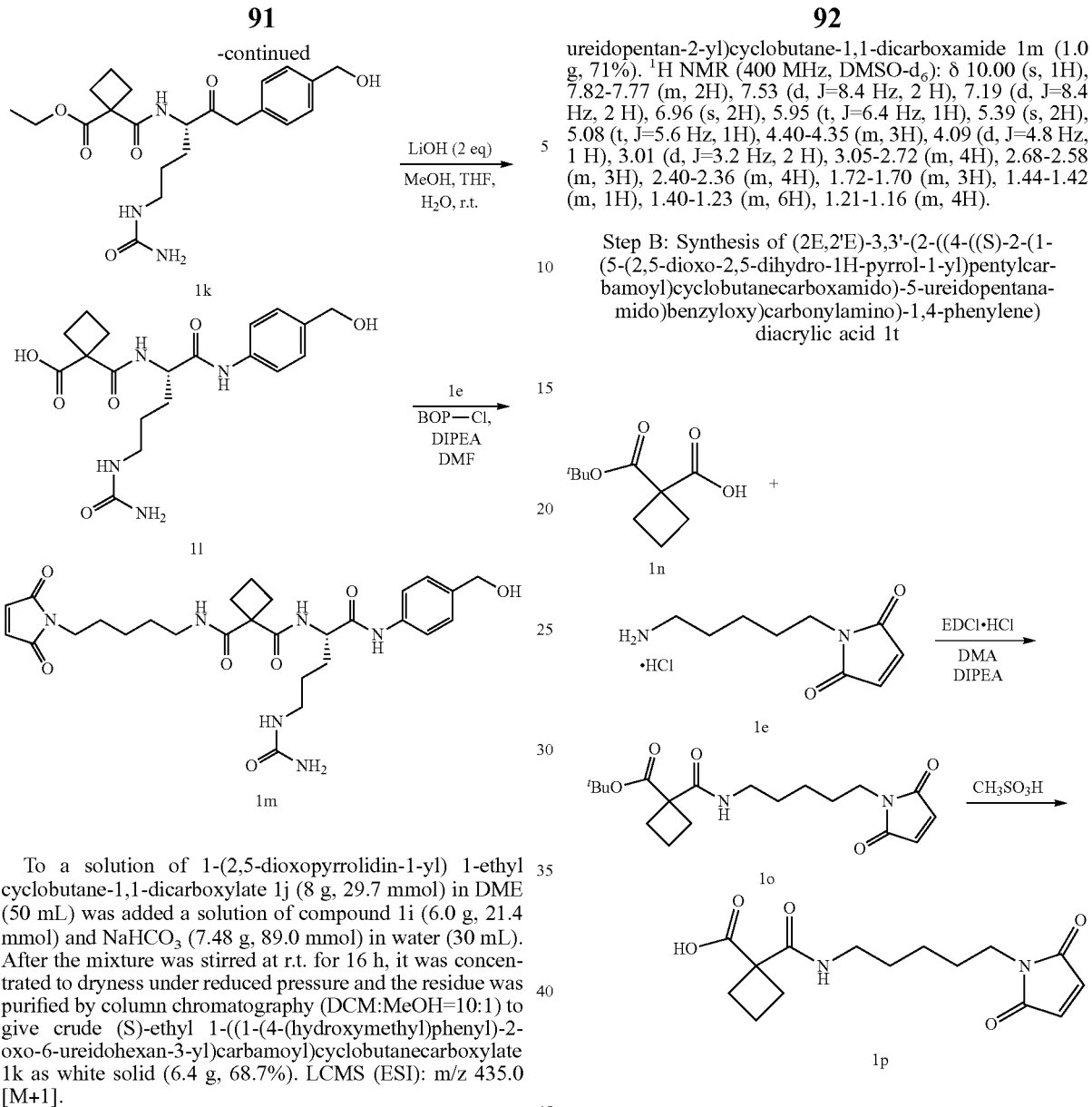

To a solution of 1-(2,5-dioxopyrrolidin-1-yl) 1-ethyl cyclobutane-1,1-dicarboxylate 1j (8 g, 29.7 mmol) in DME (50 mL) was added a solution of compound 1i (6.0 g, 21.4 mmol) and NaHCO$_3$ (7.48 g, 89.0 mmol) in water (30 mL). After the mixture was stirred at r.t. for 16 h, it was concentrated to dryness under reduced pressure and the residue was purified by column chromatography (DCM:MeOH=10:1) to give crude (S)-ethyl 1-((1-(4-(hydroxymethyl)phenyl)-2-oxo-6-ureidohexan-3-yl)carbamoyl)cyclobutanecarboxylate 1k as white solid (6.4 g, 68.7%). LCMS (ESI): m/z 435.0 [M+1].

To a stirred solution of 1k (6.4 g, 14.7 mmol) in a mixture of THF and MeOH (20 mL/10 mL) was added a solution of LiOH/H$_2$O (1.2 g, 28.6 mmol) in H$_2$O (20 mL) at r.t. After the reaction mixture was stirred at r.t. for 16 h, solvent was removed under reduced pressure, the residue obtained was purified by prep-HPLC to give (S)-1-((1-((4-(hydroxymethyl)phenyl)amino)-1-oxo-5-ureidopentan-2-yl)carbamoyl)cyclobutanecarboxylic acid 1l (3.5 g, yield: 58.5%). LCMS (ESI): m/z 406.9 [M+1]. $^1$H NMR (400 MHz, Methanol-d$_4$) δ 8.86 (d, J=8.4 Hz, 2 H), 8.51 (d, J=8.4 Hz, 2 H), 5.88-5.85 (m, 1 H), 5.78 (s, 2 H), 4.54-4.49 (m, 3 H), 4.38-4.32 (m, 1 H), 3.86-3.75 (m, 1 H), 3.84-3.80 (m, 2 H), 3.28-3.21 (m, 1 H), 3.30-3.24 (m, 1 H), 3.00-2.80 (m, 1 H), 2.37-2.28 (m, 2 H).

DIPEA (1.59 g, 12.3 mmol) and BOP-Cl (692 mg, 2.71 mmol) was added to a solution of 1l (1.0 g, 2.46 mmol) in DMF (10 mL) at 0° C., followed by 1e (592 mg, 2.71 mmol). The mixture was stirred at 0° C. for 0.5 h. The reaction mixture was quenched with a citric acid solution (10 mL), extracted with DCM/MeOH (10:1). The organic layer was dried and concentrated, and the residue was purified by column chromatography on silica gel (DCM:MeOH=10:1) to give (S)-N-(5-(2,5-dioxo-2,5-dihydro-1H-pyrrol-1-yl)pentyl)-N-(1-((4-(hydroxymethyl)phenyl)amino)-1-oxo-5-ureidopentan-2-yl)cyclobutane-1,1-dicarboxamide 1m (1.0 g, 71%). $^1$H NMR (400 MHz, DMSO-d$_6$): δ 10.00 (s, 1H), 7.82-7.77 (m, 2H), 7.53 (d, J=8.4 Hz, 2 H), 7.19 (d, J=8.4 Hz, 2 H), 6.96 (s, 2H), 5.95 (t, J=6.4 Hz, 1H), 5.39 (s, 2H), 5.08 (t, J=5.6 Hz, 1H), 4.40-4.35 (m, 3H), 4.09 (d, J=4.8 Hz, 1 H), 3.01 (d, J=3.2 Hz, 2 H), 3.05-2.72 (m, 4H), 2.68-2.58 (m, 3H), 2.40-2.36 (m, 4H), 1.72-1.70 (m, 3H), 1.44-1.42 (m, 1H), 1.40-1.23 (m, 6H), 1.21-1.16 (m, 4H).

Step B: Synthesis of (2E,2'E)-3,3'-(2-((4-((S)-2-(1-(5-(2,5-dioxo-2,5-dihydro-1H-pyrrol-1-yl)pentylcarbamoyl)cyclobutanecarboxamido)-5-ureidopentanamido)benzyloxy)carbonylamino)-1,4-phenylene)diacrylic acid 1t To a mixture of 1-(tert-butoxycarbonyl)cyclobutanecarboxylic acid 1n (200 mg, 1.00 mmol) (WO 2002/076968), 1-(5-aminopentyl)-1H-pyrrole-2,5-dione hydrochloride 1e (218 mg, 1.00 mmol) (J. Med. Chem. 2013, 56, 7890-7901), EDCl·HCl (N-(3-dimethylaminopropyl)-N'-ethylcarbodiimide hydrochloride, CAS Reg. No. 25952-53-8) (576 mg, 3.00 mmol) and TsOH (35 mg, 0.20 mmol) was added DMA (2 mL). The mixture was stirred at 20° C. for 15 min and DIPEA (0.17 mL, 1.00 mmol) was added. The reaction mixture was stirred further for 20 h and partitioned between EtOAc (200 mL) and water (100 mL). The EtOAc layer was separated and washed successively with cold 1N HCl (100 mL), saturated NaHCO$_3$ (100 mL), and water (100 mL), and then dried (MgSO$_4$). Evaporation of solvent gave tert-butyl 1-((5-(2,5-dioxo-2,5-dihydro-1H-pyrrol-1-yl)pentyl)carbamoyl)cyclobutanecarboxylate 1o (290 mg, 80%) as a pale yellow solid, mp 63-65° C. $^1$H NMR [(CD$_3$)$_2$SO] δ 7.58 (t, J=5.6 Hz, 1 H), 7.00 (s, 2H), 3.37 (t, J=7.0 Hz, 2 H), 3.03 (q, J=6.0 Hz, 2 H), 2.40-2.23 (m, 4 H), 1.85-1.64 (m, 2 H), 1.55-1.32 (m, 4 H), 1.38 (s, 9 H), 1.26-1.01 (m, 2 H). HRMS (ESI) m/z calc. for C$_{19}$H$_{29}$N$_2$O$_5$: 365.2071, found: 365.2071 [MH$^+$]; calc. for C$_{19}$H$_{28}$N$_2$NaO$_5$: 387.1890, found: 387.1898 [MNa$^+$]; calc. for C$_{19}$H$_{28}$KN$_2$O$_5$: 403.1630, found: 403.1629 [MK$^+$].

To a stirred solution of 1o (794 mg, 2.18 mmol) in DCM (50 mL) was added methanesulfonic acid (2.83 mL, 43.6 mmol). The cloudy mixture was stirred at 20° C. for 2 h 30 min. The mixture was diluted with DCM (200 mL) and washed with water (2×50 mL). The DCM solution was dried (MgSO$_4$) and evaporated at 25° C. (bath temperature) to give 1-((5-(2,5-dioxo-2,5-dihydro-1H-pyrrol-1-yl)pentyl)carbamoyl)cyclobutanecarboxylic acid 1p (636 mg, 95%) as a pale yellow solid, mp 100-102° C.; $^1$H NMR [(CD$_3$)$_2$SO] δ br s, 1 H), □7.63 (t, J=5.4 Hz, 1 H), 7.00 (s, 2 H), 3.37 (t, J=7.0 Hz, 2 H), 3.02 (q, J=5.9 Hz, 2 H), 2.42-2.28 (m, 4 H), 1.89-1.63 (m, 2 H), 1.55-1.32 (m, 4 H), 1.29-1.11 (m, 2 H). Anal. (C$_{15}$H$_{20}$N$_2$O$_5$) Calc: C, 58.43; H, 6.54; N, 9.09. Found: C, 58.54; H, 6.39; 8.84.

To a solution of 1,4-dibromo-2-nitrobenzene (1.5 g, 21.4 mmol) in dioxane (4.0 mL) was added tert-butyl acrylate (2.74 g, 85.6 mmol), DIPEA (3.45 g, 107 mmol) and Pd(t-Bu$_3$P)$_2$ (0.55 g, 4.30 mmol). The reaction was stirred at 120° C. for 2.0 h under microwave irradiation. The reaction was repeated 4 times (total 6.0 g of 1,4-dibromo-2-nitrobenzene was used). The combined reaction mixture was concentrated, diluted with water (20 mL) and extracted with EtOAc (100.0 mL×3). The organic layer was combined, dried over Na$_2$SO$_4$. It was concentrated and purified by column (PE: EtOAc=10:1) to give (2E,2'E)-di-tert-butyl 3,3'-(2-nitro-1,4-phenylene)diacrylate 1q (3.8 g, 47%).

To a solution of 1q (3.8 g, 10.1 mmol) in EtOH/H$_2$O (120.0 mL) was added Fe (2.83 g, 50.7 mmol), and NH$_4$Cl (5.4 g, 101 mmol), and the reaction mixture was stirred at 100° C. for 2.0 h. The reaction mixture was filtered and the filtrate was concentrated and extracted with EtOAc (60.0 mL×3). The organic layer was combined, dried over Na$_2$SO$_4$ and concentrated to give (2E,2'E)-di-tert-butyl 3,3'-(2-amino-1,4-phenylene)diacrylate 1r (2.5 g, 72%).

To a solution of triphosgene (224 mg, 0.76 mmol) was added a solution of 1r (725 mg, 2.1 mmol) and Et$_3$N (530.3 mg, 5.25 mmol) in DCM (5.0 mL) dropwise in ice-bath. The reaction mixture was stirred at 21° C. for 1.0 h until there was no starting material left. The reaction mixture was washed with water (5.0 mL×2), and dried over Na$_2$SO$_4$. It was concentrated and dissolved in DCM (5.0 mL). A solution of 1m (1.0 g, 1.75 mmol) was added and the reaction mixture was stirred at 21° C. for 3.0 h. The reaction was quenched with MeOH (2.0 mL), and purified by column (DCM: MeOH=10:1) to give 1s (380 mg, 23%).

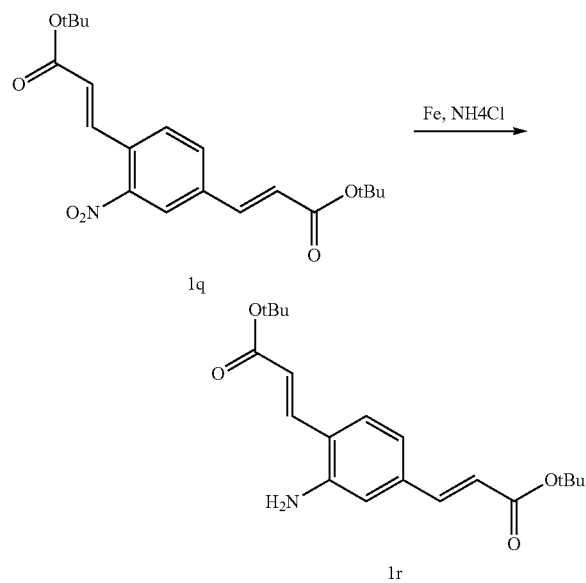

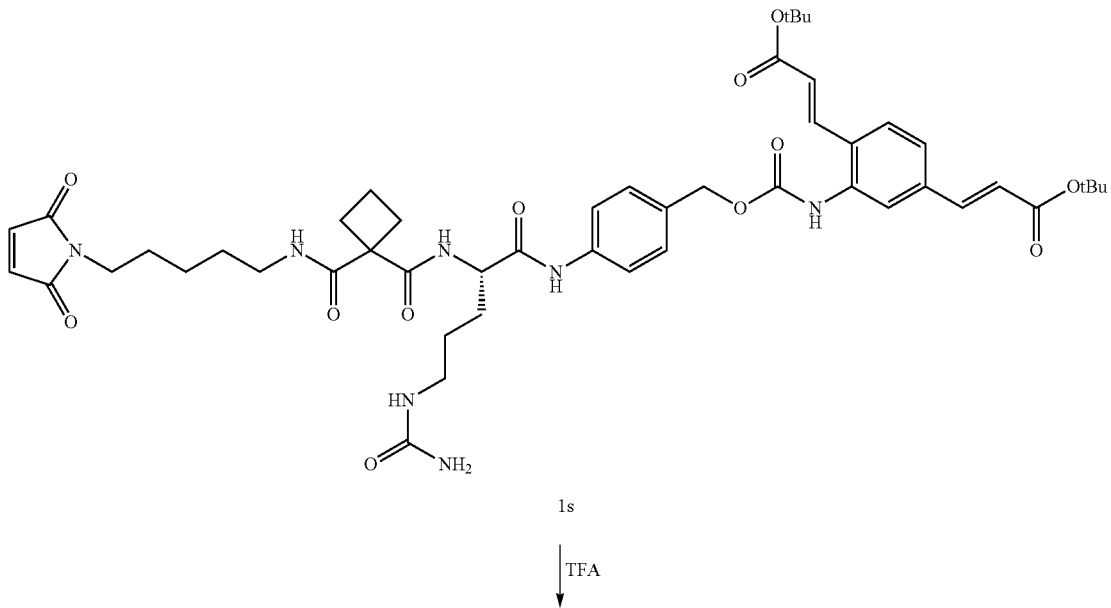

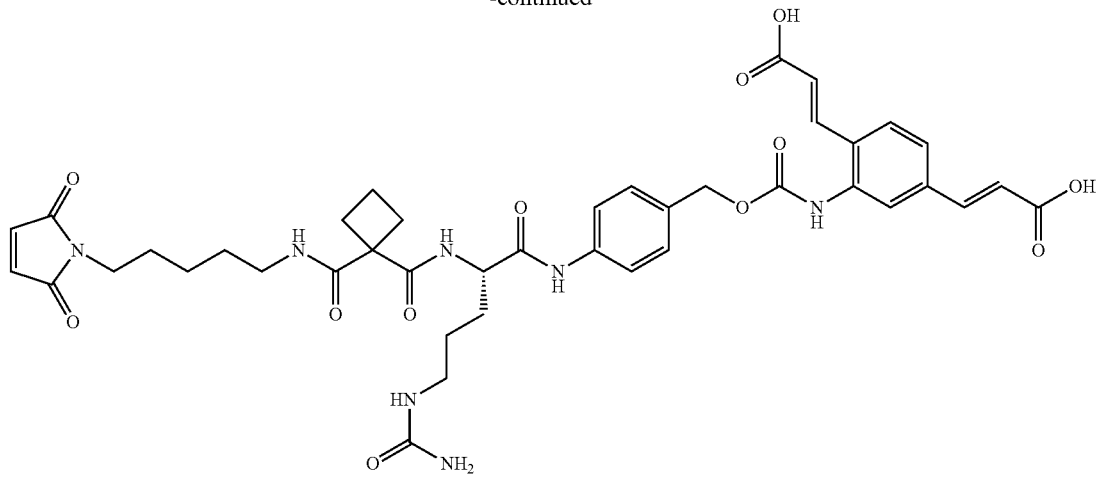

1t

To a solution of 1s (300.0 mg, 0.32 mmol) in DCM (10.0 mL) was added TFA (2.0 mL), and the mixture was stirred at 21° C. for 30 min. The mixture was adjusted to pH 6 with $NH_3 \cdot H_2O$. The precipitation was collected by filtration to give the product (2E,2'E)-3,3'-(2-((4-((S)-2-(1-(5-(2,5-dioxo-2,5-dihydro-1H-pyrrol-1-yl)pentylcarbamoyl)cyclobutanecarboxamido)-5-ureidopentanamido)benzyloxy)carbonylamino)-1,4-phenylene)diacrylic acid it (112.0 mg, yield 42%). LCMS (10-80, AB, 2.0 min) RT=0.962 min, [M+1]$^+$ =830.0; $^1$H NMR (400 MHz, DMSO-d$_6$) δ 12.45 (br, 2H), 10.10 (s, 1H), 9.55 (s, 1H), 7.50-7.81 (m, 8H), 7.34 (m, 2H), 6.95 (s, 2H), 6.47-6.57 (m, 2H), 5.96 (s, 1H), 5.40 (s, 2H), 5.05 (s, 2H), 4.36-4.39 (m, 1H), 2.98-3.06 (m, 6H), 2.35-2.39 (m, 4H), 1.15-1.73 (m, 13H).

Step C: Synthesis of LD-1

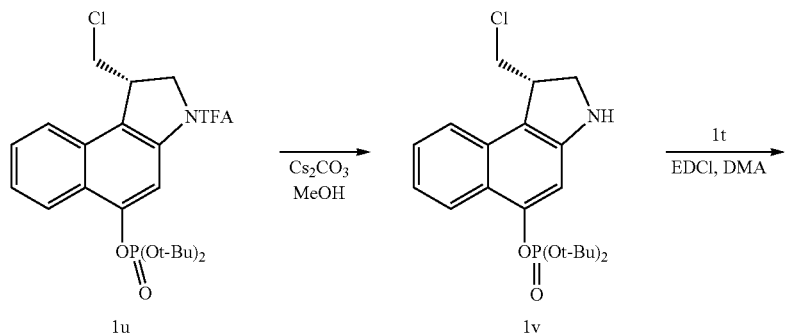

97
98
-continued
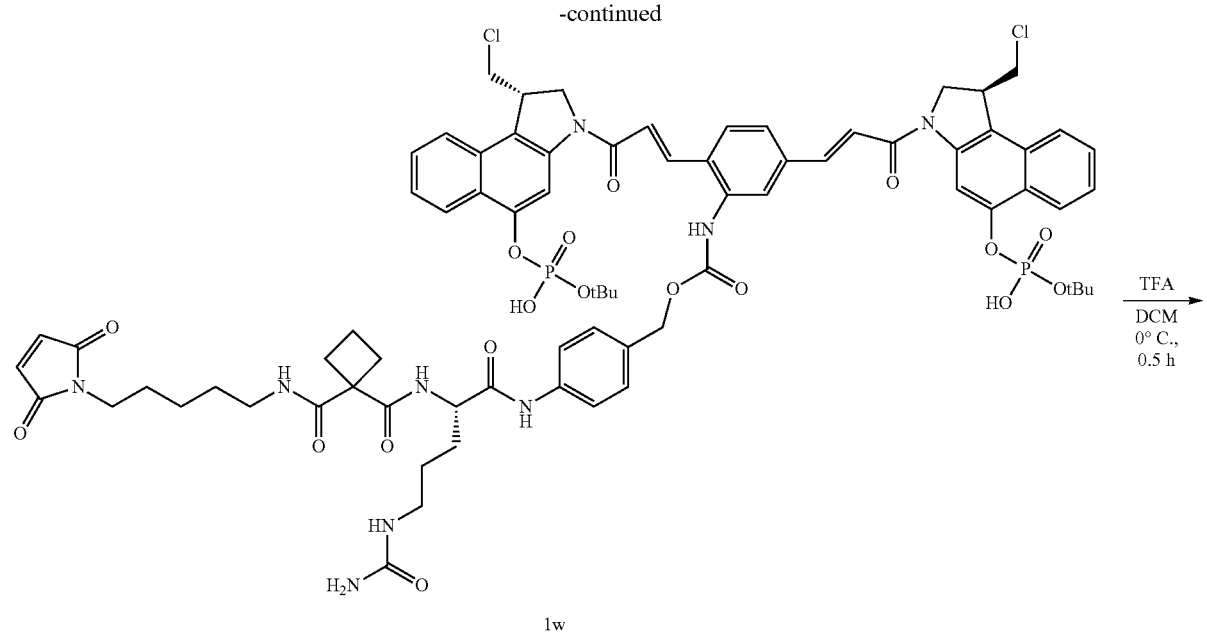
TFA
DCM
0° C.,
0.5 h
1w
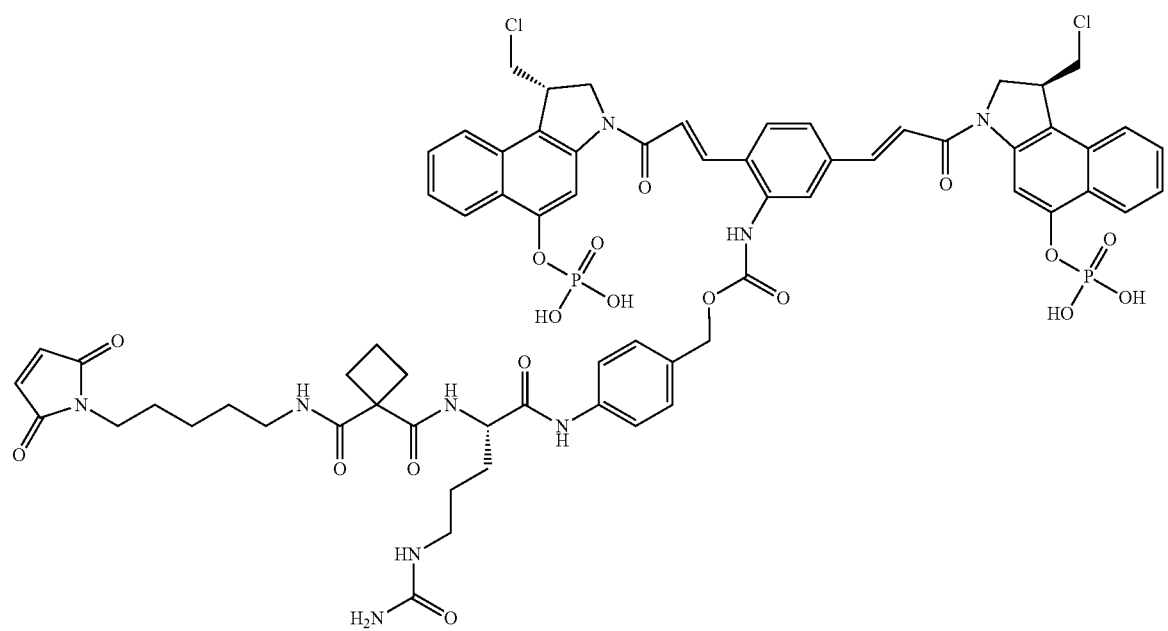
LD-1

To a solution of (S)-di-tert-butyl (1-(chloromethyl)-3-(2,2,2-trifluoroacetyl)-2,3-dihydro-1H-benzo[e]indol-5-yl) phosphate 1u (230 mg, 0.44 mmol) in MeOH (2 mL) cooled in an ice bath was added Cs$_2$CO$_3$ (287 mg, 0.88 mmol) and several drops of water. The mixture was stirred in the ice bath for 1 h and then redistributed between ethyl acetate and water. The aqueous phase was extracted with ethyl acetate three times. The combined organic extracts were washed with water and brine, dried over anhydrous Na$_2$SO$_4$, filtered through celite, and the solvent was removed. The resultant residue was dissolved in ethyl acetate and filtered through a pad of Florisil to give crude (S)-di-tert-butyl (1-(chloromethyl)-2,3-dihydro-1H-benzo[e]indol-5-yl) phosphate 1v as an off-white gum (188 mg, 100%) which was used directly without further purification.

To 184 mg (0.43 mmol) of 1v was added 1t (80 mg, 0.11 mmol), EDCI.HCl (165 mg, 0.86 mmol), toluenesulfonic acid (2.0 mg, 0.011 mmol) and DMA (0.5 mL). After the mixture was stirred overnight, most of the DMA was removed under vacuum and the residue was redistributed between ethyl acetate and aq. NaHCO$_3$. The aqueous phase was extracted with ethyl acetate three times. The combined organic extracts were washed with water followed by brine, dried over anhydrous Na$_2$SO$_4$, and filtered through a pad of Celite. The solvent was removed and the resultant residue was dissolved in the minimum DCM and precipitated by adding heptane to give crude product (195 mg), which was further purified by preparative HPLC [Column: Synergi-Max RP 4 µ, 250×21.20 mm; Mobile phase: A/B=from 90% to 2% (A: ammonium formate pH 3.45, B: 90% acetonitrile in water); flow rate 12 mL/min] to give 4-((S)-2-(1-((5-(2,5-dioxo-2,5-dihydro-1H-pyrrol-1-yl)pentyl)carbamoyl)cyclobutanecarboxamido)-5-ureidopentanamido)benzyl (2,5-bis((E)-3-((1 S)-5-((tert-butoxy(hydroxy)phosphoryl)oxy)-1-(chloromethyl)-1H-benzo[e]indol-3(2H)-yl)-3-oxoprop-1-en-1-yl)phenyl)carbamate 1w (56 mg, 34%) as a yellow solid. $^1$H NMR (DMSO) δ 10.02 (s, 1H), 8.67 (s, 2H), 8.14-8.06 (m, 4H), 7.97 (d, J=8.4 Hz, 2H), 7.86-7.76 (m, 4H), 7.70 (d, J=15.2 Hz, 1H), 7.63-7.59 (m, 2H), 7.53-7.49 (m, 2H), 7.29-7.23 (m, 2H), 6.96 (s, 2H, maleimide), 5.91 (br s, 1H), 5.36 (br s, 2H), 4.65-4.50 (m, 4H), 4.44-4.37 (m, 2H), 4.28-4.22 (m, 2H), 4.05-3.95 (m, 4H), 3.60 (t, J=6.6 Hz, 1H), 3.07-3.00 (m, 2H), 2.95-2.88 (m, 2H), 2.68-2.58 (m, 2H), 2.42-2.32 (m, 3H), 1.78-1.62 (m, 4H), 1.51, 1.50, 1.49, 1.48 (4s, 36H), 1.49-1.28 (m, 11H). $^{31}$P NMR (CDCl$_3$) δ −15.44 (s), 15.46 (s). HRMS (ESI) found m/z 1588.5827 (M+Na). C$_{78}$H$_{99}$Cl$_2$N$_9$NaO$_{17}$P$_2$ requires 1588.5903.

To a solution of 1w (25 mg, 0.015 mmol) in DCM (0.6 mL) cooled in an ice bath was added TFA (0.2 mL, 2.61 mmol). The mixture was stirred in an ice bath for 0.5 h. Ether was added and the resultant precipitate was collected by filtration and washed with ethyl acetate, THF and petroleum ether to give LD-51 as a brown solid (18 mg, 86%). $^1$H NMR (DMSO) δ 10.01 (br s, 1H), 8.60 (br s, 2H), 8.16-8.09 (m, 4H), 7.96-7.93 (m, 2H), 7.88-7.58 (m, 8H), 7.46 (t, J=7.7 Hz, 2H), 7.30-7.25 (m, 2H), 6.97 (s, 2H, maleimide), 6.10 (br s, 1H), 5.35 (br s, 2H), 4.60-4.18 (m, 6H), 4.05-3.95 (m, 4H), 3.45-3.29 (m, 5H), 3.04-2.87 (m, 4H), 2.68-2.60 (m, 2H), 2.40-2.30 (m, 4H), 1.72-1.57 (m, 4H), 1.43-1.28 (m, 5H), 1.20-1.07 (m, 3H). $^{31}$P NMR (DMSO) δ −5.82 (s). HRMS (ESI) found m/z 1342.3562 (M+H). C$_{62}$H$_{68}$Cl$_2$N$_9$O$_{17}$P$_2$ requires 1342.3580.

2. LD-2

The CBI-CBI peptidomimetic linker dimer ((1S,1'S)-3,3'-((2E,2'E)-3,3'-(2-(3-((S)-2-(1-((5-(2,5-dioxo-2,5-dihydro-1H-pyrrol-1-yl)pentyl)carbamoyl)cyclobutanecarboxamido)-5-ureidopentanamido)propanamido)-1,4-phenylene)bis(acryloyl))bis(1-(chloromethyl)-2,3-dihydro-1H-benzo[e]indole-5,3-diyl) bis(dihydrogen phosphate), LD-2) having the formula:

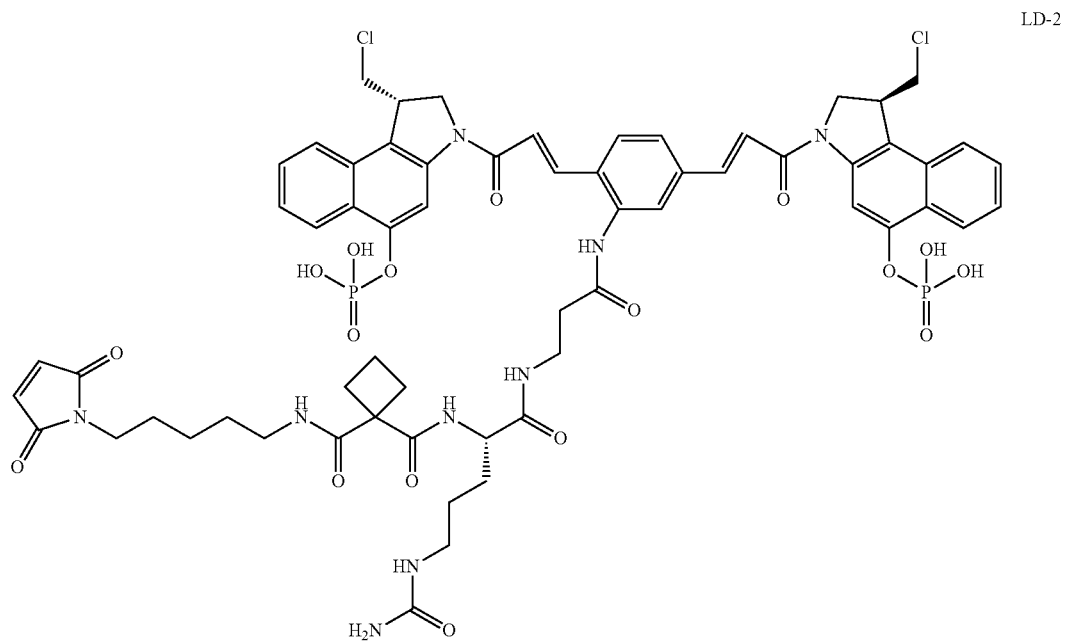 [SMILES: NC(=O)NCCC[C@H](NC(=O)C1(C(=O)NCCCCCN2C(=O)C=CC2=O)CCC1)C(=O)NCCC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21]

was synthesized as follows.

101

Step A: Synthesis of ethyl (S)-1-((1-((2,5-dioxopyr-rolidin-1-yl)oxy)-1-oxo-5-ureidopentan-2-yl)carbamoyl)cyclobutane-1-carboxylate 2b

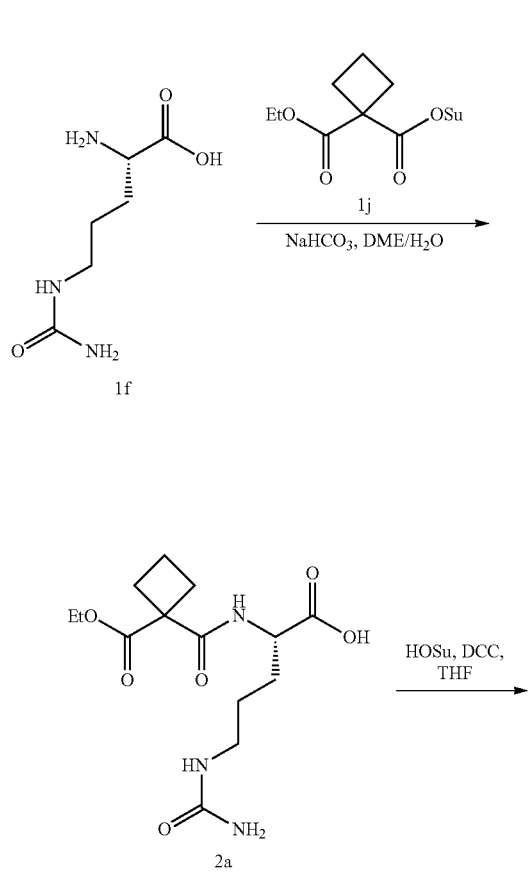

102

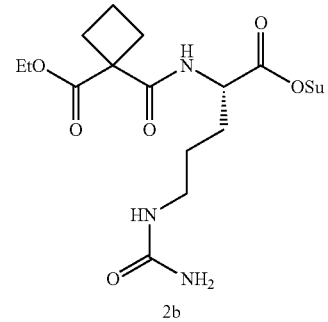

To a solution of (S)-2-amino-5-ureidopentanoic acid 1f (3.0 g, 17.1 mmol) in DME/H$_2$O (40 mL/20 mL) was added NaHCO$_3$ (2.88 g, 34.3 mmol). After the mixture was stirred at 25° C. for 15 min, 1-(2,5-dioxopyrrolidin-1-yl) 1-ethyl cyclobutane-1,1-dicarboxylate 1j (5.54 g, 20.6 mmol) was added. The mixture was stirred at 25° C. for 16 h under N$_2$. Solvents was removed and H$_2$O (5 mL) was added. It was extracted with EtOAc (30 mL×3). The pH of water phase was adjusted to 3 with HCl solution, and it was extracted with EtOAc (120 mL×3). The combined organic phase was dried over Na$_2$SO$_4$, and concentrated to give crude (S)-2-(1-(ethoxycarbonyl)cyclobutane-1-carboxamido)-5-ureidopentanoic acid 2a as colorless oil.

To a solution of 2a (5.64 g, 17.1 mmol) in dry THF (120 mL) was added HOSu (2.07 g, 17.98 mmol) and DCC (3.70 g, 17.98 mmol). The mixture was stirred at 25° C. for 15 h under N$_2$. It was filtered and concentrated. The residue was washed the with petroleum ether (PE) (30 mL×3), dried and concenrated to give crude 2b (8.30 g) as white solid.

Step B: Synthesis of 1-(((S)-1-((3-((2,5-bis((E)-3-(tert-butoxy)-3-oxoprop-1-en-1-yl)phenyl)amino)-3-oxopropyl)amino)-1-oxo-5-ureidopentan-2-yl)carbamoyl)cyclobutane-1-carboxylic acid 2f

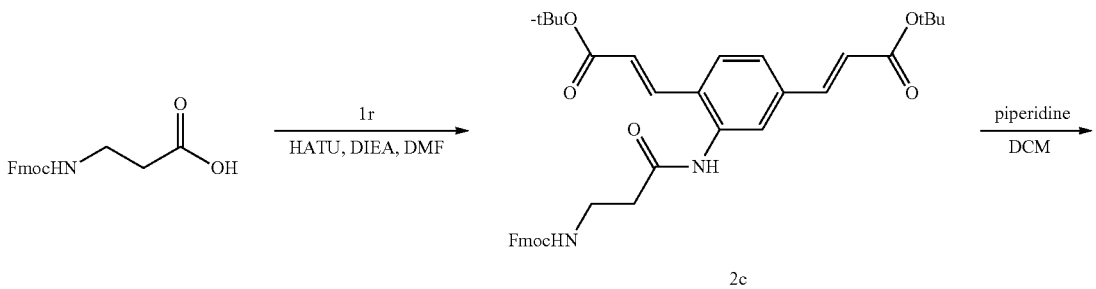

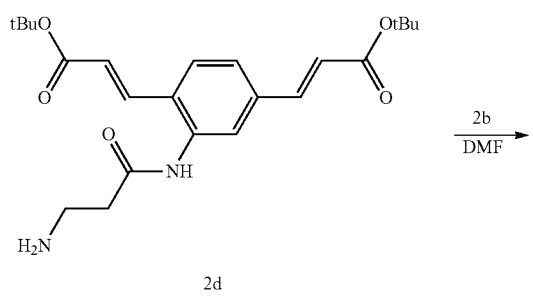

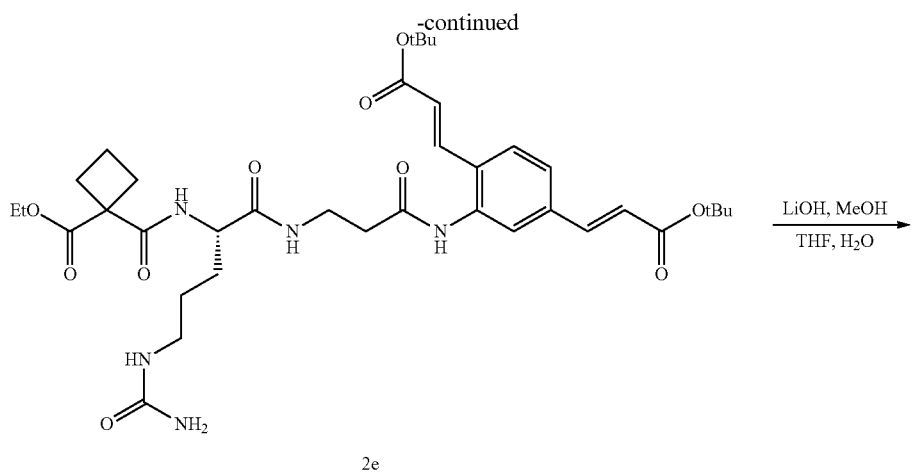

2e

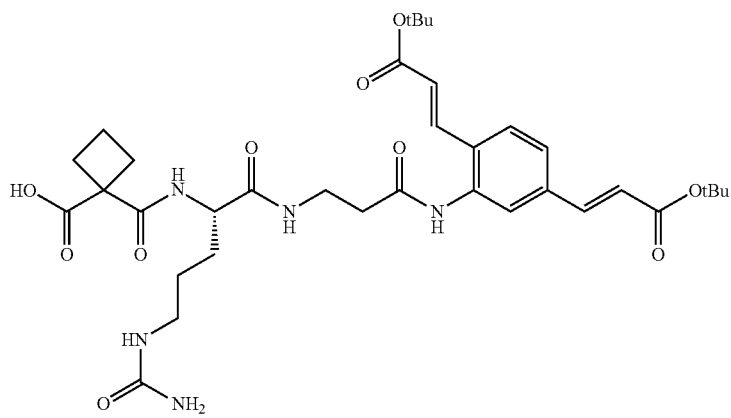

2f

To a stirred solution of 3-((((9H-fluoren-9-yl)methoxy) carbonyl)amino)propanoic acid (1.35 g, 4.34 mmol) in dry DMF (20 mL) was added HATU (2.20 g, 5.79 mmol), DIEA (1.12 g, 8.68 mmol). After the mixture was stirred at 25° C. for 10 min, (2E,2'E)-di-tert-butyl 3,3'-(2-amino-1,4-phenylene)diacrylate 1r (1.0 g, 2.89 mmol) was added. The reaction mixture was stirred at 25° C. for 15 h under $N_2$. Water (20 mL) was added and it was extracted with EtOAc (30 mL×3). The combined the organic phase was washed with brine, dried over $Na_2SO_4$, and concentrated. It was purified by flash column (PE: EtOAc=1:1) to give crude di-tert-butyl 3,3'-(2-(3-((((9H-fluoren-9-yl)methoxy)carbonyl)amino)propanamido)-1,4-phenylene)(2E,2'E)-diacrylate 2c (2.25 g) as yellow solid. LCMS: (5-95 AB, 1.5 min), 1.075 min, [M-114]+=527.0.

To a stirred solution of 2c (1.95 g, 3.05 mmol) in dry DCM (30 mL) was added piperidine (2.60 g, 30.5 mmol). The mixture was stirred at 25° C. for 2.5 h under $N_2$. It was washed with $H_2O$ (20 mL×3), brine (15 mL), and dried over $Na_2SO_4$. It was concentrated, washed with PE (20 mL×3), and dried to give crude di-tert-butyl 3,3'-(2-(3-aminopropanamido)-1,4-phenylene)(2E,2'E)-diacrylate 2d (2.4 g) as a yellow solid.

To a solution of compound 2d (1.65 g, 3.96 mmol) in dry DMF (20 mL) was added 2b (2.03 g, 4.75 mmol). The mixture was stirred at 25° C. for 15 h under $N_2$. Water (30 mL) was added and it was extracted with EtOAc (30 mL×3). The combined organic phase was washed with brine (30 mL), and dried over $Na_2SO_4$. It was concentrated to give crude product, which was washed the with PE (30 mL×4) and MTBE/PE (15 mL/45 mL×2), and dried to give di-tert-butyl 3,3'-(2-(3-((S)-2-(1-(ethoxycarbonyl)cyclobutane-1-carboxamido)-5-ureidopentanamido)propanamido)-1,4-phenylene)(2E,2'E)-diacrylate 2e (0.96 g, yield: 33%) as light yellow solid.

To a solution of 2e (0.96 g, 1.32 mmol) in MeOH (4 mL), THF (8 mL) and $H_2O$ (8 mL) was added LiOH—$H_2O$ (111 mg, 2.64 mmol). The mixture was stirred at 25° C. for 30 min under $N_2$. Organic solvents was removed under reduced pressure and $H_2O$ (10 mL) was added. HCl solution was added to adjust pH to 3-4. It was extracted with EtOAc (50 mL×4), dried over $Na_2SO_4$, and concentrated to give crude product. The crude product was washed with PE (30 mL) and MTBE (10 mL×3), and dried to give 2f (620 mg, yield: 67%) as white solid.

Step C: Synthesis of (2E,2'E)-3,3'-(2-(3-((S)-2-(1-((5-(2,5-dioxo-2,5-dihydro-1H-pyrrol-1-yl)pentyl)carbamoyl)cyclobutane-1-carboxamido)-5-ureidopentanamido)propanamido)-1,4-phenylene) diacrylic acid 2h

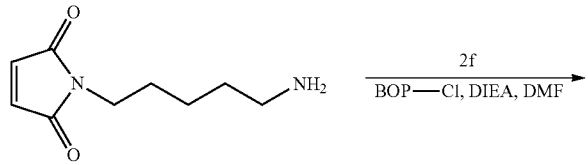

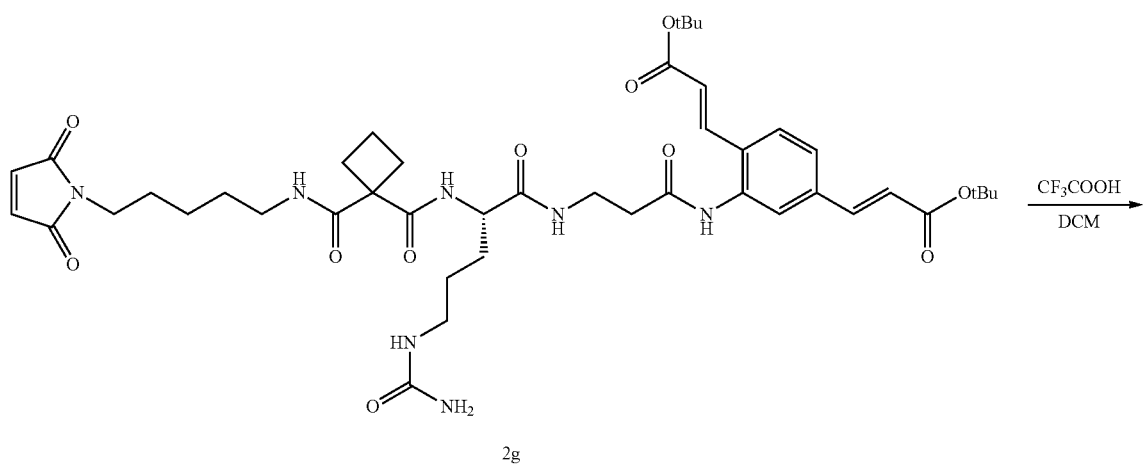

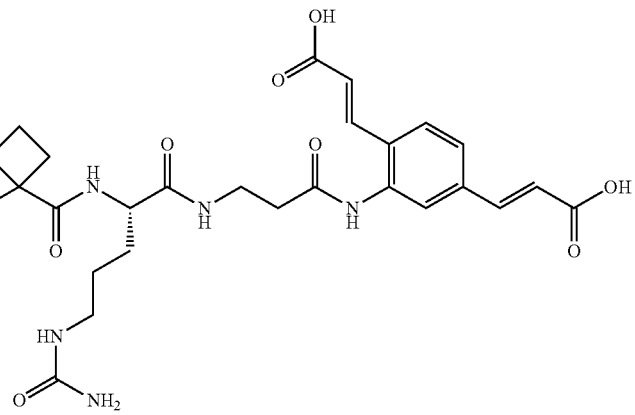

To a solution of 2f (620 mg, 0.89 mmol) in dry DMF (10 mL) was added DIEA (573 mg, 4.43 mmol) and Bop-Cl (248 mg, 0.97 mmol) at 0° C. 1-(5-Aminopentyl)-1H-pyrrole-2,5-dione (177.59 mg, 0.97 mmol) was added. After the mixture was stirred at 0° C. for 30 min under $N_2$, $H_2O$ (20 mL) was added and it was extracted with EtOAc (30 mL×3). The combined organic phase was washed with brine (30 mL), dried over $Na_2SO_4$, and concentrated to give crude product. It was washed with MTBE (10 mL×2) and PE (50 mL×3), and dried to give di-tert-butyl 3,3'-(2-(3-((S)-2-(1-((5-(2,5-dioxo-2,5-dihydro-1H-pyrrol-1-yl)pentyl)carbamoyl)cyclobutane-1-carboxamido)-5-ureidopentanamido)propanamido)-1,4-phenylene)(2E,2'E)-diacrylate 2g (690 mg, yield: 90%) as white solid. LCMS: (5-95 AB, 1.5 min), 0.875 min, MS=864.2 [M+1];

To a stirred solution of 2g (300 mg, 0.347 mmol) in dry DCM (4.0 mL) was added dropwise TFA (2.0 mL). After the mixture was stirred at 25° C. for 30 min under $N_2$, solvent was removed. The residue was dissolved in DMF and purified by prep-HPLC (HCOOH) to give 2h (81.4 mg, yield: 31%) as light yellow powder. $^1$H NMR (400 MHz, DMSO-d6) δ 9.93 (s, 2H), 6.13 (s, 1H), 7.82-7.46 (m, 8H), 6.98 (s, 2H), 6.55-6.51 (d, J=16.0 Hz, 2H), 5.98 (s, 1H), 5.41 (s, 2H), 4.22 (s, 1H), 3.03-2.90 (m, 6H), 2.67-2.50 (m, 4H), 2.36 (s, 4H), 1.69 (s, 3H), 1.46-1.33 (m, 7H), 1.23-1.16 (d, J=28 Hz, 2H).

Step D: Synthesis of LD-2

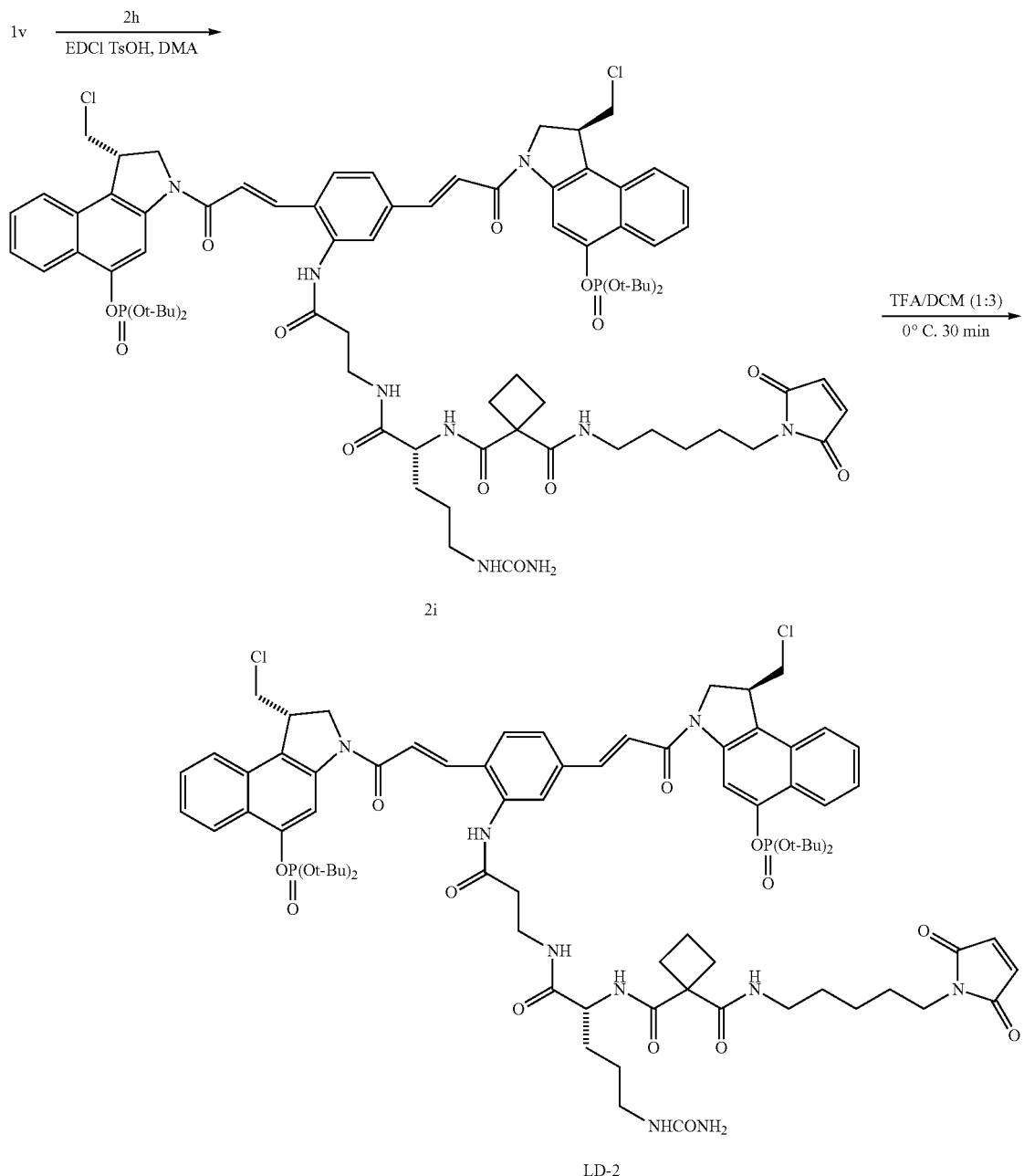

To 180 mg (0.42 mmol) of (S)-di-tert-butyl (1-(chloromethyl)-2,3-dihydro-1H-benzo[e]indol-5-yl) phosphate 1v (freshly made by the procedure mentioned above) was added 2h (100 mg, 0.12 mmol), EDCI.HCl (185 mg, 0.96 mmol), toluenesulfonic acid (2.1 mg, 0.012 mmol) and DMA (0.5 mL). After the mixture was stirred overnight, most of the DMA was removed under vacuum and the residue was redistributed between ethyl acetate and aq. NaHCO₃. The aqueous phase was extracted with ethyl acetate three times. The combined organic extracts were washed with water followed by brine, dried over anhydrous Na₂SO₄, and filtered through a pad of Celite. The solvent was removed and the resultant residue was dissolved in the minimum DCM and precipitated by adding heptane to give crude product (207 mg), which was further purified by preparative HPLC [Column: Synergi-Max RP 4 μ, 250×21.20 mm; Mobile phase: A/B=from 20% to 1% (A: ammonium formate pH 3.45, B: 90% acetonitrile in water); flow rate 12 mL/min] to give tetra-tert-butyl ((1S,1'S)-((2E,2'E)-3,3'-(2-(3-((R)-2-(1-((5-(2,5-dioxo-2,5-dihydro-1H-pyrrol-1-yl)pentyl)carbamoyl)cyclobutane-1-carboxamido)-5-ureidopentanamido) propanamido)-1,4-phenylene)bis(acryloyl))bis(1-(chloromethyl)-2,3-dihydro-1H-benzo[e]indole-3,5-diyl)) bis(phosphate) 2i (65 mg, 33%) as a yellow solid. ¹H NMR (CDCl$_3$) δ 9.67 (br s, 1H), 8.67 (br s, 2H), 8.18-7.98 (m, 4H), 7.90-7.72 (m, 3H), 7.66-7.58 (m, 6H), 7.50-7.28 (m, 8H), 6.84-6.62 (m, 4H), 6.66 (s, 2H, maleimide), 6.00 (br s, 1H), 5.23-5.13 (m, 2H), 4.80-4.70 (m, 1H), 4.40-3.85 (m, 6H), 3.50-3.40 (m, 6H), 3.20-3.14 (m, 2H), 2.90-2.75 (m, 2H), 2.60-2.45 (m, 4H), 1.92-1.80 (m, 2H), 1.62, 1.60, 1.57, 1.56 (4s, 36H), 1.55-1.40 (m, 6H), 1.30-1.20 (m, 3H). $^{31}$P NMR (CDCl$_3$) δ −15.44 (s), 15.82 (s). HRMS (ESI) found m/z 1666.6051 (M+Na). C$_{83}$H$_{101}$Cl$_2$N$_9$NaO$_{18}$P$_2$ requires 1666.6009.

To a solution of 2i (25 mg, 0.015 mmol) in DCM (0.6 mL) cooled in an ice bath was added TFA (0.2 mL, 2.61 mmol). The mixture was stirred in an ice bath for 0.5 h. All the volatile components were pumped off at 0° C. and the resultant residue was triturated with ethyl acetate, then washed with THF and petroleum ether to give LD-2 as a yellow solid (19 mg, 88%). $^1$H NMR (DMSO) δ 10.33 (br s, 1H), 9.63 (s, 1H), 8.70 (s, 1H), 8.95 (s, 1H), 8.14-8.11 (m, 4H), 7.96-7.90 (m, 4H), 7.81-7.69 (m, 6H), 7.64-7.54 (m, 2H), 7.50-7.39 (m, 4H), 7.33-7.26 (m, 2H), 6.97 (s, 2H, maleimide), 6.13 (br s, 2H), 5.14 (s, 2H), 4.58 (s, 4H), 4.40-4.30 (m, 4H), 4.08-3.95 (m, 4H), 3.29 (t, J=6.9 Hz, 2H), 2.99-2.94 (m, 4H), 2.39-2.33 (m, 2H), 1.71-1.67 (m, 4H), 1.40-1.35 (m, 6H), 1.12-1.10 (m, 3H). $^{31}$P NMR (DMSO) δ −5.91 (s). HRMS (ESI) found m/z 1442.3438 (M+Na). C$_{67}$H$_{69}$Cl$_2$N$_9$NaO$_{18}$P$_2$ requires 1442.3505.

C. Conjugation of linker-drug moieties to antibodies

Antibody drug conjugates are produced by conjugating the selected antibody (in some embodiments, with an engineered cysteine, for example, at light chain K149) to the selected drug-linker moiety (i.e., intermediate). For example, anti-Ly6E hu9B12v12 antibody-drug conjugates (ADCs) are produced by conjugating hu9B12v12 with a light chain K149C mutation ("thio-hu9B12v12 K149C" or "thio Hu anti-Ly6E LC K-149C") to the selected drug-linker moiety.

As initially isolated, the engineered cysteine residues in antibodies exist as mixed disulfides with cellular thiols (e.g., glutathione) and are thus unavailable for conjugation. Partial reduction of these antibodies (e.g., with DTT), purification, and reoxidation with dehydroascorbic acid (DHAA) gives antibodies with free cysteine sulfhydryl groups available for conjugation, as previously described, e.g., in Junutula et al. (2008) *Nat. Biotechnol.* 26:925-932 and US 2011/0301334. Briefly, the antibodies are combined with the drug-linker moiety to allow conjugation of the drug-linker moiety to the free cysteine residues of the antibody. After several hours, the ADCs are purified. The drug load (average number of drug moieties per antibody) for each ADC was determined and was about 2.

The resulting ADC structures and the terms used for them are shown in Table 3.

TABLE 3

Ly6E Antibody-drug conjugates (ADC)

| ADC | ADC formula | linker-drug LD No. (Table 2) | DAR* |
|---|---|---|---|
| ADC-101 | Thio Hu Anti-Ly6E 9B12.v12 LC K149C-(LD-1) | LD-1 | 2 |
| ADC-102 | Thio Hu Anti-Ly6E 9B12.v12 LC K149C-(LD-2) | LD-2 | 2 |
| ADC-103 | Thio Hu-Anti Ly6E 9B12.v12 LC K149C-(LD-3) | LD-3 | 2 |

Example 2

Efficacy of hu9B12v12 Antibody Drug Conjugates in HCC1569X2 Human Tumor Xenograft Models The HCC1569 human breast cancer cell line was obtained from ATCC (American Type Culture Collection; Manassas, Va.) and a sub-line HCC1569X2 was generated at Genentech for optimal growth in mice.

Female C.B-17 SCID-beige mice (Charles River Laboratory) were each inoculated in the thoracic mammary fat pad area with 5 million HCC1569X2 cells suspended in HBSS/matrigel (1:1 ratio). When the xenograft tumors reached an average tumor volume of 100-300 mm$^3$ (referred to as Day 0), animals were randomized into groups of 5 mice each and received a single intravenous injection of the antibody-drug conjugate through tail vein. Tumors and body weights of mice were measured 1-2 times a week throughout the study. Mice were promptly euthanized when body weight loss was >20% of their starting weight. All animals were euthanized before tumors reached 3000 mm$^3$ or showed signs of impending ulceration. Tumor volume was measured in two dimensions (length and width) using calipers and the tumor volume was calculated using the formula: Tumor size (mm$^3$) =(longer measurement×shorter measurement$^2$)×0.5.

In the first experiment, mice were administered a single IV injection of Thio Hu Anti-Ly6E 9B12.v12 LC K149C-(LD-1) at 0.2 mg/kg, 0.5 mg/kg, or 1 mg/kg; or Thio Hu Anti-Ly6E 9B12.v12 LC K149C-(LD-2) at 0.2 mg/kg, 0.5 mg/kg, or 1 mg/kg; an isotype-matched Thio control antibody LC K149C-(LD-1) at 0.5 mg/kg; or an isotype-matched Thio control antibody LC K149C-(LD-2) at 0.5 mg/kg.

Figure 2:
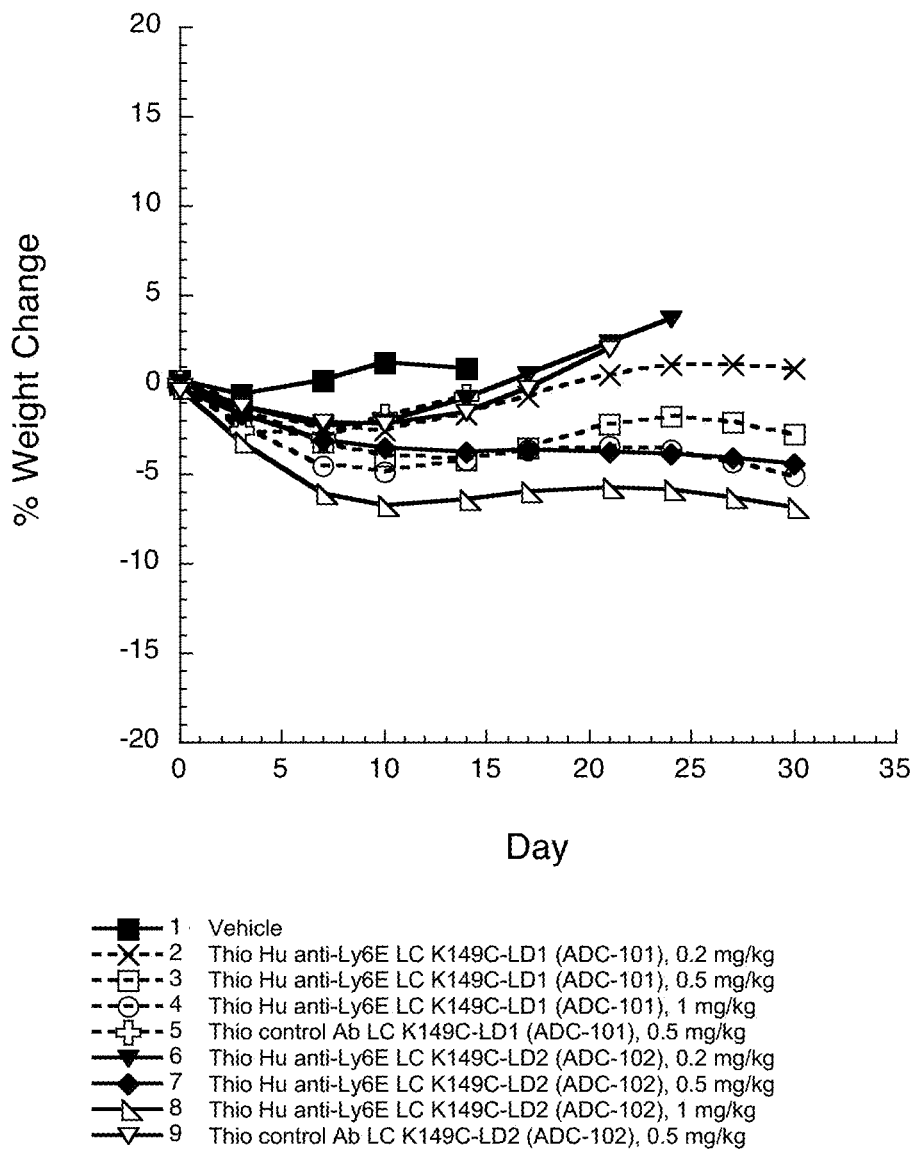
FIG. 2 shows change in body weight over time in mice bearing HCC1569X2 tumors upon treatment with anti-Ly6E immunoconjugates, as described in Example 2.

The results of that experiment are shown in FIG. 1. Thio Hu Anti-Ly6E 9B12.v12 LC K149C-(LD-1) showed efficacy at all doses, and Thio Hu Anti-Ly6E 9B12.v12 LC K149C-(LD-2) showed efficacy at 0.5 mg/kg and above. As shown in FIG. 2, none of the doses resulted in significant body weight change in the mice.

In the second experiment, mice were administered a single IV injection of Thio Hu Anti-Ly6E 9B12.v12 LC K149C-(LD-3) at 0.3 mg/kg, 0.5 mg/kg, 1 mg/kg; 3 mg/kg, 6 mg/kg, or 10 mg/kg; or an isotype-matched Thio control antibody LC K149C-(LD-3) at 3 mg/kg.

Figure 3:
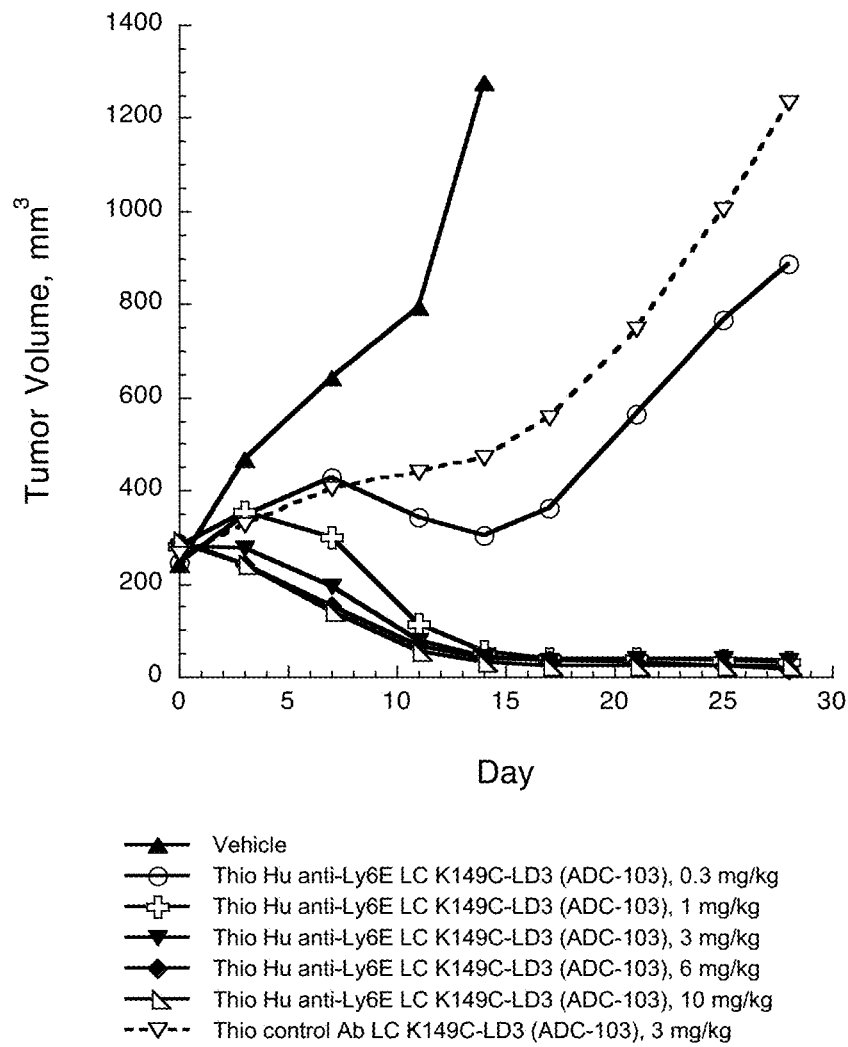
FIG. 3 shows change in tumor volume ($mm^3$) over time in a mouse HCC1569X2 xenograft model upon treatment with anti-Ly6E immunoconjugates, as described in Example 2.
Figure 4:
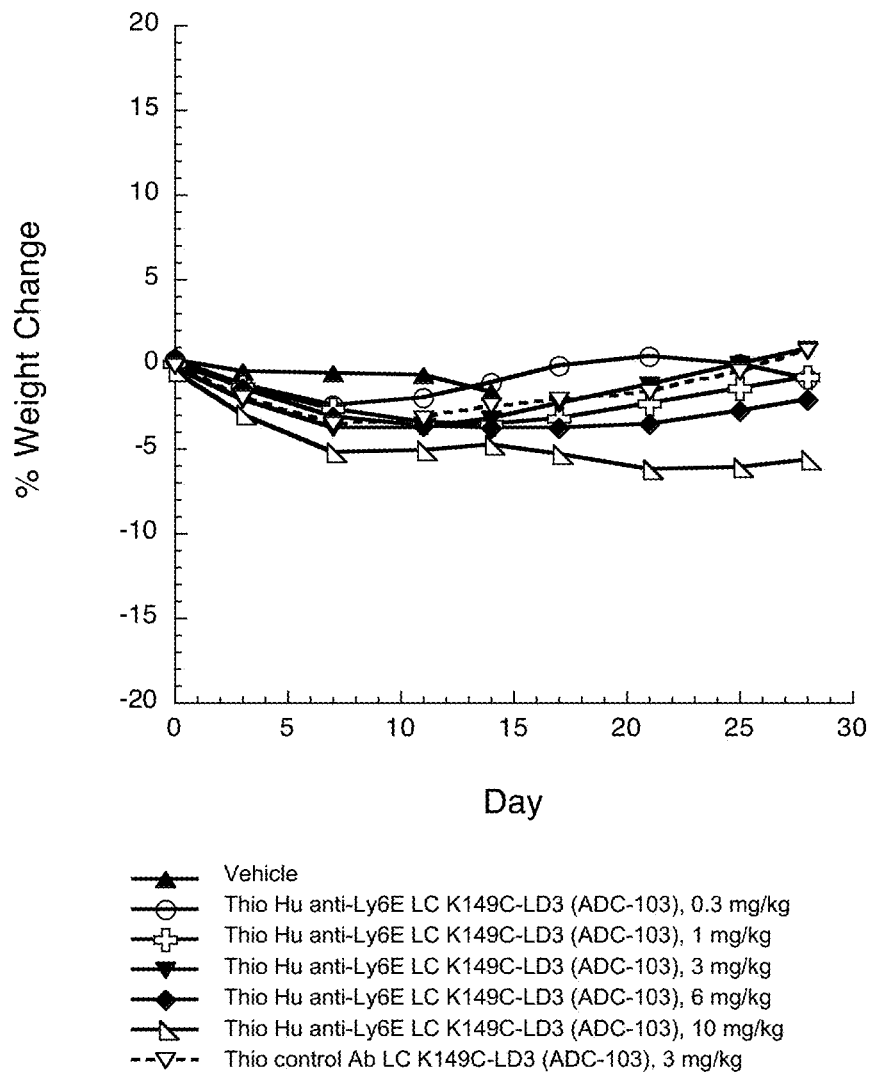
FIG. 4 shows change in body weight over time in mice bearing HCC1569X2 tumors upon treatment with anti-Ly6E immunoconjugates, as described in Example 2.
Figure 5:
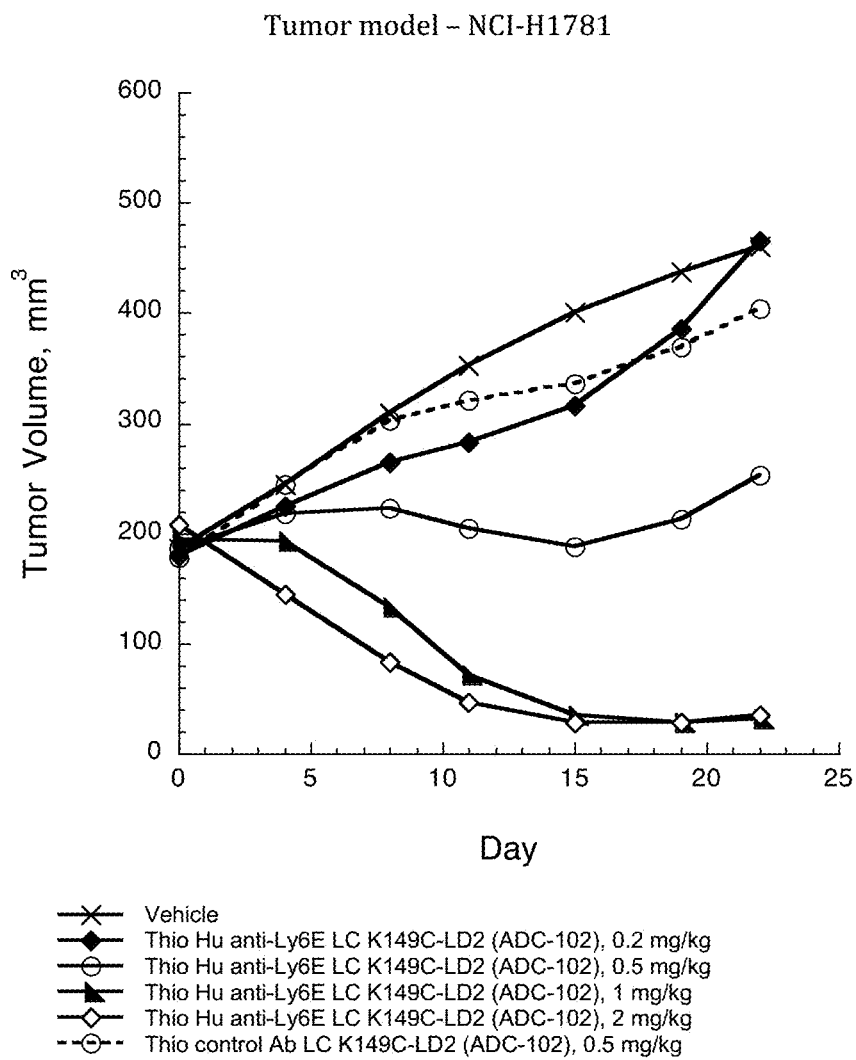
FIG. 5 shows change in tumor volume ($mm^3$) over time in a mouse NCI-H1781 xenograft model upon treatment with anti-Ly6E immunoconjugates, as described in Example 3.
Figure 6:
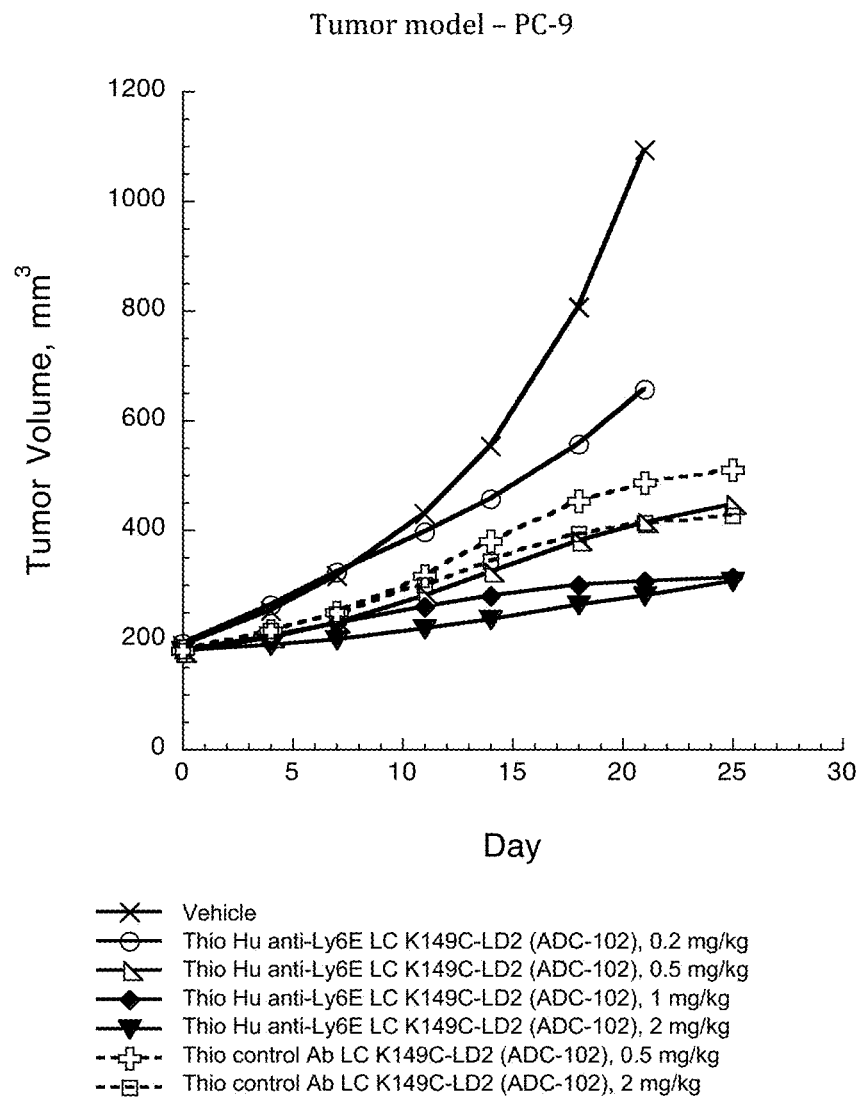
FIG. 6 shows change in tumor volume ($mm^3$) over time in a mouse PC-9 xenograft model upon treatment with anti-Ly6E immunoconjugates, as described in Example 3.
Figure 7:
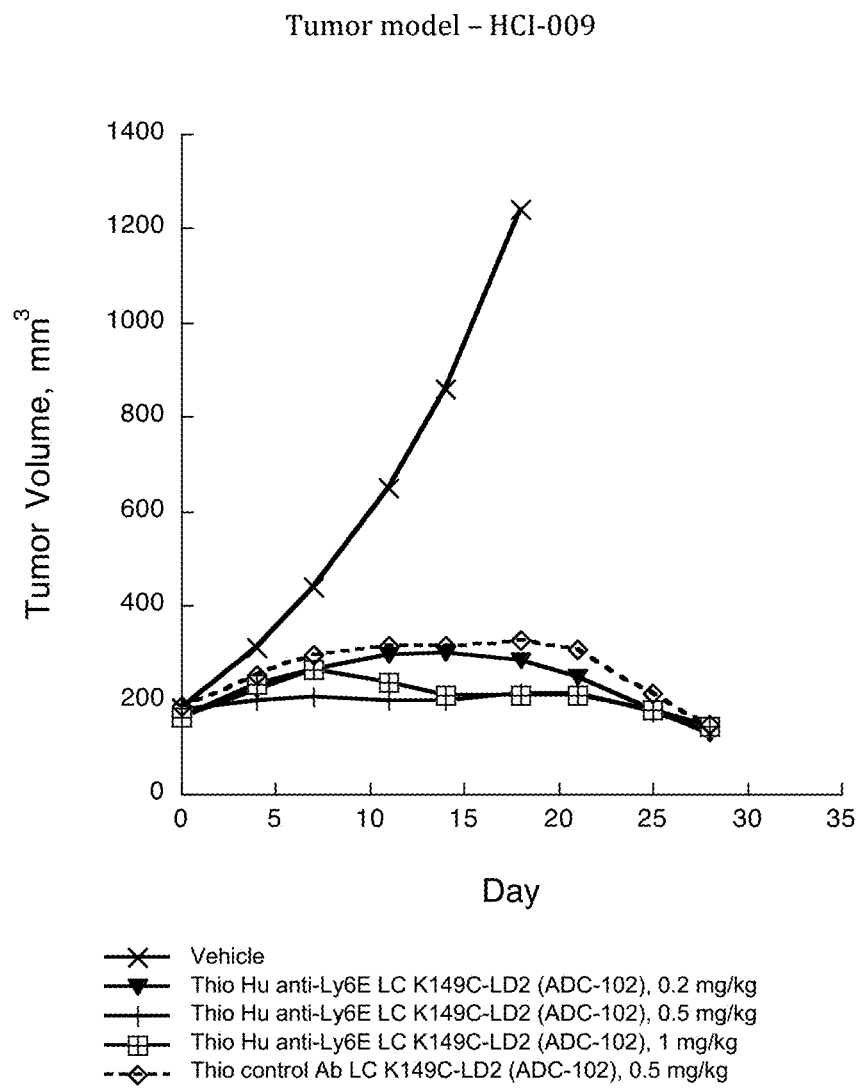
FIG. 7 shows change in tumor volume ($mm^3$) over time in a mouse HCI-009 xenograft model upon treatment with anti-Ly6E immunoconjugates, as described in Example 3.
Figure 8:
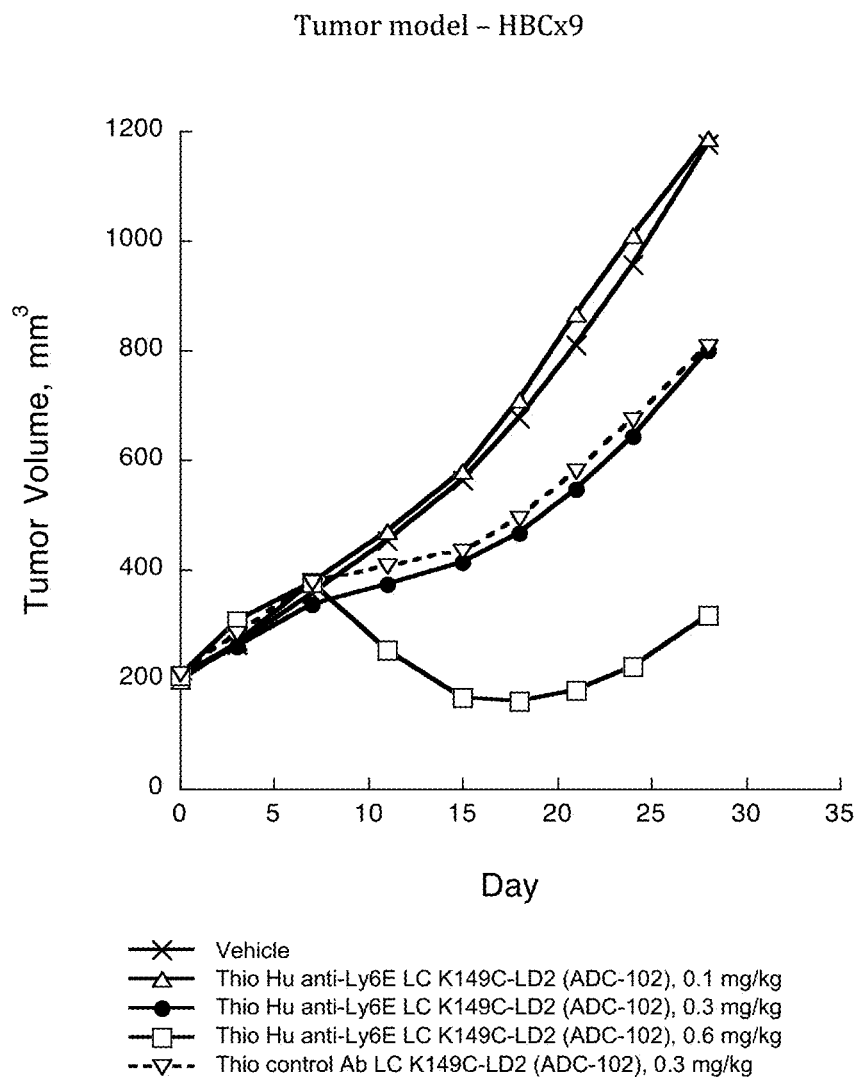
FIG. 8 shows change in tumor volume ($mm^3$) over time in a mouse HBCx9 xenograft model upon treatment with anti-Ly6E immunoconjugates, as described in Example 3.

The results of that experiment are shown in FIG. 3. Thio Hu Anti-Ly6E 9B12.v12 LC K149C-(LD-3) showed efficacy at 1 mg/kg and above. As shown in FIG. 4, none of the doses resulted in significant body weight change in the mice.

Example 3

Ly6E Immunohistochemistry (IHC) Staining and Efficacy of hu9B12v12 Antibody Drug Conjugates in Additional Human Tumor Xenograft Models Additional human tumor xenograft models were performed using different Ly6E-expressing tumor cells and tissues, including patient-derived xenografts (PDX) having heterogeneous Ly6E expression. The efficacy of LY6E antibody drug conjugates was investigated in mouse xenograft models of NCI-H1781 (lung adenocarcinoma), PC-9 (human non-small cell lung cancer), HCI-009 (patient-derived triple negative breast cancer), and HBCx9 (patient-derived triple negative breast cancer).

The antibody-drug conjugates were tested in various human tumor derived xenograft models that demonstrate variable Ly6E expression levels, as measured by IHC. The expression and scoring of Ly6E expression in human tumors and matched normal tissues was performed using an automated immunohistochemistry procedure for the detection of Ly6E in formalin fixed, paraffin embedded tissues (FFPE). Scoring was based on localization of Ly6E to the cell membrane and cytoplasm. See Asundi et al., *Clin Cancer Res.*, Jul. 15, 2015; 21: 3252-3262.

Two staining scores were calculated, an "overall score" and an "Histo-score" (or H-score). An "overall score" involves determination of a percentage threshold (e.g., at least 50% of cells express some signal at any intensity), and the predominant intensity of staining. See Table 4.

TABLE 4

Specific staining criteria for Ly6E immunohistochemistry

| Membranous/Cytoplasmic Staining Intensity in Tumor Cells | LY6E Scoring Assignment | Assay Interpretation |
|---|---|---|
| ≥50% of tumor cells must stain positive and the predominant staining intensity is 3+, denoting strong staining | 3+ | Positive |
| ≥50% of tumor cells must stain positive and the predominant staining intensity is 2+, indicating predominantly moderate staining | 3+ | Positive |
| ≥50% of tumor cells must stain positive and the predominant staining intensity is 1+, indicating predominantly weak staining | 1+ | Negative |
| <50% staining of tumor cells at any intensity | 0 | Negative |

In addition, "histo-scores (H-scores)" were calculated to capture Ly6E expression heterogeneity in the human tumor cell lines tested. See, e.g., McClelland et al., *Cancer Res.* 1990 Jun. 15; 50(12): 3545-50. Staining intensity was scored on a semi-quantitative integer scale from 0 (negative) to 3+(positive), and the percentage of viable malignant cells with positive staining at each intensity level is recorded. The H-score combines components of staining intensity with the percentage of positive cells. In some embodiments, this is a method of assessing the extent of immunoreactivity in tissue IHC experiments by averaging both the intensity and the frequency of expression. The H-score is obtained by the following formula:

[3×percentage of strong (3+) expression+2×percentage of moderate (2+) expression+1×percentage of weak (1+) expression]=$H$-score.

The final H-score, typically ranging from 0 to 300, gives more relative weight to higher-intensity immunoreactivity in a given tumor sample. The Ly6E immunohistochemistry (IHC) staining scores are summarized in Table 5.

TABLE 5

Ly6E IHC scores for human tumor cell lines

| Human cell line model | Overall Score | H-Score | % Ly6E positive |
|---|---|---|---|
| HCC1569X2 | 1+ to 2+ | 100-200 | 100% |
| NCI-H1781 | 1+ | 140 | 100% |
| PC-9 | 1+ | 120 | 100% |
| HBCx9 | 1+ | 40-100 | 30-80% |
| HCI-009 | 1+ to 2+ | 100-200 | 90-100% |

NCI-H1781 was obtained from ATCC (American Type Culture Collection; Manassas, Va.) and PC-9 from the Genentech, Inc. cell line repository. Cell lines were authenticated by short tandem repeat (STR) profiling using the Promega PowerPlex 16 System and compared with external STR profiles of cell lines to determine cell line ancestry. To establish the models, female C.B-17 SCID-beige mice (Charles River Laboratories) were each inoculated subcutaneously in the flank area with 5 million tumor cells suspended in HBSS/matrigel (1:1 ratio).

HCI-009 model was acquired from Huntsman Cancer Institute at the University of Utah. To establish the model, tumor fragments (15-30 mm$^3$ size) were surgically implanted into the thoracic mammary fat pad of female NOD SCID mice (Charles River Laboratories).

HBCx9 model was developed at Xentech, Inc. To establish the model, tumor fragments (20 mm$^3$ size) were surgically implanted subcutaneously in the interscapular region of the female athymic nude mice (Harlan Laboratories).

When tumors reached an average tumor volume of 100-300 mm$^3$, animals were randomized into groups of 5-10 mice each and received a single intravenous injection of Thio Hu Anti-Ly6E 9B12.v12 LC K149C-(LD-2) or an isotype-matched Thio control antibody LC K149C-(LD-2) at the indicated dose (referred to as Day 0). Tumors and body weights of mice were measured 1-2 times a week throughout the study. Mice were promptly euthanized when body weight loss was >20% of their starting weight. All animals were euthanized before tumors reached 3000 mm$^3$ or showed signs of impending ulceration. Tumor volume was measured in two dimensions (length and width) using calipers and the tumor volume was calculated using the formula: Tumor size (mm$^3$)=0.5×(length×width×width).

The results of those experiments are shown in FIGS. 5 to 8. Thio Hu Anti-Ly6E 9B12.v12 LC K149C-(LD-2) showed efficacy at 0.5 mg/kg and above in the NCI-H1781 lung cancer xenograft model, even with a low Ly6E IHC score. See FIG. 5. In the PC-9 non-small cell lung cancer xenograft model, Thio Hu Anti-Ly6E 9B12.v12 LC K149C-(LD-2) showed antigen-specific efficacy at 1 mg/kg and above; this model also had a low Ly6E IHC score. See FIG. 6.

In the HCI-009 triple-negative breast cancer PDX model, Thio Hu Anti-Ly6E 9B12.v12 LC K149C-(LD-2) did not show appreciable specific anti-tumor activity at the doses tested, even with a low to moderate Ly6E IHC score. See FIG. 7. In the HBCx9 triple-negative breast cancer PDX model, Thio Hu Anti-Ly6E 9B12.v12 LC K149C-(LD-2) showed anti-tumor activity at the higher dose of 0.6 mg/kg, with low to moderate LY6E staining score. See FIG. 8.

Example 4

Repeat-Dose Toxicity Study in Cynomolgus Monkeys

Cynomolgus monkeys are dosed IV every three weeks for 2 doses in order to understand, for example, the progression of toxicity, the reversibility and persistence of any drug-related effects, and to determine the therapeutic index (TI) using the antibody-drug conjugates. A summary of the experimental design is shown in Table 6 below. Briefly, dose levels are 2, 4, and 8 mg/kg administered in two doses, 3 weeks apart for each animal. For Groups 1-4, 7 and 8, two doses are administered, on Days 1 and 22. For Groups 5, 6, 9 and 10, four doses are administered, on Days 1, 22, 43 and 64.

TABLE 6

Cynomolgus monkey experimental design

| Group No. | Test Material | Dose Level (mg/kg) | Dose Volume (mL/kg) | Dose Concentration (mg/mL) | No of Animals Female |
|---|---|---|---|---|---|
| 1 | Vehicle Control | 0 | 2.5 | 0 | 1 |
| 2 | Thio Hu Anti-Ly6E 9B12.v12 LC K149C-(LD-2) | 2 | 2.5 | 0.8 | 3* |
| 3 | Vehicle Control | 0 | 2.5 | 0 | 1 |
| 4 | Thio Hu Anti-Ly6E 9B12.v12 LC K149C-(LD-2) | 4 | 2.5 | 1.6 | 3* |
| 5 | Vehicle Control | 0 | 2.5 | 0 | 1 |
| 6 | Thio Hu Anti-Ly6E 9B12.v12 LC K149C-(LD-2) | 4 | 2.5 | 1.6 | 3* |
| 7 | Vehicle Control | 0 | 2.5 | 0 | 1 |
| 8 | Thio Hu Anti-Ly6E 9B12.v12 LC K149C-(LD-2) | 4 | 2.5 | 1.6 | 3* |
| 9 | Thio Hu Anti-Ly6E 9B12.v12 LC K149C-(LD-2) | 8 | 2.5 | 3.2 | 1 |
| 10 | Thio Hu Anti-Ly6E 9B12.v12 LC K149C-(LD-2) | 2 | 2.5 | 0.8 | 3 |

*Dose one animal on Day 1, three animals after 14 days.

Each animal is evaluated for new observations or increases in the severity of existing observations following dose administration. Each animal is observed for changes in general appearance and behavior. Body weights are taken at least twice pre-treatment (e.g., at Weeks minus 2 and minus 1, at least one week apart), and on Day minus 1, and weekly thereafter. Bioanalytical sample analyses include, but will not be limited to, collection of plasma samples for toxicokinetic (TK) stability; and anti-therapeutic antibody (ATA) samples will be collected if the toxicokinetic results show high variability. Test parameters include, but are not limited to, area under the concentration-time curve (AUC), maximum concentration, terminal half-life, clearance and volumes of distribution.

The dose levels selected for the cynomolgus monkey studies are based on information from previous toxicity studies in rats dosed with the same drug conjugated to a non-Ly6E antibody. Rats dosed at 20 mg/kg were euthanized as a result of excessive body weight loss, and the maximum tolerated dose (MTD) was about 10 mg/kg (data not shown).

For the cynomolgus monkeys, it is found that the 4 mg/kg was well-tolerated but the 8 mg/kg is not tolerated, therefore a lower dose level (2 mg/kg in test Group No. 10) is added to the study and dosed every three weeks for 4 doses.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| Sequence ID Number | Description | Sequence |
|---|---|---|
| 1 | anti-Ly6E antibody hu9B12 v12 light chain variable region | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK |
| 2 | anti-Ly6E antibody hu9B12 v12 heavy chain variable region | EVQLVESGPA LVKPTQTLTL TCTVSGFSLT GYSVNWIRQP PGKALEWLGM IWGDGSTDYN SALKSRLTIS KDTSKNQVVL TMTNMDPVDT ATYYCARDYY FNYASWFAYW GQGTLVTVSS |
| 3 | anti-Ly6E antibody hu9B12 v12 HVR-L1 | SASQGISNYLN |
| 4 | anti-Ly6E antibody hu9B12 v12 HVR-L2 | YTSNLHS |
| 5 | anti-Ly6E antibody hu9B12 v12 HVR-L3 | QQYSELPWT |
| 6 | anti-Ly6E antibody hu9B12 v12 HVR-H1 | GFSLTGYSVN |
| 7 | anti-Ly6E antibody hu9B12 v12 HVR-H2 | MIWGDGSTDY NSALKS |
| 8 | anti-Ly6E antibody hu9B12 v12 HVR-H3 | DYYFNYASWFAY |
| 9 | anti-Ly6E antibody hu9B12 v12 K149C kappa | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK RTVAAPSVFIF |

-continued

Table of Sequences

| Sequence ID Number | Description | Sequence |
|---|---|---|
|  | light chain | PPSDEQLKSG TASVVCLLNN FYPREAKVQW CVDNALQSGN SQESVTEQDS KDSTYSLSST LTLSKADYEK HKVYACEVTH QGLSSPVTKS FNRGEC |
| 10 | anti-Ly6E antibody hu9B12 v12 IgG1 heavy chain | EVQLVESGPA LVKPTQTLTL TCTVSGFSLT GYSVNWIRQP PGKALEWLGM IWGDGSTDYN SALKSRLTIS KDTSKNQVVL TMTNMDPVDT ATYYCARDYY FNYASWFAYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 11 | Trastuzumab light chain | DIQMTQSPSS LSASVGDRVT ITCRASQDVN TAVAWYQQKP GKAPKLLIYS ASFLYSGVPS RFSGSRSGTD FTLTISSLQP EDFATYYCQQ HYTTPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 12 | Trastuzumab light chain variable region | DIQMTQSPSS LSASVGDRVT ITCRASQDVN TAVAWYQQKP GKAPKLLIYS ASFLYSGVPS RFSGSRSGTD FTLTISSLQP EDFATYYCQQ HYTTPPTFGQ GTKVEIK |
| 13 | Trastuzumab heavy chain | EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP PKSCDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPGK |
| 14 | Trastuzumab heavy chain variable region | EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS |
| 15 | Anti-Muc16 antibody #1 HVR-L1 | KASDLIHNWL A |
| 16 | Anti-Muc16 antibody #1 HVR-L2 | SGATSLET |
| 17 | Anti-Muc16 antibody #1 HVR-L3 | QQYWTTPFT |
| 18 | Anti-Muc16 antibody #1 HVR-H1 | GYSITNDYAW N |
| 19 | Anti-Muc16 antibody #1 HVR-H2 | GYINYSGYTT YNPSL |
| 20 | Anti-Muc16 antibody #1 HVR-H3 | ARWDGGLTY |
| 21 | Anti-Muc16 antibody #1 light chain variable region | DIQMTQSSSF LSVSLGGRVT ITCKASDLIH NWLAWYQQKP GNAPRLLISG ATSLETGVPS RFSGSGSGND YTLSIASLQT EDAATYYCQQ YWTTPFTFGS GTKLEIK |

-continued

| Sequence ID Number | Description | Sequence |
|---|---|---|
| 22 | Anti-Muc16 antibody #1 heavy chain variable region | DVQLQESGPG LVNPSQSLSL TCTVTGYSIT NDYAWNWIRQ FPGNKLEWMG YINYSGYTTY NPSLKSRISI TRDTSKNQFF LHLNSVTTED TATYYCARWD GGLTYWGQGT LVTVSA |
| 23 | Anti-Muc16 antibody #2 HVR-L1 | KASDLIHNWL A |
| 24 | Anti-Muc16 antibody #2 HVR-L2 | YGATSLET |
| 25 | Anti-Muc16 antibody #2 HVR-L3 | QQYWTTPFT |
| 26 | Anti-Muc16 antibody #2 HVR-H1 | GYSITNDYAW N |
| 27 | Anti-Muc16 antibody #2 HVR-H2 | GYISYSGYTT YNPSLKS |
| 28 | Anti-Muc16 antibody #2 HVR-H3 | ARWTSGLDY |
| 29 | Anti-Muc16 antibody #2 light chain variable region | DIQMTQSPSS LSASVGDRVT ITCKASDLIH NWLAWYQQKP GKAPKLLIYG ATSLETGVPS RFSGSGSGTD FTLTISSLQP EDFATYYCQQ YWTTPFTFGQ GTKVEIKR |
| 30 | Anti-Muc16 antibody #2 heavy chain variable region | EVQLVESGGG LVQPGGSLRL SCAASGYSIT NDYAWNWVRQ APGKGLEWVG YISYSGYTTY NPSLKSRFTI SRDTSKNTLY LQMNSLRAED TAVYYCARWT SGLDYWGQGT LVTVSS |
| 31 | Anti-Muc16 antibody #3 HVR-L1 | KASDLIHNWL A |
| 32 | Anti-Muc16 antibody #3 HVR-L2 | YGATSLET |
| 33 | Anti-Muc16 antibody #3 HVR-L3 | QQYWTTPFT |
| 34 | Anti-Muc16 antibody #3 HVR-H1 | GYSITNDYAW N |
| 35 | Anti-Muc16 antibody #3 HVR-H2 | GYISYSGYTT YNPSLKS |
| 36 | Anti-Muc16 antibody # HVR-H3 | ARWASGLDY |
| 37 | Anti-Muc16 antibody #3 light chain variable region | DIQMTQSPSS LSASVGDRVT ITCKASDLIH NWLAWYQQKP GKAPKLLIYG ATSLETGVPS RFSGSGSGTD FTLTISSLQP EDFATYYCQQ YWTTPFTFGQ GTKVEIKR |
| 38 | Amti4duc16 antibody #3 heavy chain variable region | EVQLVESGGG LVQPGGSLRL SCAASGYSIT NDYAWNWVRQ APGKGLEWVG YISYSGYTTY NPSLKSRFTI SRDTSKNTLY LQMNSLRAED TAVYYCARWA SGLDYWGQGT LVTVSS |

-continued

| Sequence ID Number | Description | Sequence |
|---|---|---|
| 39 | Anti-Muc16 antibody #4 HVR-L1 | KASDLIHNWL A |
| 40 | Anti-Muc16 antibody #4 HVR-L2 | YGATSLET |
| 41 | Anti-Muc16 antibody #4 HVR-L3 | QQYWTTPFT |
| 42 | Anti-Muc16 antibody #4 HVR-H1 | GYSITNDYAW N |
| 43 | Anti-Muc16 antibody #4 HVR-H2 | GYINYAGYTT YNPSLKS |
| 44 | Anti-Muc16 antibody #4 HVR-H3 | ARWASGLDY |
| 45 | Anti-Muc16 antibody #4 light chain variable region | DIQMTQSPSS LSASVGDRVT ITCKASDLIH NWLAWYQQKP GKAPKLLIYG ATSLETGVPS RFSGSGSGTD FTLTISSLQP EDFATYYCQQ YWTTPFTFGQ GTKVEIKR |
| 46 | Anti-Muc16 antibody #4 heavy chain variable region | EVQLVESGGG LVQPGGSLRL SCAASGYSIT NDYAWNWVRQ APGKGLEWVG YINYAGYTTY NPSLKSRFTI SRDTSKNTLY LQMNSLRAED TAVYYCARWA SGLDYWGQGT LVTVSS |
| 47 | huMA79bv28 heavy chain variable region | EVQLVESGGG LVQPGGSLRL SCAASGYTFS SYWIEWVRQA PGKGLEWIGE ILPGGGDTNY NEIFKGRATF SADTSKNTAY LQMNSLRAED TAVYYCTRRV PIRLDYWGQG TLVTVSS |
| 48 | huMA79bv28 light chain variable region | DIQLTQSPSS LSASVGDRVT ITCKASQSVD YEGDSFLNWY QQKPGKAPKL LIYAASNLES GVPSRFSGSG SGTDFTLTIS SLQPEDFATY YCQQSNEDPL TFGQGTKVEI KR |
| 49 | huMA79bv28 HVR H1 | GYTIFSSYWIE |
| 50 | huMA79bv28 HVR H2 | GEILPGGGTNYEIFKG |
| 51 | huMA79bv28 HVR H3 | TRRVPIRLDY |
| 52 | huMA79bv28 HVR L1 | KASQSVDYEGDSFLN |
| 53 | huMA79bv28 HVR L2 | AASNLES |
| 54 | huMA79bv28 HVR L3 | QQSNEDPLT |
| 55 | Anti-STEAP-1 HVR-H1 | GYSITSDYAWN |
| 56 | Anti-STEAP-1 HVR-H2 | GYISNSGSTSYNPSLKS |
| 57 | Anti-STEAP-1 HVR-H3 | ERNYDYDDYY YAMDY |
| 58 | Anti-STEAP-1 HVR-L1 | KSSQSLLYRS NQKNYLA |

| Sequence ID Number | Description | Sequence |
|---|---|---|
| 59 | Anti-STEAP-1 HVR-L2 | WASTRES |
| 60 | Anti-STEAP-1 HVR-L3 | QQYYNYPRT |
| 61 | Anti-STEAP1 heavy chain variable region | EVQLVESGGG LVQPGGSLRL SCAVSGYSIT SDYAWNWVRQ APGKGLEWVG YISNSGSTSY NPSLKSRFTI SRDTSKNTLY LQMNSLRAED TAVYYCARER NYDYDDYYA MDYWGQGTLV TVSS |
| 62 | Anti-STEAP1 light chain variable region | DIQMTQSPSS LSASVGDRVT ITCKSSQSLL YRSNQKNYLA WYQQKPGKAP KLLIYWASTR ESGVPSRFSG SGSGTDFTLT ISSLQPEDFA TYYCQQYYNY PRTFGQGTKV EIK |
| 63 | Humanized 7C2.v2.2.LA ("hu7C2") light chain variable region | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IK |
| 64 | Hu7C2 heavy chain variable region | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSS |
| 65 | Hu7C2 HVR-L1 | RASQSVSGSRFTYMH |
| 66 | Hu7C2 HVR-L2 | YASILES |
| 67 | Hu7C2 HVR-L3 | QHSWEIPPWT |
| 68 | Hu7C2 HVR-H1 | GYWMN |
| 69 | Hu7C2 HVR-H2 (Hu7C2.v2.1.S53L, S55A HVR-H2) | MIHPLDAEIRANQKFRD |
| 70 | Hu7C2 HVR-H3 | GTYDGGFEY |
| 71 | Humanized 7C2.v2.2.LA (hu7C2) K149C kappa light chain | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWCVDNALQ SGNSQESVTE QDSKDSTYSL SSTLTLSKAD YEKHKVYACE VTHQGLSSPV TKSFNRGEC |
| 72 | Hu7C2 IgG1 heavy chain | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 73 | Hu7C2.v2.1.S53M HVR-H2 | MIHPMDSEIRANQKFRD |
| 74 | Hu7C2.v2.1.S53L HVR-H2 | MIHPLDSEIRANQKFRD |
| 75 | Hu7C2.v2.1.E101K HVR-H3 | GTYDGGFKY |

Table of Sequences

| Sequence ID Number | Description | Sequence |
|---|---|---|
| 76 | V205C cysteine engineered light chain constant region (Igκ) | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPCTKS FNRGEC |
| 77 | A1Mcystenie engineered heavy chain constant region (IgG1) | CSTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 78 | K149C cysteine engineered light chain constant region (Igκ) | TVAAPSVFIF PPSDEQLKSG TASVVCLLNN FYPREAKVQW CVDNALQSGN SQESVTEQDS KDSTYSLSST LTLSKADYEK HKVYACEVTH QGLSSPVTKS FNRGEC |
| 79 | S400C cysteine engineered heavy chain constant region (IgG1) | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDCDGSFFLY SKLTVDKSRW QQGNVFSCSV MHEALHNHYT QKSLSLSPGK |
| 80 | Anti-HER2 HVR-H1 | GFNIKDTYIH |
| 81 | Anti-HER2 HVR-H2 | RIYPTNGYTRYADSVKG |
| 82 | Anti-HER2 HVR-H3 | WGGDGFYAMD |
| 83 | Anti-HER2 HVR-L1 | ITCRASQDVNTAVAW |
| 84 | Anti-HER2 HVR-L2 | SASFLYS |
| 85 | Anti-HER2 HVR-L3 | QQHYTTPPT |

What is claimed is:

1. An immunoconjugate comprising a structure selected from:

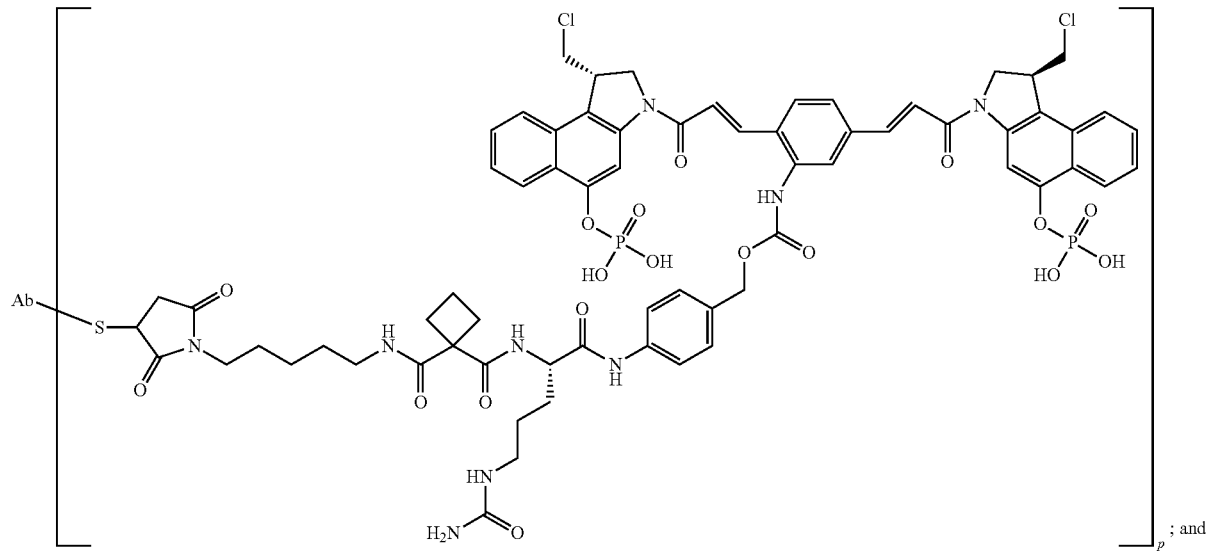

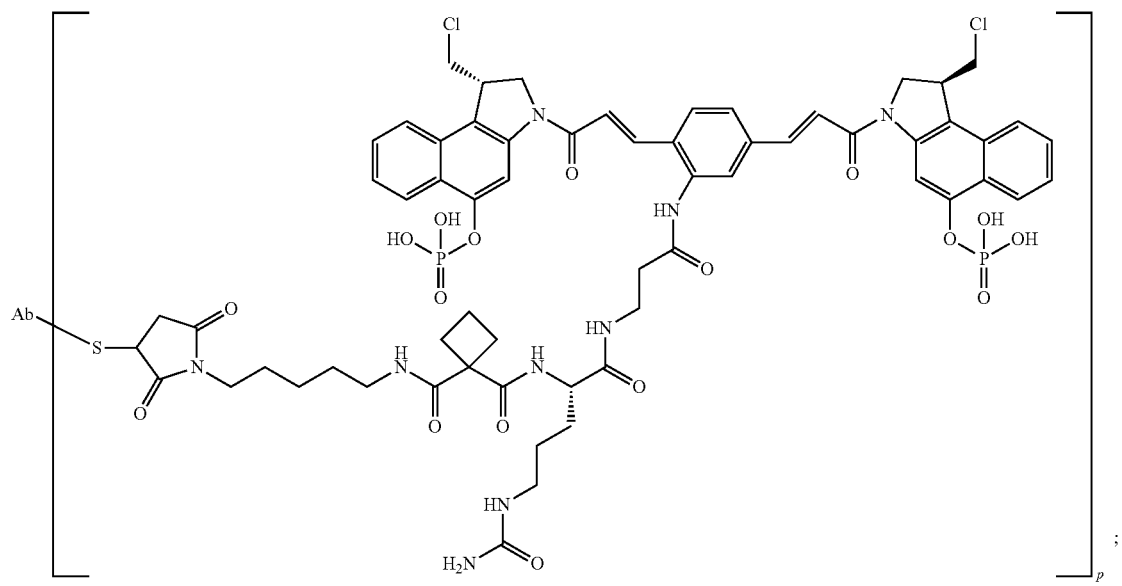

wherein p is from 1 to 4 and Ab is an antibody that binds Ly6E comprising an HVR-H1 comprising the amino acid sequence of SEQ ID NO: 6, and an HVR-H2 comprising the amino acid sequence of SEQ ID NO: 7; an HVR-H3 comprising the amino acid sequence of SEQ ID NO: 8; an HVR-L1 comprising the amino acid sequence of SEQ ID NO: 3; an HVR-L2 comprising the amino acid sequence of SEQ ID NO: 4; and an HVR-L3 comprising the amino acid sequence of SEQ ID NO: 5.

2. The immunoconjugate of claim 1, wherein Ab is an antibody that binds Ly6E comprising a heavy chain variable region comprising the amino acid sequence of SEQ ID NO: 2 and a light chain variable region comprising the amino acid sequence of SEQ ID NO: 1.

3. The immunoconjugate of claim 1, wherein the antibody is a monoclonal antibody.

4. The immunoconjugate of claim 1, wherein the antibody is a humanized or chimeric antibody.

5. The immunoconjugate of claim 1, wherein the antibody is an antibody fragment that binds to Ly6E.

6. The immunoconjugate of claim 1, wherein the antibody is an IgG1, IgG2a or IgG2b antibody.

7. The immunoconjugate of claim 1, wherein the antibody comprises at least one mutation in the heavy chain constant region selected from A118C and S400C.

8. The immunoconjugate of claim 7, wherein the antibody comprises a heavy chain constant region comprising the amino acid sequence of SEQ ID NO: 77 or 79.

9. The immunoconjugate of claim 1, wherein the antibody comprises at least one mutation in the light chain constant region selected from K149C and V205C.

10. The immunoconjugate of claim 9, wherein the antibody comprises a light chain constant region comprising the amino acid sequence of SEQ ID NO: 76 or 78.

11. The immunoconjugate of claim 1, wherein the antibody comprises a K149C mutation in the light chain constant region.

12. The immunoconjugate of claim 11, wherein the light chain constant region comprises the amino acid sequence of SEQ ID NO: 78.

13. The immunoconjugate of claim 1, wherein the antibody comprises a heavy chain comprising the sequence of SEQ ID NO: 10 and a light chain comprising the sequence of SEQ ID NO: 9.

14. The immunoconjugate of claim 1, wherein p ranges from 1 to about 2.

15. The immunoconjugate of claim 1, wherein p is about 2.

16. An immunoconjugate comprising the structure:

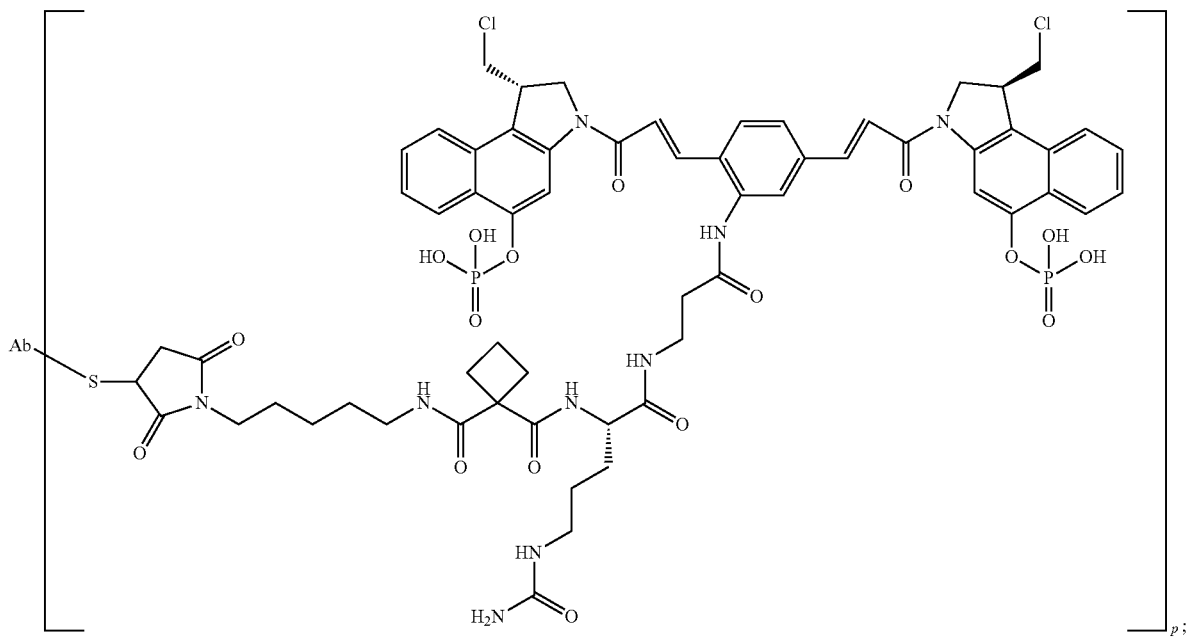

wherein Ab is an antibody comprising a heavy chain and a light chain, wherein the heavy chain comprises the sequence of SEQ ID NO: 10 and the light chain comprises the sequence of SEQ ID NO: 9; and p is 1 to about 2.

17. The immunoconjugate of claim 16, wherein p is about 2.

18. A pharmaceutical formulation comprising the immunoconjugate of claim 1 and a pharmaceutically acceptable carrier.

19. A method of treating a Ly6E-positive cancer comprising administering to an individual with a Ly6E-positive cancer an effective amount of the pharmaceutical formulation of claim 18.

20. The method of claim 19, wherein the cancer is selected from breast cancer, metastatic breast cancer, Her2 negative breast cancer, triple negative breast cancer, pancreatic cancer, colon cancer, colorectal cancer, melanoma, ovarian cancer, non-small cell lung cancer, and gastric cancer.

21. A method of inhibiting proliferation of a Ly6E-positive cell, comprising exposing the Ly6E-positive cell to an immunoconjugate of claim 1 under conditions permissive for binding of the immunoconjugate to an antigen on the surface of the cell, thereby inhibiting proliferation of the cell.

22. The immunoconjugate of claim 2, wherein the antibody is a monoclonal antibody.

23. The immunoconjugate of claim 2, wherein the antibody is an antibody fragment that binds to Ly6E.

24. The immunoconjugate of claim 2, wherein the antibody is an IgG1, IgG2a or IgG2b antibody.

25. The immunoconjugate of claim 2, wherein the antibody comprises at least one mutation in the heavy chain constant region selected from A118C and S400C.

26. The immunoconjugate of claim 25, wherein the antibody comprises a heavy chain constant region comprising the amino acid sequence of SEQ ID NO: 77 or 79.

27. The immunoconjugate of claim 2, wherein the antibody comprises at least one mutation in the light chain constant region selected from K149C and V205C.

28. The immunoconjugate of claim 27, wherein the antibody comprises a light chain constant region comprising the amino acid sequence of SEQ ID NO: 76 or 78.

29. The immunoconjugate of claim 2, wherein the antibody comprises a K149C mutation in the light chain constant region.

30. The immunoconjugate of claim 29, wherein the light chain constant region comprises the amino acid sequence of SEQ ID NO: 78.

31. The immunoconjugate of claim 2, wherein p ranges from 1 to about 2.

32. The immunoconjugate of claim 2, wherein p is about 2.

33. A pharmaceutical formulation comprising the immunoconjugate of claim 2 and a pharmaceutically acceptable carrier.

34. A method of treating a Ly6E-positive cancer comprising administering to an individual with a Ly6E-positive cancer an effective amount of the pharmaceutical formulation of claim 33.

35. The method of claim 34, wherein the cancer is selected from breast cancer, metastatic breast cancer, Her2 negative breast cancer, triple negative breast cancer, pancreatic cancer, colon cancer, colorectal cancer, melanoma, ovarian cancer, non-small cell lung cancer, and gastric cancer.

36. A pharmaceutical formulation comprising the immunoconjugate of claim 16 and a pharmaceutically acceptable carrier.

37. A method of treating a Ly6E-positive cancer comprising administering to an individual with a Ly6E-positive cancer an effective amount of the pharmaceutical formulation of claim 36.

38. The method of claim 37, wherein the cancer is selected from breast cancer, metastatic breast cancer, Her2 negative breast cancer, triple negative breast cancer, pancreatic cancer, colon cancer, colorectal cancer, melanoma, ovarian cancer, non-small cell lung cancer, and gastric cancer.

* * * * *